United States Patent
Bernfeld et al.

(10) Patent No.: US 10,494,597 B2
(45) Date of Patent: Dec. 3, 2019

(54) CONTAMINATION MITIGATION

(71) Applicant: Butamax Advanced Biofuels LLC, Wilmington, DE (US)

(72) Inventors: Adam Bernfeld, Newark, DE (US); Keith H. Burlew, Middletown, DE (US); Anthony R. Calabria, Wilmington, DE (US); Duncan Coffey, Hockessin, DE (US); Benjamin Fuchs, Wilmington, DE (US); Ana Paula Goes, Barueri (BR); Adam David Henry, Kennett Square, PA (US); Walter Tamulis, San Diego, CA (US); Joseph J. Zaher, Newark, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 256 days.

(21) Appl. No.: 15/129,059

(22) PCT Filed: Apr. 10, 2015

(86) PCT No.: PCT/US2015/025256
§ 371 (c)(1),
(2) Date: Sep. 26, 2016

(87) PCT Pub. No.: WO2015/157607
PCT Pub. Date: Oct. 15, 2015

(65) Prior Publication Data
US 2017/0253846 A1    Sep. 7, 2017

Related U.S. Application Data

(60) Provisional application No. 61/978,410, filed on Apr. 11, 2014.

(51) Int. Cl.
*C12M 1/00*    (2006.01)
*B08B 9/08*    (2006.01)
(Continued)

(52) U.S. Cl.
CPC ............ *C12M 39/00* (2013.01); *A61L 2/04* (2013.01); *B01D 3/002* (2013.01); *B08B 9/08* (2013.01);
(Continued)

(58) Field of Classification Search
CPC ......... C12M 39/00; C12M 21/12; A61L 2/04; C12F 3/00; B01D 3/002; B08B 9/08; C11D 11/0041
See application file for complete search history.

(56) References Cited

U.S. PATENT DOCUMENTS

| 8,373,008 | B2 | 2/2013 | Grady et al. |
| 8,373,009 | B2 | 2/2013 | Grady et al. |

(Continued)

OTHER PUBLICATIONS

Bremer, et al., Laboratory scale Clean-In-Place (CIP) studies on the effectiveness of different caustic and acid wash steps on the removal of dairy biofilms, Intl. J. Food Microbiol. 106:254-262, 2006.

(Continued)

*Primary Examiner* — Regina M Yoo

(57) ABSTRACT

The present disclosure is directed to methods, approaches, devices, equipment, and systems for minimizing or reducing contamination in facilities implementing fermentation or distillation processes. In embodiments, the facility is a biofuel plant that produces fermentation product such as product alcohol like butanol. In some embodiments, the methods, approaches, devices, equipment, and systems are operable to implement clean in place contamination (CIP) mitigation techniques that can also include sterilize in place (SIP) mitigation techniques to decontaminate equipment including surfaces of the equipment that come in contact with materials used in the production of product alcohols. Other cleaning and contamination minimizing techniques are also described.

15 Claims, 10 Drawing Sheets

(51) Int. Cl.
*C11D 11/00* (2006.01)
*B01D 3/00* (2006.01)
*C12F 3/00* (2006.01)
*A61L 2/04* (2006.01)

(52) U.S. Cl.
CPC ............ *C11D 11/0041* (2013.01); *C12F 3/00* (2013.01); *C12M 21/12* (2013.01); *A61L 2202/17* (2013.01)

(56) References Cited

U.S. PATENT DOCUMENTS

| | | |
|---|---|---|
| 8,409,834 B2 | 4/2013 | Burlew et al. |
| 8,426,173 B2 | 4/2013 | Bramucci et al. |
| 8,426,174 B2 | 4/2013 | Bramucci et al. |
| 8,460,439 B2 | 6/2013 | Parten |
| 8,476,047 B2 | 7/2013 | Burlew et al. |
| 8,557,540 B2 | 10/2013 | Burlew et al. |
| 8,563,788 B2 | 10/2013 | Grady et al. |
| 8,569,552 B2 | 10/2013 | Grady et al. |
| 8,574,406 B2 | 11/2013 | Grady et al. |
| 8,617,861 B2 | 12/2013 | Grady et al. |
| 8,628,643 B2 | 1/2014 | Grady et al. |
| 8,697,404 B2 | 4/2014 | Anton et al. |
| 8,759,044 B2 | 6/2014 | DiCosimo et al. |
| 8,765,425 B2 | 7/2014 | DiCosimo et al. |
| 8,828,695 B2 | 9/2014 | Grady et al. |
| 8,865,443 B2 | 10/2014 | Burlew et al. |
| 8,906,204 B2 | 12/2014 | Xu |
| 8,968,522 B2 | 3/2015 | Xu et al. |
| 8,968,523 B2 | 3/2015 | Xu et al. |
| 8,969,050 B2 | 3/2015 | Austin et al. |
| 8,969,055 B2 | 3/2015 | Grady et al. |
| 9,012,190 B2 | 4/2015 | Dauner et al. |
| 9,040,263 B2 | 5/2015 | Anton et al. |
| 9,109,196 B2 | 8/2015 | Bazzana et al. |
| 9,156,760 B2 | 10/2015 | Zaher et al. |
| 9,175,315 B2 | 11/2015 | Anton et al. |
| 9,206,448 B2 | 12/2015 | Anton et al. |
| 9,249,076 B2 | 2/2016 | Anton et al. |
| 9,371,547 B2 | 6/2016 | Burlew et al. |
| 9,469,584 B2 | 10/2016 | Anton et al. |
| 9,517,985 B2 | 12/2016 | Basham et al. |
| 9,523,104 B2 | 12/2016 | Fuchs et al. |
| 9,605,281 B2 | 3/2017 | Bazzana et al. |
| 9,663,759 B2 | 5/2017 | Bhalla et al. |
| 9,670,511 B2 | 6/2017 | Roesch et al. |
| 9,682,908 B2 | 6/2017 | Zaher |
| 9,732,362 B2 | 8/2017 | Barr et al. |
| 9,771,602 B2 | 9/2017 | Anthony et al. |
| 9,809,520 B2 | 11/2017 | Cheng et al. |
| 9,962,623 B2 | 5/2018 | Zaher et al. |
| 2008/0274526 A1 | 11/2008 | Bramucci et al. |
| 2009/0305370 A1 | 12/2009 | Grady et al. |
| 2010/0143995 A1 | 6/2010 | Erdner-Tindall et al. |
| 2010/0279370 A1 | 11/2010 | Parten |
| 2011/0097773 A1 | 4/2011 | Grady et al. |
| 2011/0136193 A1 | 6/2011 | Grady et al. |
| 2011/0294179 A1 | 12/2011 | Grady et al. |
| 2011/0312053 A1 | 12/2011 | Burlew et al. |
| 2012/0015862 A1 | 1/2012 | Travis et al. |
| 2012/0156738 A1* | 6/2012 | Anton .................... B01D 3/002 435/135 |
| 2013/0164795 A1 | 6/2013 | Lowe et al. |
| 2013/0197279 A1 | 8/2013 | Wright |
| 2013/0217060 A1 | 8/2013 | Bramucci et al. |
| 2013/0224728 A1 | 8/2013 | Bramucci et al. |
| 2013/0252297 A1 | 9/2013 | Parten |
| 2013/0309738 A1* | 11/2013 | Barr ......................... C12P 7/16 435/160 |
| 2014/0018581 A1 | 1/2014 | Grady et al. |
| 2014/0024064 A1* | 1/2014 | Burlew ..................... C12P 7/16 435/29 |
| 2014/0073021 A1* | 3/2014 | Bazzana ................ C12M 21/12 435/134 |
| 2014/0073820 A1* | 3/2014 | Bazzana ................ C12M 21/12 568/913 |
| 2014/0093931 A1 | 4/2014 | Dauner et al. |
| 2014/0099688 A1 | 4/2014 | Grady et al. |
| 2014/0106419 A1 | 4/2014 | Bazzana et al. |
| 2014/0142352 A1 | 5/2014 | Dauner et al. |
| 2014/0162344 A1 | 6/2014 | DiCosimo et al. |
| 2014/0178529 A1 | 6/2014 | Anton et al. |
| 2014/0234929 A1 | 8/2014 | Barr et al. |
| 2014/0256020 A1 | 9/2014 | DiCosimo et al. |
| 2014/0363865 A1 | 12/2014 | Burlew et al. |
| 2015/0060259 A1 | 3/2015 | Xu |
| 2015/0080615 A1 | 3/2015 | Fergusson et al. |
| 2015/0191686 A1 | 7/2015 | Austin et al. |
| 2015/0211026 A1 | 7/2015 | Bazzana et al. |
| 2015/0218597 A1 | 8/2015 | Dauner et al. |
| 2015/0267225 A1 | 9/2015 | Bazzana et al. |
| 2016/0002131 A1 | 1/2016 | Glasspool et al. |
| 2017/0057894 A1 | 3/2017 | Basham et al. |
| 2017/0145445 A1 | 5/2017 | Bazzana et al. |
| 2017/0240930 A1 | 8/2017 | Roesch et al. |
| 2017/0298393 A1 | 10/2017 | Barr et al. |
| 2018/0016215 A1 | 1/2018 | Cheng et al. |

OTHER PUBLICATIONS

Fung, et al., Effect of phenolic antioxidants on microbial growth, Crit. Rev. Microbiol. 12:153-183, 1985 (Abstract only).
Yankah, et al., Quantitative Determination of Butylated Hydroxyanisole, Butylated Hydroxytoluene, and tert-Butyl Hydroquinone in Oils, Foods, and Biological Fluids by High-Performance Liquid Chromatography with Fluorometric Detection, Lipids 33: 1139-1145, 1998.
Guideline for Use of High Level Disinfectants & Sterilants for Reprocessing Flexible Gastrointestinal Endoscopes, Society of Gastroenterology Nurses and Associates, Inc., 2013.
Sterilization Techniques, Kirk-Othmer Encyclopedia of Chemical Technology, John Wiley & Sons, Inc., pp. 1-17, published online: Dec. 4, 2000.
Thakur, et al., Static Mixers in the Process Industries—A review, Trans IChemE 81(Part A):787-826, 2003.
Slunecka, Protecting Distillers Grains from Sulfur Buid-up, Ethanol Producer Magazine, published: May 4, 2009.
Quarini, Ice-pigging to reduce and remove fouling and to achieve clean-in-place, Appl. Thermal Eng. 22:747-753, 2002.
Monceaux, et al., Dryhouse technologies and DDGS production, Chapter 21, The Alcohol Textbook, 5th Edition, Lallemand Ethanol Technology and Nottingham University Press, 2009.
Junker, et al., A next generation, pilot-scale continuous sterilization system for fermentation media, Bioprocess Biosyst. Eng. 28:351-378, 2006.
International Search Report and Written Opinion for corresponding International Application No. PCT/US2015/025256, dated Aug. 4, 2015.

* cited by examiner

CONTAMINATION MITIGATION

CROSS REFERENCE TO RELATED APPLICATION

This application claims benefit of priority from U.S. Provisional Application No. 61/978,410, filed Apr. 11, 2014, which is hereby incorporated by reference in its entirety.

FIELD

The present disclosure generally relates to methods, systems, techniques, and approaches for mitigating contamination in alcohol production, such as in fermentation and distillation processes for biofuel production.

BACKGROUND

Fermentation and distillation are commercially important processes worldwide. In the United States over 100 commercial facilities produce biofuels, such as ethanol, from a variety of renewable sources. Butanol, a four carbon chain alcohol, includes 1-butanol, 2-butanol, and isobutanol all of which can be produced via fermentation. Butanol can be generated from renewable sources such as corn, sugar cane, cellulosic sources, as well as, other biomass. Butanol production, like ethanol production, implements fermentation and distillation processes to generate and concentrate the butanol for use in a variety of applications.

Butanol, for example, can be implemented as a fuel additive, a blend component to diesel fuel, a chemical reagent in the plastics industry, solvent, and a food grade extractant in the food and flavor industry. Butanol is favored as a fuel or fuel additive because it has a higher energy density than ethanol and yields $CO_2$ and little or no $SO_X$ or $NO_X$ when used in an internal combustion engine. Additionally, butanol is less corrosive than ethanol. As the demand for butanol increases, interest in producing butanol from renewable resources such as corn, sugar cane, or cellulosic materials by fermentation is expanding.

Fermentation uses microorganisms to generate alcohol from biomass, e.g., renewable feed stocks. For example, yeast is used to convert sugars derived from corn into ethanol. Bio-derived alcohols, e.g., ethanol, butanol, produced by the fermentation are environmentally friendly as the starting materials are obtained from biological sources that can be renewed on a regular basis. Alcohols produced by fermentation can displace alcohols obtained from non-renewable sources such as oil.

Fermentation and distillation processes may be susceptible to contamination. Contaminants in a fermentation processes can diminish the microorganisms' effectiveness or reduce the population of microorganism, e.g., "kill off" microorganisms rendering them biologically inactive and thereby resulting in yield loss, lost production, and at times aborted batches. All of these can reduce the efficiency of facility and lead to waste.

Practices for cleaning fermentation and distillation facilities can be problematic and/or expensive as steam or chemicals are used. Steam, although effective, is expensive and often requires retrofitting a facility's steam generation system. Alkalines and/or acids may not be as effective for cleaning equipment in comparison to steam. Further, alkaline and acid cleaning agents may additionally pose a disposal issue.

SUMMARY

The present disclosure is directed to methods, approaches, devices, equipment, and systems for minimizing or reducing contamination in facilities implementing fermentation or distillation processes. In embodiments, the facility is a biofuel plant that produces fermentation product such as product alcohol like butanol for use in fuel. In some embodiments, the methods, approaches, devices, equipment, and systems are operable to implement clean in place contamination (CIP) mitigation techniques that can include sterilize in place (SIP) procedures to decontaminate equipment including surfaces of the equipment that come in contact with materials used in the production of product alcohols. Other cleaning and contamination minimizing techniques are also described. Although the decontamination, cleaning, and sterilization techniques described herein can be used to decontaminate a wide variety of contaminants including fermentation solids, impurities, and so forth, in embodiments, these techniques are implemented to decontaminate contaminants that compete with microorganisms that produce fermentation product (e.g., a product alcohol) and/or microorganisms that produce or are associated with a contaminant, such as an impurity, that inhibits the microorganism. For example, some bacteria produce lactic acid that inhibits butanologens (butanol producing microorganisms). The bacteria that produce lactic acid compete for the fermentable carbon substrate that would otherwise be available to the butanolgen for butanol production. Additionally, the impurity, e.g., lactic acid, may inhibit butanol production by causing butanologens to slow down butanol production or it may be sufficiently toxic to render the butanologen biologically inactive.

The present disclosure is directed to a method for decontaminating equipment used in at least one of a fermentation or distillation process by separating at least one of an off-specification product or lights purge material (e.g., a by-product of fermentation) from a stream of distillation product that is capable of being subject to contamination from at least one of a distillation process or a fermentation process associated with the distillation process; or separating at least one process solvent stream from a distillation process or fermentation process; and cleaning the equipment with a solution comprising the at least one of off-specification product or lights purge material to minimize contamination associated with the distillation product. In some embodiments, the solution is obtained from the stream of distillation product.

In embodiments, the method further comprises reiterating the cleaning until the equipment reaches an acceptable level of cleanliness, for example, the acceptable level of cleanliness substantially maintains a ratio of fermentation co-products. In embodiments, the contamination comprises a microorganism that produces a co-product and the method is implemented to maintain production of a minor co-product substantially at or below the ratio. In some embodiments, the method includes incorporating at least a portion of the solution with fermentation product that results from the fermentation process until a distillation column associated with the distillation process achieves steady state production of distillation product that meets specification.

In some embodiments, the solution is implemented at a concentration that is effective to decontaminate the equipment, but is insufficient to appreciably inhibit a butanologen used in the fermentation process. In some embodiments, the solution comprises one or more of ethanol, butanol, acetic acid, isobutyric acid, isoamyl alcohol. In some embodiments, the solution comprises distillation product. In embodiments, the contaminant is associated with production of at least one of acetic or lactic acid.

In some embodiments, the solution comprises butanol. In some embodiments, the butanol concentration in the solution is greater than the butanol concentration in the fermentation product but is less than the concentration of butanol that meets specification. In some embodiments, the solution comprises at least one of up to approximately fifty percent (50%) butanol by weight, up to approximately thirty percent (30%) ethanol by weight, up to approximately twenty percent (20%) isobutyric acid by weight, up to approximately twenty percent (20%) acetic acid by weight, or any combination thereof. In some embodiments, the solution comprises approximately ten percent (10%) by weight butanol and approximately seven percent (7%) ethanol. In some embodiments, the solution is implemented in a terminal sterilization process.

In some embodiments, cleaning implements at least one of spray ball washing, impingement washing, or vessel soaking. In some embodiments, the method includes recycling at least a portion of the solution that has been used for cleaning for distillation into distillation product. In some embodiments, at least a portion of the solution is permitted to remain on the equipment until the equipment is used for subsequent production.

In some embodiments, the equipment comprises fermentation equipment. In some embodiments, fermentation equipment comprises a fermentor. In some embodiments, cleaning the equipment comprises at least one of a cleaning in place (CIP) procedure or a sterilizing in place (SIP) procedure. In some embodiments, the solution is implemented in a terminal sterilization process. In embodiments, the CIP and SIP procedures implement the solution and another solution that includes a different concentration of the at least one of the off-specification product, a heavies purge material, or a lights purge material. In some embodiments, the solution contains a sufficient concentration of off-specification product, heavies purge material, lights purge material, or a combination thereof to decontaminate equipment, but is of sufficiently low concentration to minimize flammability of the solution to less than that of the distillation product.

In some embodiments, cleaning comprises one or more of: (A) performing a clean in place (CIP) procedure that comprises at least one of spray ball washing, impingement washing, or vessel soaking and subsequently performing a sterilization in place (SIP) procedure; (B) performing a CIP procedure without performing a SIP procedure; (C) performing a wash with water and subsequently performing a SIP procedure; (D) performing a wash with water and immersing the at least a portion of the equipment as part of a SIP procedure; or combinations thereof including repeating at least one of A, B, C, or D until the equipment reaches an acceptable level of cleanliness. In some embodiments, the solution comprises a mix of distillation co-products that are separated from the stream of distillation product in a common purge stream. In embodiments, the method further comprises sending at least a portion of the solution used for cleaning for combustion to produce energy for at least one of the fermentation or distillation process.

The present disclosure is also directed to a method for decontaminating equipment used to produce butanol comprising: generating a solution for cleaning equipment used to produce butanol from at least one of an off-specification butanol or a lights purge material that results from distillation of butanol produced by a fermentation, the solution comprising butanol or lights purge material at a sufficiently high concentration to minimize or eliminate contamination, but is insufficient to appreciably inhibit a recombinant microorganism (e.g., a butanologen) used in the fermentation; and cleaning at least a portion of the equipment with the solution to minimize contamination that results from production of the butanol. In some embodiments, production of butanol comprises at least one of a fermentation process or a distillation process. In some embodiments, contamination comprises microbial contamination.

In some embodiments, off specification butanol, and one or more of lights purge material or heavies purge material are obtained from a common purge stream.

In some embodiments, the equipment comprises distillation equipment. In some embodiments, distillation equipment comprises a distillation column.

In some embodiments, the concentration of butanol in the solution is greater than a concentration of butanol in fermentation broth. In some embodiments, the concentration of the butanol is the solution is less than the concentration of the off-specification butanol. In some embodiments, butanol comprises isobutanol. In some embodiments, the solution comprises ethanol. In some embodiments, the solution comprises one or more organic acids at a concentration higher than that of the fermentation broth. Example organic acids include, but are not limited to isobutyric acid or acetic acid.

In some embodiments, the solution comprises at least one of up to approximately fifty percent (50%) butanol by weight, up to approximately thirty percent (30%) ethanol by weight, up to approximately twenty percent (20%) isobutyric acid by weight, up to approximately twenty percent (20%) acetic acid by weight, or any combination thereof. In some embodiments, the solution comprises approximately ten percent (10%) by weight butanol and approximately seven percent (7%) ethanol.

In some embodiments, the method further comprises recycling butanol used in the cleaning into butanol that meets specification. In some embodiments, the method further comprises combusting the solution used for cleaning to provide energy for the production of butanol.

In some embodiments, the method further comprises incorporating solution with butanol that has been extracted from a fermentation broth until a distillation column reaches steady state production of butanol that meets specification.

In some embodiments, cleaning the equipment comprises at least one of a cleaning in place (CIP) procedure or a sterilizing in place (SIP) procedure. In some embodiments, the equipment does not include all equipment used to produce butanol.

The present disclosure is also directed to a fermentation system for producing butanol comprising: one or more vessels configured to ferment butanol; and a cleaning system configured to provide a solution that comprises at least one of an off specification product (e.g., butanol) or a lights purge material obtained from a distillation system associated with the fermentation system or a process solvent stream from the fermentation system or the distillation system for cleaning at least a portion of the fermentation system or the distillation system. In some embodiments, the fermentation system is configured to substantially continuously produce butanol.

In some embodiments, the off specification product comprises butanol. In some embodiments, the butanol is isobutanol.

In embodiments, the cleaning system is coupled to the fermentation system, wherein butanol from the solution utilized by the cleaning system is recycled with butanol produced by the fermentation system to be distilled by the distillation system. In some embodiments, at least one of off specification product (e.g., butanol) or the lights purge material is produced by the fermentation system. In some embodiments, the cleaning system is configured to implement one or more of spray ball washing, impingement washing, or vessel soaking to clean the one or more vessels.

In embodiments, the cleaning system is configured to utilize solution that has greater toxicity (e.g., higher concentration of butanol and/or isobutyric acid) than is included in a fermentation broth generated as part of fermenting butanol. In some embodiments, the solution comprises at least one of up to approximately fifty percent (50%) butanol by weight, up to approximately thirty percent (30%) ethanol by weight, up to approximately twenty percent (20%) isobutyric acid by weight, or up to approximately twenty percent (20%) acetic acid by weight.

In some embodiments, the cleaning system is configured to conduct a cleaning in place (CIP) procedure or a sterilizing in place (SIP) procedure of the one or more vessels. In some embodiments, the cleaning system is configured to conduct different combinations of CIP and SIP procedures that include repeating CIP and SIP procedures so the one or more vessels reach an acceptable level of cleanliness. In some embodiments, the fermentation system is further configured to direct butanol used to clean the one or more vessels for combustion to produce energy for one or more of the fermentation or distillation systems.

In some embodiments, the cleaning system comprises a storage vessel for the solution that is configured to be in fluid communication with one or more of a propagation vessel, a product vessel, or a destination vessel. In some embodiments, the storage vessel is further configured to be in fluid communication with a lights column included in the distillation system. In some embodiments, the storage vessel is further configured to be in fluid communication with a purge stream of butanol that is off specification.

In some embodiments, the cleaning system is configured to leave solution on a surface of the one or more vessel until utilized for fermentation. In some embodiments, the fermentation system is further configured to recycle lean fermentation broth for use in a subsequent fermentation. In some embodiments, the cleaning system is configured to provide solution that includes one or more of ethanol or butanol at a concentration that is insufficient to appreciably inhibit a recombinant microorganism utilized by the fermentation system to produce butanol.

In some embodiments, the composition of the solution is selected to maintain a ratio of co-products produced by the fermentation system. In some embodiments, the cleaning system is configured to minimize ethanologens in the fermentation system, so the fermentation system produces butanol and ethanol substantially at a predetermined ratio. In some embodiments, the cleaning system is configured to minimize microorganisms associated with acetic acid production in the fermentation system. In some embodiments, the cleaning system is further configured to substantially eliminate the microorganisms from the fermentation system.

The present disclosure is also directed to a cleaning system configured for use with a facility for continuously producing product alcohol through use of a recombinant microorganism, comprising: a vessel configured to be placed in fluid connection with a purge stream to remove material that is not to be included in product alcohol, the vessel being additionally configured to be placed in fluid connection with equipment included in the facility and operable to clean the equipment to minimize contamination with the material substantially at a predetermined temperature. In some embodiments, the cleaning system further comprises a heater configured to heat the material substantially to the predetermined temperature. In embodiments, the equipment does not comprise all equipment used to produce alcohol from a renewable feedstock. In some embodiments, the recombinant microorganism is a butanologen. In some embodiments, the equipment is configured to produce isobutanol.

In embodiments, the cleaning system is configured to conduct one or more cleaning procedures based on a factor associated with the equipment. In some embodiments, the one or more cleaning procedures comprises at least one of: (A) performing a clean in place (CIP) procedure that comprises at least one of spray ball washing, impingement washing, or vessel soaking and subsequently performing a sterilization in place (SIP) procedure; (B) performing a CIP procedure without performing a SIP procedure; (C) performing a wash with water and subsequently performing a SIP procedure; (D) performing a wash with water and immersing the at least a portion of the equipment as part of a SIP procedure; and combinations thereof including repeating at least one of A, B, C, or D until the at least the portion of the equipment reaches an acceptable level of cleanliness. In embodiments, the factor comprises at least one of a ratio of ethanol produced, occurrence of a rejected batch, acetic acid production, or reduced product alcohol production.

In some embodiments, the purge stream includes material that is of sufficient concentration to minimize microbial growth associated with the equipment. In some embodiments, the material is insufficient to inhibit a recombinant microorganism from producing the alcohol. In some embodiments, one or more of the equipment or the cleaning system are configured to leave a residue of the material on a surface of the equipment.

In some embodiments, the system further comprises a heater for heating the material to increase the efficacy of the material to clean the equipment. In some embodiments, at least one of the cleaning system or the equipment is further configured to direct the material used to clean the equipment for combustion to produce energy for the facility.

In some embodiments, the cleaning system is configured to provide material that is of a higher concentration than a concentration of the material in a fermentation broth used to generate the product alcohol. In some embodiments, the material comprises one or more of alcohol or a co-product of the product alcohol. In some embodiments, the product alcohol comprises at least one of 1-butanol, 2-butanol, tert-butanol, or isobutanol. In some embodiments, the cleaning system is further configured to incorporate at least a portion of the material with fermentation product used to generate product alcohol until steady state production of the product alcohol is achieved.

The present disclosure is also directed to a method for partially decontaminating a fermentation system configured to perform substantially continuous fermentation comprising: isolating an in situ product recovery (ISPR) portion of a fermentation system from equipment used to generate fermentation product from feedstock material; introducing caustic solution, subsequent to rinsing the ISPR portion with water, upstream from a point at which extractant used for ISPR is introduced; and introducing an acidic solution downstream from the point at which extractant is introduced, wherein introduction of the acidic solution is performed such that at least a portion of the acidic solution remains on a surface of the equipment included in the ISPR portion. In some embodiments, rinsing is performed. In some embodiments, the caustic solution, at least a portion of the acidic solution, and any water used for rinsing is drained from the ISPR portion without the use of equipment configured to recycle lean fermentation broth to the equipment used to generate the fermentation product. In some embodiments, at least a portion of the acidic solution that remains on a surface of equipment included in the ISPR portion is permitted to recycle with the lean fermentation broth to the equipment used to generate the fermentation product. In some embodiments, the method further comprises rinsing equipment in the ISPR portion with water between introducing the caustic solution and acidic solution. In some embodiments, the extractant comprises corn oil fatty acid (COFA).

In embodiments, the acidic solution comprises approximately two percent (2%) sulfamic acid by weight. In other embodiments, the acidic solution comprises approximately two percent (2%) sulfuric or approximately two percent (2%) phosphoric acid by weight. In embodiments, the caustic solution comprises approximately two percent (2%) sodium hydroxide by weight.

In some embodiments, introducing a caustic solution comprises rinsing a surface of equipment in the ISPR portion with the caustic solution. In embodiments, introducing an acidic solution comprises rinsing a surface of equipment in the ISPR portion with the acidic solution. In some embodiments, caustic solution is drained from equipment included in the ISPR portion without use of a pump configured to pump lean fermentation broth for reuse in fermenting fermentation product. In some embodiments, fermentation product comprises isobutanol.

This disclosure is also directed to a method for decontaminating an in situ product recovery (ISPR) system for a fermentation process comprising: preparing a cleaning solution by mixing the cleaning solution in a first portion of an ISPR system; transferring at least a portion of the cleaning solution to a second portion of the fermentation system to decontaminate the second portion to a level of decontamination that is suitable to minimize contamination by a microorganism that inhibits or competes with production of fermentation product that results from the fermentation process. In some embodiments, the first portion comprises a settler. In some embodiments, the method is conducted in a manner to minimize introduction of extractant into a fermentation broth through recycling of broth from which the fermentation product has been removed into a settler for use in producing additional fermentation product. In some embodiments, the fermentation product comprises butanol.

In some embodiments, the fermentation process comprises use of a fatty acid extractant. In some embodiments, extractant comprises corn oil fatty acid (COFA).

In some embodiments, the method is implemented in conjunction with at least one other method for decontaminating the fermentation system or a system related to the fermentation system and the extractant is substantially isolated from other portions of the fermentation system not in the ISPR system. In some embodiments, transferring comprises transferring the cleaning solution from a first settler to a second settler.

In some embodiments, the cleaning solution does not substantially cause extractant to undergo a saponification reaction or the method further comprises performing an acidic rinse to remove saponified material from at least a portion of the ISPR system. In some embodiments, the method further comprises: deinventoring at least one of a mixer or a settler in the fermentation system, and transferring comprises: rinsing the at least one mixer or settler with water where at least a portion of the water is introduced upstream of a point at which extractant is added to the ISPR system; cleaning the at least one mixer or settler with a caustic solution to minimize contamination by a microorganism that does not produce the fermentation product; and cleaning the at least one mixer or settler with an acidic solution to substantially remove any saponified material that results from cleaning with the caustic solution.

In some embodiments, the caustic solution comprises alkaline solution. In some embodiments, the caustic solution comprises sodium hydroxide solution. In some embodiments, the acidic solution comprises sulfamic acid solution. In some embodiments, the rinsing occurs between the cleaning with caustic solution and cleaning with acidic solution. In some embodiments, rinsing is repeated more than once.

This disclosure is also directed to a method for decontaminating an in situ product removal (ISPR) system included in a fermentation system that is configured to produce fermentation product, comprising: introducing extractant to the ISPR system as part of a decontamination procedure wherein the extractant is maintained in at least a portion of the ISPR system at a temperature that is higher than a temperature at which extractant is implemented by the ISPR system to remove fermentation product from a fermentation broth during use of the ISPR system; sterilizing equipment included in the ISPR system by maintaining the extractant at a sufficiently high temperature to ensure surfaces of the equipment that contact fermentation broth during use are substantially free of microorganisms that compete with or inhibit a recombinant microorganism that produces fermentation product. In some embodiments, extractant is maintained at a temperature that is sufficiently high to ensure the extractant is sterile of microorganisms that compete with or inhibit a recombinant microorganism that produces fermentation product. In some embodiments, the method further comprises bypassing or ceasing operation of a cooler included in the ISPR system to raise the temperature of the extractant. In some embodiments, introducing extractant comprises pumping extractant at a rate to maintain the surfaces at the sufficiently high temperature. In some embodiments, the sufficiently high temperature is equal to or greater than seventy-five degrees Celsius (75° C.).

In some embodiments, the sufficiently high temperature is insufficient to cause appreciable thermal degradation of the extractant. In some embodiments, the extractant comprises corn oil fatty acid (COFA).

In some embodiments, the method further comprises deinventoring the equipment by draining the equipment of any fermentation broth and/or extractant using a port that is not used to return lean fermentation broth to a vessel included in fermentation system in which fermentation product is produced from a renewable feedstock. In some embodiments, the equipment comprises a settler or mixer. In some embodiments, the microorganisms that compete with or inhibit a recombinant microorganism that produces fermentation product comprises bacteria or wild-type yeast. In some embodiments, the method implements more than one fermentation process to provide continuous fermentation product production.

In some embodiments, a method for decontaminating an in situ product recovery (ISPR) system for a fermentation process comprises: deinventoring a mixer or a settler included in a fermentation system; introducing ISPR material into the mixer or settler to substantially maintain a predetermined temperature; deinventoring the mixer or settler through a low point drain included therein to permit startup of the mixer or settler for use in recovering fermentation product from fermentation broth. In some embodiments, the low point drain is not configured for removing lean fermentation broth that results from extraction of fermentation product from the broth, from the at least one mixer or settler. In some embodiments, introducing ISPR material comprises substantially matching a feed rate of the ISPR material to a pump rate for a pump that provides the ISPR material to the mixer or settler. In some embodiments, the method further comprises rinsing the mixer or settler with water, which is provided upstream of a point at which the ISPR material is added to the ISPR system.

In some embodiments, the predetermined temperature is approximately seventy five degrees Celsius (75° C.). In some embodiments, the ISPR material, prior to introduction to the mixer or settler, is maintained at a temperature that is sufficiently high enough to be unfavorable to growth of a microorganism that competes with production of fermentation product. In some embodiments, the method further comprises at least one of reducing or terminating use of a cooler that is operable to cool the ISPR material during use of the ISPR system.

In some embodiments, introducing ISPR material occurs by feeding the ISPR material through an inlet used to introduce ISPR material to the at least one mixer or settler during use of the ISPR system to separate fermentation product from the fermentation broth during non-decontamination use of the ISPR system. In some embodiments, the extractant comprises lean extractant.

This disclosure is also directed to a system for in situ product removal (ISPR) of a fermentation product from substantially a continuous fermentation system comprising: an ISPR system configured to be isolated during a cleaning procedure from a source of fermentation broth that includes fermentation product that the ISPR is configured to extract from the broth and recycle lean broth with a lower concentration of fermentation product than the fermentation broth back to the source of the fermentation broth. In embodiments, the ISPR system is further configured to drain cleaning solution from equipment included in the ISPR portion without using a pump that is configured to recycle lean fermentation broth to the fermentation source. In some embodiments, the ISPR system is further configured to introduce cleaning solution upstream from a point at which extractant is introduced to the ISPR system. In some embodiments, the ISPR system is further configured to transfer cleaning solution from one portion of the ISPR system to another portion of the ISPR system as part of a cleaning procedure. In some embodiments, the ISPR system is configured to rinse equipment included in the ISPR system by introducing water upstream from a point at which extractant is configured to be introduced to the ISPR system. In some embodiments, the ISPR system comprises an agitator configured to agitate cleaning solution during a cleaning procedure. In some embodiments, the ISPR system comprises equipment including vessels and pipes.

In some embodiments, the cleaning solution comprises one or more of caustic solution or acidic solution. In some embodiments, the system is configured to implement an alkaline cleaning solution. In some embodiments, the caustic solution comprises sodium hydroxide solution and the acidic solution comprises sulfamic acid solution. In some embodiments, the sodium hydroxide solution is approximately two percent (2%) sodium hydroxide by weight and the sulfamic acid solution is approximately two percent (2%) sulfamic acid by weight. In some embodiments, the caustic solution is approximately two percent (2%) caustic material by weight and the acidic solution is approximately two percent (2%) acid material by weight.

The present disclosure is additional directed to a fermentation system for generating fermentation product comprising: an in situ product removal (ISPR) system configure to extract fermentation product from fermentation broth, for distillation to form a product alcohol, and return lean fermentation broth for use in generating additional fermentation product, the ISPR being additionally configured to isolate equipment in the ISPR system to decontaminate the equipment by introducing extractant to the equipment at a sufficiently high temperature to clean the equipment to an acceptable level of cleanliness of contaminants that compete with or inhibit production of fermentation product in the fermentation broth. In some embodiments, extractant comprises lean extractant that is capable of extracting product alcohol from fermentation broth.

In some embodiments, the system further comprises a cooler configured to reduce extractant temperature during use of the ISPR system to extract product alcohol from fermentation broth. In some embodiments, the ISPR system is configured to cease operation of the cooler during decontamination to increase the temperature of the extractant to the sufficiently high temperature. In some embodiments, the high temperature is sufficient to minimize microorganism contaminants that compete with production of the fermentation product. In some embodiments, the ISPR system is configured to maintain the extractant in contact with the equipment for a sufficiently long residence time to effectively minimize the microorganism contaminants to the acceptable level of cleanliness. In some embodiments, the sufficiently high temperature is below a temperature that would cause appreciable thermal degradation of the extractant.

In some embodiments, the extractant comprises corn oil fatty acid (COFA). In some embodiments, the fermentation product comprises butanol. In some embodiments, the fermentation product comprises one or more of 1-butanol, 2-butanol, tert-butanol, or isobutanol. In some embodiments, the contaminant comprises a bacteria or a wild-type yeast. In embodiments, the contaminant is associated with a co-product of the fermentation product. In some embodiments, the co-product comprises a co-product that is produced at a rate that is significantly less than production of the fermentation product. In some embodiments, the acceptable level of cleanliness comprises substantially eliminating effectively all the contaminant from the equipment.

In some embodiments, the system further comprises an extractant pump configured to circulate extractant in the equipment, the extractant pump being further configured to pump extractant through the equipment at a rate sufficient to effectively maintain the sufficiently high temperature in the equipment. In some embodiments, the system during decontamination is insufficient to raise the temperature of the equipment to the sufficiently high temperature, but is sufficient to effectively raise surfaces of the equipment capable of coming in contact with the extractant to the sufficiently high temperature. In some embodiments, the sufficiently high temperature is approximately equal to or greater than seventy-five degrees Celsius (75° C.). In some embodiments, the sufficiently high temperature is approximately eighty degrees Celsius (80° C.). In some embodiments, the ISPR system is further configured to substantially maintain the extractant at approximately eighty degrees Celsius (80° C.) when not in use for decontaminating the equipment.

In some embodiments, at least one of the ISPR system or the fermentation system is configured to permit extractant used for decontamination to be drained out a port that is not used to return the lean fermentation broth for use in generating additional fermentation product. In some embodiments, at least one of the ISPR system or the fermentation system is configured to permit extractant used for decontamination to be drained out a port included in at least one of a settler or mixer included in the fermentation system.

This disclosure is additionally directed to a method for reducing contamination in fermentation feedstock comprising: heating, for a sufficiently long residence time, a thin mash formed from biomass at a sufficiently high temperature to minimize to an acceptable level contaminant microorganisms in the thin mash, the contaminant microorganisms if not minimized would appreciably compete with microorganisms configured to convert fermentable carbon substrate obtained from the biomass into product alcohol by fermentation; and incorporating with the thin mash the microorganisms that are configured to convert fermentable carbon substrate into product alcohol. In some embodiments, the contaminant microorganisms comprise at least one of wild-type yeast or bacteria.

In some embodiments, the method further comprises separating oil from a remainder of the biomass to form the thin mash. In some embodiments, separating further comprises separating biomass solids from mash to form the thin mash. In some embodiments, biomass comprises at least one of corn grain, corn cobs, crop residues, corn husks, corn stover, grasses, wheat, rye, wheat straw, barley, barley straw, hay, rice straw, switchgrass, waste paper, sugar cane bagasse, sorghum, sugar cane, soy, grains, cellulosic material, lignocellulosic material, trees, branches, roots, leaves, wood chips, sawdust, shrubs and bushes, vegetables, fruits, flowers, animal manure, or combinations thereof.

In some embodiments, heating is performed as part of a continuous process. In some embodiments, the residence time and sufficiently high temperature are selected to effectively sterilize the thin mash. In some embodiments, the contaminant microorganism is capable of generating a co-product from the thin mash and sterilization eliminates the contaminant microorganisms to an acceptable level of co-product production in fermentation of the recombinant microorganism. In some embodiments, the acceptable level of co-product results in the production of a de minimis amount of co-product in the fermentation.

In some embodiments, the heating is performed as part of a propagation procedure. In some embodiments, the heating comprises heating the thin mash at substantially one hundred twenty-one degrees Celsius (121° C.). In some embodiments, heating is performed after oil is separated from the biomass to form the thin mash. In some embodiments, heating comprises maintaining the temperature of the thin mash at substantially one hundred twenty-one degrees Celsius (121° C.) for approximately 15 minutes. In some embodiments, heating is performed after oil is separated from a remainder of the biomass to form the thin mash. In some embodiments, the method further comprises heating mash comprising the thin mash and biomass solids at a temperature between approximately one hundred five degrees to one hundred twenty-six degrees Celsius (105°-126° C.). In some embodiments, heating the mash comprises maintaining the between approximately one hundred five degrees to one hundred twenty-six degrees Celsius (105°-126° C.) temperature for between approximately five (5) to ten (10) minutes. In some embodiments, heating the mash is insufficient to raise the temperature of the mash to between approximately one hundred five degrees to one hundred twenty-six degrees Celsius (105°-126° C.). In some embodiments, heating the mash is insufficient to appreciably reduce contaminant microorganisms from the mash.

In some embodiments, fermentable carbon substrate comprises at least one of monosaccharides, oligosaccharides, polysaccharides, glucose, sucrose, fructose, or combinations thereof. In some embodiments, the recombinant microorganisms configured to convert fermentable carbon substrate into a product alcohol comprise recombinant microorganisms configured to produce butanol. In some embodiments, butanol comprises isobutanol. In some embodiments, butanol comprises 1-butanol, 2-butanol, tert-butanol, isobutanol, or combinations thereof. In some embodiments, contaminant microorganisms comprise a bacterium contaminant or wild-type yeast.

In some embodiments, the acceptable level of contaminant microorganisms is a de minimis level of contaminant microorganisms in comparison to the microorganisms configured to convert biomass into a product alcohol. In some embodiments, the acceptable level of contaminant microorganisms comprises at least one of at or above eighty percent (80%) free; at or above ninety percent (90%) free, at or above ninety-five percent (95%), or at or substantially free of contaminant microorganisms.

In some embodiments, the method further comprises treating the biomass with enzyme capable of aiding in conversion of biomass to fermentable carbon substrate. In embodiments, treatment comprises treatment with lipase prior to the heating. In some embodiments, treatment further comprises heating the biomass to deactivate enzyme used to treat the biomass. In some embodiments, heating the biomass comprises heating to approximately eighty-five degrees Celsius (85° C.) to deactivate the enzyme. In some embodiments, the method is performed as part of propagating recombinant microorganisms that are configured to convert fermentable carbon substrate into product alcohol prior to fermentation.

This disclosure is additionally directed to a method for controlling co-product production in a fermentation process comprising: separating at least one of oil or solids from biomass that comprises a feedstock, the biomass being heated as part of converting biomass to fermentable carbon substrate for consumption by recombinant microorganisms to produce fermentation product; and heating thin mash to a sufficiently high temperature and for sufficient duration to minimize contamination to an acceptable level, the thin mash comprising the fermentable carbon substrate with oil and solids from the biomass removed. In some embodiments, the method further comprises incorporating the microorganisms with the thin mash.

In some embodiments, separation comprises utilizing a centrifuge to separate the thin mash from the oil and biomass solids. In some embodiments, biomass comprises at least one of corn grain, corn cobs, crop residues, corn husks, corn stover, grasses, wheat, rye, wheat straw, barley, barley straw, hay, rice straw, switchgrass, waste paper, sugar cane bagasse, sorghum, sugar cane, soy, grains, cellulosic material, lignocellulosic material, trees, branches, roots, leaves, wood chips, sawdust, shrubs and bushes, vegetables, fruits, flowers, animal manure, or combinations thereof. In some embodiments, fermentable carbon substrate comprises at least one of monosaccharides, oligosaccharides, polysaccharides, glucose, sucrose, fructose, or combinations thereof.

In some embodiments, heating as part of converting biomass to fermentable carbon substrate comprises heating at a temperature between approximately one hundred five degrees to one hundred twenty-six degrees Celsius (105°-126° C.). In some embodiments, heating as part of converting biomass to fermentable carbon substrate comprises maintaining the between approximately one hundred five degrees to one hundred twenty-six degrees Celsius (105°-126° C.) for between approximately five (5) to ten (10)

minutes. In some embodiments, heating as part of converting biomass to fermentable carbon substrate is insufficient to raise the biomass' temperature to approximately one hundred twenty-one degrees Celsius (121° C.). In some embodiments, heating as part of converting biomass to a fermentable carbon substrate comprises heating to approximately eighty-five degrees Celsius (85° C.) to deactivate an enzyme used in the converting. In some embodiments, heating thin mash comprises heating the thin mash at one hundred twenty-one degrees Celsius (121° C.). In some embodiments, heating thin mash comprises maintaining the temperature of the thin mash at substantially one hundred twenty-one degrees Celsius (121° C.) temperature for approximately 15 minutes.

In some embodiments, the contamination is capable competing with the microorganism to consume the fermentable carbon substrate. In some embodiments, the contamination is associated with production of at least one of acetic or lactic acid. In some embodiments, the acceptable level of contamination comprises a level at which production of a fermentation co-product from the fermentable carbon substrate meets or is less than a predetermined ratio. In some embodiments, the acceptable level comprises substantially eliminating contaminants from the thin mash.

This disclosure is also directed to a method for minimizing contamination in a fermentation feedstock comprising: heating mash comprising biomass and water to convert biomass to fermentable carbon substrate suitable for consumption by a microorganism to produce a product alcohol in a fermentation process; heating the mash to deactivate an enzyme added to the mash to aid in conversion of the biomass to fermentable carbon substrate; and heating thin mash comprising fermentable carbon substrate, with biomass solid and oil from the biomass removed, to a sufficiently high temperature for a sufficient duration to minimize contaminant microorganisms that are capable of consuming fermentable carbon substrate or inhibiting the microorganism from producing product alcohol, the heating the mash and the heating the mash to deactivate enzyme being of insufficient temperature and/or time to effectively minimize contaminant microorganisms from the mash. In some embodiments, heating mash comprises heating at a temperature between approximately one hundred five degrees to one hundred twenty-six degrees Celsius (105°-126° C.). In some embodiments, heating mash comprises maintaining the between approximately one hundred five degrees to one hundred twenty-six degrees Celsius (105°-126° C.) temperature for between approximately five (5) to ten (10) minutes. In some embodiments, heating thin mash comprises maintaining the temperature of the thin mash at substantially one hundred twenty-one degrees Celsius (121° C. for approximately 15 minutes. In some embodiments, heating the mash to deactivate enzyme comprises heating the mash to approximately eighty-five degrees Celsius (85° C.).

In some embodiments, the recombinant microorganisms comprise butanologens. In some embodiments, the butanologen is configured to produce isobutanol. In some embodiments, the contaminant microorganisms comprise ethanologens. In some embodiments, contaminant microorganisms comprise organisms associated with fermentation of acetic acid or lactic acid. In embodiments, minimization of contaminant microorganisms comprises eliminating contaminant microorganisms to an acceptable level of contamination. In some embodiments, the acceptable level of contamination comprises eliminating substantially all the contaminant microorganisms in the thin mash. In some embodiments, heating the thin mash comprises heating the thin mash to a sufficient temperature.

This disclosure is also directed to a method of decontaminating a static mixer in an in situ product recovery (ISPR) system comprising: deinventoring the mixer from use by removing one or more of fermentation broth and extractant that remained in the mixer after use; generating at least one of frozen extractant or a slush that includes extractant generated from biomass; optionally, rinsing the interior of the mixer with a water rinse; and flowing the at least one of frozen extractant or slush through the mixer to remove a contaminant due to mechanical interaction of the at least one of frozen extractant or slush contacting an interior surface of mixer that contains the contaminant. In some embodiments, flowing comprises flowing the at least one of frozen extractant or slush in a direction opposite a direction through which liquid flows in normal operation of the static mixer. In some embodiments, the method further comprises removing the at least one of frozen extractant or slush by permitting the extractant or slush to melt. In embodiments, the method further comprises rinsing an interior surface of the static mixer with water after flowing the at least one of frozen COFA or slush. In some embodiments, the method further comprises introducing the at least one of frozen COFA or slush as a bolus to the static mixer.

The present disclosure also is directed to a method of minimizing contamination in conversion of corn oil to corn oil fatty acid (COFA) comprising: (A) introducing at least one of an antioxidant or antimicrobial agent to corn oil prior to conversion of the corn oil to COFA; (B) introducing an enzyme that is capable of catalyzing the corn oil to COFA conversion to the corn oil in the presence of the least one of an antioxidant or antimicrobial agent; and (C) converting the corn oil to COFA in the presence of the enzyme and the at least one of an antioxidant or antimicrobial agent. In some embodiments, the steps A and B are performed coextensively. In some embodiments, the enzyme comprises lipase.

In some embodiments, the method further comprises heating the COFA, enzyme and the at least one of an antioxidant or antimicrobial agent mixture to deactivate the enzyme. In some embodiments, the method further comprises utilizing the COFA to extract fermentation product from fermentation broth without removing the at least one of an antioxidant or antimicrobial agent from the COFA.

In some embodiments, the fermentation product comprises product alcohol. In some embodiments, product alcohol comprises butanol. In some embodiments, butanol comprises at least one of 1-butanol, 2-butanol, tert-butanol, isobutanol, or combinations thereof.

In some embodiments, the antimicrobial agent is introduced in sufficient concentration to the corn oil so the COFA that results maintains an acceptable level of contamination. In some embodiments, the antimicrobial agent comprises butylated hydroxytoluene (BHT). In some embodiments, the antimicrobial agent exhibits antimicrobial activity to gram-positive and gram-negative bacteria, but does not appreciably inhibit yeast. In some embodiments, the antimicrobial agent exhibits antimicrobial activity to *Lactobacillus*, but does not appreciably inhibit *Saccharomyces*. In some embodiments, the antimicrobial agent comprises at least one of tocopherols, tocotrienols, amino acids with antioxidant activity, butylated hydroxyanisole (BHA), butylated hydroxytoluene (BHT), other alkylated phenols, epigallocatechin gallate (EGCG), epigallocatechin (EGC), epicatechin gallate (ECG), gallic acid, gallic esters (e.g., propyl gallate), carnosol, carnosic acid, ursolic acid, tanshen I, dihydrotanshinone, tanshinone IIA, tanshinone IIB, danshenxinkun B, peroxidase enzymes, immobilized borohydrides, Lascorbic acid 6-palmitate, anthocyanidins, anthocyanins, ethoxyquin, tertiary-butylhydroquinone (TBHQ), or combinations thereof.

In another method in accordance with the present disclosure, the method is usable to decontaminate a fermentation system that implements extractant to recover product from fermentation broth including generating a solution that includes an interfactant in sufficient concentration to cause extractant that adheres to a surface of the fermentation system to be removed from the surface; and applying the solution to the surface to cause extractant to release from the surface due to interaction of the interfactant to form a dispersion of extractant in the solution, and destabilizing the dispersion to recover the extractant as a separate phase. In some embodiments, the extractant is an antioxidant. In an embodiment, the sufficient concentration is effective to form a heterogeneous dispersion but is not included in a concentration effective to cause the extractant, after the destabilizing, to be bio-incompatible with a butanologen.

In further embodiments, destabilizing comprises at least one of heating the dispersion, adjusting the dispersion's pH, adding reagent, adding another interfactant to substantially restore the interfacial tension between the extractant and solution to at least that before the applying, mechanical destabilization, centrifugation, coalescence, de-emulsifying, cooling the dispersion, or combinations thereof.

In embodiments, the interfactant is miscible in the aqueous phase and sufficiently oleophilic to cause the extractant to form the dispersion with the solution. In some embodiments, the interfactant partitions into the extractant so the interfactant is in the extractant at a second concentration at the destabilizing. In another embodiment, the interfactant in the extractant at the second concentration is biocompatible with a recombinant microorganism in the fermentation broth. In examples, the interfactant at the second concentration is effective to improve the affinity for butanol of the extractant (e.g., the $K_d$) in comparison to extractant without interfactant. In further embodiments, the sufficient concentration is an amount of interfactant that is sufficient to populate adjacent an interface between the extractant and water included in the solution, but does not result in interfactant being incorporated in the water in appreciable amount when the dispersion is formed. In embodiments, the interfactant at the concentration is effective to biologically deactivate a contaminant microorganism on the surface.

In some embodiments, the interfactant comprises a choline salt. In examples, the choline salt comprises at least one of choline citrate, choline hydroxide, phosphatidylcholine, bitartrate, choline chloride, choline acetate, a choline fatty salt, choline oleate, choline stearate, choline sulfate, choline phosphate, choline linoleate, choline isobutyrate, or a combination thereof.

In embodiments, the dispersion has a pH of nine (9) or less at the destabilizing. In some embodiments, the solution has a pH of approximately nine (9) or greater at the application.

In embodiments, the applying is performed at a first temperature that is lower than a second temperature at which the destabilizing occurs. In some embodiments, the first and second temperatures are in the range of between thirty degrees to one hundred degrees Celsius (30°-100° C.). In some examples, the first and second temperatures are different by at least five degrees.

In embodiments, the extractant comprises corn oil fatty acid (COFA). In some examples, applying comprises spraying the solution on the surface. In embodiments, the method further includes performing at least one of a caustic or acid wash of the surface. In some embodiments, the pH of the solution at application is at approximately the pKa for COFA or above.

In additional embodiments, the interfactant comprises at least one of urea, alkyl urea, a quaternary ammonium salt, a polyether glycol, Tergitol™ (Dow Chemical Company, Midland Mich.), ethoxylate, trialkylphosphate, tetramethyl urea, tetraethylurea, a short chain phosphate, an alkyl phosphate, isobutyrate, a bridging compound, monoalkylphosphate, dialkylphosphate, or a combination thereof.

In embodiments, a method for recovering a corn extractant from a surface of equipment includes applying a solution, at a first condition, that includes interfactant at a concentration that is effective to form a dispersion with corn extractant that adhered to a surface of equipment, the concentration being sufficiently high so interfactant is present in an aqueous phase and populates an interface between the corn extractant and the aqueous phase, but is not appreciably present in the aqueous phase's entirety when the dispersion is formed; and destabilizing the dispersion to cause the corn extractant to form a separable phase by adjusting the dispersion to a second condition that is different from the first condition.

In embodiments, the first and second conditions are at least one of different temperatures, different pH; different concentrations of another interfactant, or a combination thereof. In examples, the second condition corresponds to at least one of a mechanically destabilized version of the dispersion at the first condition, a coalesced version of the dispersant at the first condition, a de-emulsified version of the dispersion at the first condition, or combinations thereof. In embodiments, the concentration is effectively high so the dispersion comprises a homogeneous solution. In some embodiments, the concentration is effective to form a heterogeneous dispersion but is not a high enough concentration to cause the dispersion to comprise a homogeneous solution. In implementations, the second condition corresponds to at least one of heating the dispersion, adjusting the dispersion's pH, adding reagent, adding another interfactant to substantially restore the solution's interfacial tension, mechanical destabilization, centrifugation, coalescence, de-emulsifying, cooling the dispersion, or combinations thereof.

In some embodiments, the interfactant is hydrophilic and sufficiently oleophilic to cause the corn extractant to form the dispersion with the solution at the applying. In examples, the interfactant partitions into the corn extractant so the interfactant is in the corn extractant at a second concentration at the destabilizing. In some embodiments, the second phase is biocompatible with a recombinant microorganism (e.g., a butanologen) present in fermentation broth, the second phase comprising corn extractant and interfactant at a second concentration. In embodiments, the corn extractant and interfactant in the second phase has a butanol partition coefficient (Kd) that is greater than that of the corn extractant. In examples, the pH of the solution at the application is approximately a pH of nine (9) or greater.

In embodiments, the interfactant comprises at least one of urea, alkyl urea, a quaternary ammonium salt, a choline salt, a polyether glycol, Tergitol™ (Dow Chemical Co., Midland Mich.), ethoxylate, triethyl phosphate, tetramethyl urea, tetraethyl urea, short chain phosphate, an alkyl phosphate, a bridging compound, or a combination thereof. In some embodiments, a short chain comprises a chain of two (2) carbons or less.

In some examples, the corn extractant has been used to recover a fermentation product from a fermentation broth that includes fermentable carbon substrate derived from corn. In further embodiments, separating comprises heating the solution to make the corn extractant insoluble in solution and decanting the corn extractant from the solution. In additional examples, the first condition is temperature between thirty degrees and one hundred degrees Celsius (30-100° C.) and the second condition is a second temperature that is higher than the first temperature and in the range of between thirty degrees and one hundred degrees Celsius (30-100° C.).

In embodiments, the solution at application is effective to biologically deactivate a microorganism present on the surface. In some embodiments, the method includes recycling the solution to recover additional corn extractant. In an example, the corn extractant is corn oil fatty acid (COFA).

In embodiments in accordance with the present disclosure, method for decontaminating a fermentation system that implements extractant to recover product from fermentation broth includes generating a solution that includes a solubilization agent in sufficient concentration to cause extractant that adheres to a surface of the fermentation system to be removed from the surface; applying the solution to the surface to cause extractant to release from the surface due to interaction with the solubilization agent so the extractant enters the solution; and separating the solution to recover the extractant. In some embodiments, the sufficient concentration is sufficiently high so the solution including the extractant comprises a homogeneous solution. In embodiments, separating comprises at least one of distilling, evaporating, or combinations thereof.

In examples, the solubilization agent is miscible in the aqueous phase and sufficiently oleophilic to cause the extractant to enter the solution. In some embodiments, the solution has a pH of approximately nine (9) or greater at the application. In examples, the extractant comprises corn oil fatty acid (COFA). In some embodiments, the pH of the solution at application is at approximately the pKa for COFA or above.

In embodiments, the solution comprises at least one of butyric acid, acetic acid, isobutyric acid, isoamyl alcohol, butanediol, salicylic acid, salicylate esters, parahydroxybenzoic acid, parahydroxybenzoate esters, and combination thereof.

While various embodiments of the present invention have been described herein, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the claims and their equivalents.

DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

DESCRIPTION

Overview

Figure 1:
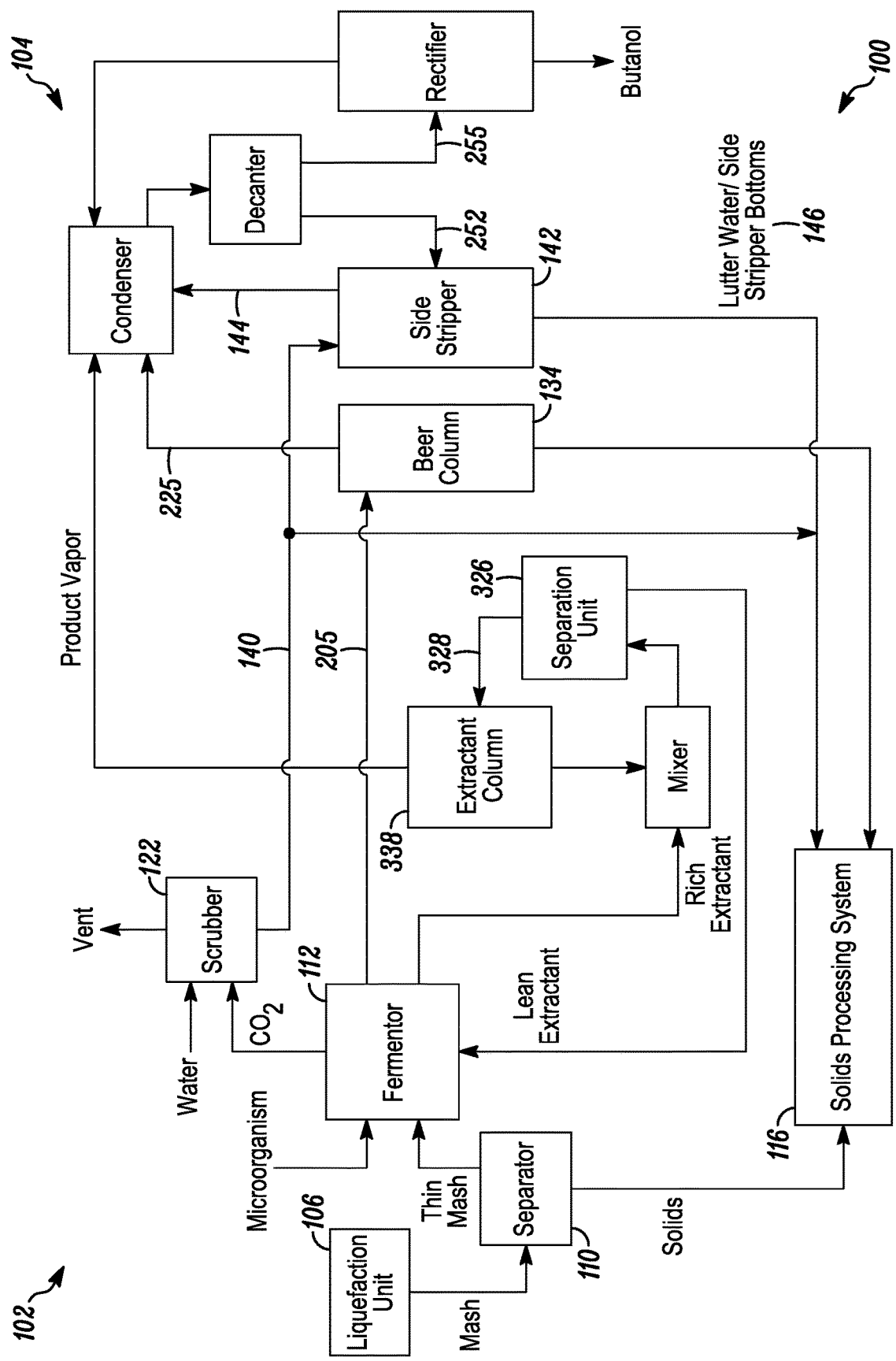
FIG. 1 illustrates example fermentation and distillation systems, such as for producing butanol from biomass.

Fermentation and distillation processes are subject to contamination from a variety of sources. Example sources of contamination include, but are not limited to, contaminants in biomass, environmental contaminants (e.g., wild-type microorganisms), equipment contamination, fermentation material contaminants (e.g., yeast or bacteria contaminants), and so forth. In some instances, contamination inhibits production of intended fermentation products and/or competes with a microorganism that produces the intended fermentation product for fermentable carbon substrate. For example, lactic acid produced from a *lactobacillus* contaminant can reduce butanol production by consuming carbon substrate that would otherwise be available to the microorganism and produce lactic acid that inhibits or kills off a butanologen microorganisms, e.g., makes them biologically inactive. Although significant effort is spent to minimize contamination, at times contamination can occur that diminishes overall efficiency of the processes and facilities implementing these processes and/or result in contamination of the product or production of unintended co-products. Contamination leads to yield loss, lost production, aborted fermentation batches, and so forth.

Additionally, some contamination may be tolerable because it is associated with a co-product that while not intended or intended in a low amount, would be more difficult to eliminate rather than to minimize its production. For example, ethanologens, a microorganism capable of producing ethanol, can contaminate butanol production by a genetically modified microorganism, while ethanol production is not intended it may be problematic to fully remove the ethanologens. In situations such as this, ethanol production may be accepted or tolerable to a particular level, such as a level associated with a cost-benefit analysis, but beyond this amount, it may be a contaminant that is to be eliminated.

Decontaminating fermentation and distillation equipment is problematic. Typically, fermentation and distillation equipment includes a large number of pipes, vessels (tanks), complex machinery (e.g., centrifuges, distillation columns, blenders, mixers, heaters, chillers, extraction equipment), and so forth that may become contaminated. Contamination can build up in fermentation equipment over successive fermentations, from feedstock contamination, and so forth.

Fermentation and separation of fermentation product has multiple steps with multiple considerations and competing priorities.

Continuous fermentation system (e.g., fermentation systems that ferment product on a continual or near continual basis) may be subject to contamination as fermentation broth is recycled for subsequent fermentation. Dissembling distillation and/or fermentation equipment to minimize contamination is not practical as it increases downtime and leads to inefficiency.

Cleaning fermentation equipment can be difficult as cleaning techniques may impact intended processes, inhibit microorganism generating fermentation products (e.g., intended fermentation products), consume equipment time, implement strong cleaning solutions/materials, involve multiple issues (e.g., cleaning particulate matter, organic matter, clean piping, vessels, complex machinery), generate disposal problems, increase downtime, decrease efficiency, and so forth. For example, chemicals such as caustics, while good at eliminating contamination, can kill microorganisms that produce intended fermentation product or require additional cleaning steps, and so on. These issues can be exacerbated for fermentation and distillation equipment that operate on a continual or substantially continual basis because there is little down-time for cleaning to be performed. Fermentation equipment, for instance, for use in producing alcohol for the fuel and specialty chemical may produce the alcohol on a continual basis, or implement multiple batches to provide substantially continuous production.

Distillation equipment too can be complex or difficult to decontaminate. Distillation columns, for instance, can exhibit diminished performance, increase off-specification distillate production during use as components are put on-line or off-line. Other issues include the introduction of contaminants from fermentation or fermentation product separation into a stream of fermentation product to distillation equipment. Other issues and considerations exist as well. Balancing overall production while maintaining hygienic production and efficient production is a daunting task.

Production of alcohols other than ethanol have additional contamination issues. Butanol fermentation can be contaminated by microorganisms that do not pose a significant issue in ethanol production, e.g., contamination by ethanologens. Ethanologens, may originate from the environment, e.g., an adjacent ethanol fermentation or the like. These contaminants (e.g., ethanol producing yeast) compete with or inhibit fermentation of butanol.

Butanol can be produced using genetically modified microorganisms that are engineered to produce butanol at elevated rates and at high concentrations in comparison to traditional ABE butanol production. Production of ethanol, which may be an unintended co-product or a co-product that is acceptable at a minor level may compete with butanologens for fermentable carbon substrate material. Other contaminant microorganisms, such acetic or lactic acid produced in fermentation, can inhibit or even kill-off butanologens. Contamination can diminish butanol production, result in a non-preferred ratio of co-products (e.g., intended co-products in comparison to non-preferred products).

Example butanologens and pathways are described in U.S. Pat. Nos. 7,851,188; 7,993,889; 8,178,328; 8,273,558; and 8,283,144; all of which are hereby incorporated by reference in their entireties. Butanologens may use a variety of pathways to produce butanol.

Accordingly methods, techniques, approaches, systems, and apparatus for mitigating, minimizing, or eliminating contamination in fermentation and distillation processes and systems are described. These techniques, approaches, equipment, and so forth can be used to decontaminate using clean in place (CIP) cleaning and/or sterilize in place (SIP) techniques without disassembly or reconfiguration of the distillation and/or fermentation equipment. These techniques can be implemented alone or in combination with the other process, approaches, techniques, and so forth described herein or with other decontamination processes.

In order to further understand the subject matter of this disclosure, commonly implemented terminology is described herein below. The following descriptions are provided for reference. As should be apparent, if the use or context of one or more of these terms in this document differs from that described directly below, it is that usage, understanding, and/or context of that specific instance that controls. Unless used otherwise, the terms implement their common meaning as understood by one of ordinary skill in the art.

Unless stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, e.g., occurrences of the element or component. Therefore "a" or "an" should be read to include one or at least one, and the singular word form of the element or component also includes the plural unless the number is obviously meant to be singular.

The term "about" modifying the quantity of an ingredient, temperature or reactant of the invention employed refers to variation in the numerical quantity that can occur, for example, through typical measuring and liquid handling procedures used for making concentrates or solutions consistent with standard industry practices; through inadvertent error in these procedures; through differences in the manufacture or control, source, or purity of the ingredients employed to make the compositions or to carry out the methods; and the like. The term "about" may encompass amounts that differ due to different equilibrium conditions for a composition resulting from a particular initial mixture. Whether or not modified by the term "about," the claims include equivalents to the quantities. In one embodiment, the term "about" means within 10% of the reported numerical value, alternatively within 5% of the reported numerical value.

Biomass refers to a natural product comprising hydrolysable polysaccharides that provide fermentable sugars, including any sugars and starch derived from natural resources such as corn, sugar cane, wheat, cellulosic or lignocellulosic material, and materials comprising cellulose, hemicellulose, lignin, starch, oligosaccharides, disaccharides, monosaccharides, and mixtures thereof. Biomass may also comprise additional components, such as protein and/or lipids. Biomass may be derived from a single source or comprise a mixture derived from more than one source, for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacturing, yard waste, waste sugars, wood and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, soy, whey, whey permeate, components obtained from milling of grains, trees, branches, roots, leaves, wood chips, sawdust, shrubs and bushes, vegetables, fruits, flowers, animal manure, and mixtures thereof. For example, mash, juice, molasses, or hydrolysate may be formed from biomass by any processing known in the art for processing biomass for purposes of fermentation, such as by milling, treating, and/or liquefying. For example, corn may be processed by wet milling or dry milling and subsequently liquefied to produce mash. Cellulosic and/or lignocellulosic biomass may be processed to obtain a hydrolysate containing fermentable sugars by any method known to one skilled in the art (see, e.g., U.S. Patent Application Publication No. 2007/0031918; the entire contents of which is herein incorporated by reference). Enzymatic saccharification of cellulosic and/or lignocellulosic biomass makes use of an enzyme consortium (e.g., cellulases, xylanases, glucosidases, glucanases, lyases) for breaking down cellulose and hemicellulose to produce a hydrolysate containing sugars including glucose, xylose, and arabinose. Saccharification enzymes suitable for cellulosic and/or lignocellulosic biomass are reviewed in Lynd, et al., (Microbiol. Mol. Biol. Rev. 66:506-577, 2002).

Butanol refers to butanol isomers 1-butanol (1-BuOH), 2-butanol (2-BuOH), tert-butanol (t-BuOH), and/or isobutanol (iBuOH or i-BuOH, also known as 2-methyl-1-propanol), either individually or combinations thereof.

Fermentation product refers to intended products and/or co-products generated by a fermentation process using a microorganism, such as bacteria or yeast, that while not intended or fully intended are generally acceptable given various factors, conditions, for the fermentation. Fermentation products, while structurally identical to chemicals derived from crude oil, may be differentiable from crude oil products having identical structure due to the presence or absence of, for example, contaminants such as sulfur or nitrogen compounds. Example fermentation products include, but are not limited to alcohols or product alcohols such as butanol. In embodiments, fermentation products that are "bio-produced" (e.g., butanol) from a renewable source can be differentiated from crude oil produced products based on their $^{14}C/^{12}C$ isotope ratio. A $^{14}C/^{12}C$ isotope ratio in range of from 1:0 to greater than 0:1 indicates a bio-produced molecule produced from a fermentation process, whereas a ratio of 0:1 indicates that the molecule is fossil derived.

Distillation product refers to a product of a distillation process. For example, a fermentation product is distilled to separate or eliminate an intended material from that of a co-product or other material with which it is mixed. Distilling butanol that has been extracted from a fermentation broth using in situ product removal (ISPR) can be used to separate the butanol from other co-products, such as ethanol. Thus, a distillation product can refer to a fermentation product that has been further processed by distillation.

Alcohol and/or product alcohol refers alcohols that can be produced by a microorganism in a fermentation process that utilizes biomass as a source of fermentable carbon substrate. Product alcohols include, but are not limited to, C1 to C8 alkyl alcohols. In some embodiments, the product alcohols are C2 to C8 alkyl alcohols. In other embodiments, the product alcohols are C2 to C5 alkyl alcohols. It will be appreciated that C1 to C8 alkyl alcohols include, but are not limited to, methanol, ethanol, propanol, butanol, and pentanol. Likewise C2 to C8 alkyl alcohols include, but are not limited to, ethanol, propanol, butanol, and pentanol. In some embodiments, product alcohol may also include fusel alcohols (or fusel oils).

In situ Product Removal (ISPR) refers to removal of a fermentation product from a biological process, such as fermentation occurring in a broth including water, to remove fermentation product. ISPR can be used to control fermentation product concentration in the biological process as the product is produced, e.g., remove fermentation products from fermentation broth to reduce its concentration in the broth. ISPR can be used to remove fermentation product for further concentration and/or purification.

Fermentable carbon substrate refers to a carbon source capable of being metabolized by a microorganism for the production of fermentation product such as alcohol. Suitable fermentable carbon sources include, but are not limited to, monosaccharides such as glucose or fructose; disaccharides such as lactose or sucrose; oligosaccharides; polysaccharides such as starch or cellulose; C5 sugars such as xylose and arabinose; one carbon substrates including methane; amino acids, and mixtures thereof.

Feedstock refers to a feed in a fermentation process, the feed containing a fermentable carbon source with or without undissolved solids, and where applicable, the feed containing the fermentable carbon substrate before or after the fermentable carbon source has been liberated from starch or obtained from the hydrolysis of complex sugars by further processing such as by liquefaction, saccharification, or other process. Feedstock includes or is derived from a biomass. Suitable feedstocks include, but are not limited to, rye, wheat, corn, corn mash, cane, cane mash, barley, cellulosic material, lignocellulosic material, or mixtures thereof.

Minimize refers to a reduction in amount material or contaminants, such as a biologically active contaminant, e.g., a microorganism such as a bacterium, that produces unwanted fermentation product or does so to an extent which is beyond a tolerable or an acceptable level. For example, while production of ethanol in a fermentation broth is permitted to a predetermined level, ethanologens may be eliminated or killed off to reduce the amount of ethanol that will be produced to achieve or attempt to achieve the predetermined level. In some instances, minimization results in the elimination, the substantial elimination of a material or contaminant to a level that is of a trivial nature, insufficient to be appreciable, and so on.

Acceptable level refers to a level, such as a threshold, that is acceptable given a particular situation or set of circumstances, e.g., conditions. In some instances, an acceptable level results in the elimination of or substantial elimination of the thing or condition being reduced. For example, an acceptable level of contamination by an ethanologen can be higher than an acceptable level of contamination by an organism that is detrimental to fermentation of butanol under a set of conditions. A variety of factors may be considered in making a determination of what is an acceptable level, what level is associated with elimination or substantial elimination of a thing or condition.

Sugar refers to oligosaccharides, disaccharides, monosaccharides, and/or mixtures thereof. Saccharide include, but are not limited to, carbohydrates including starches, dextrans, glycogens, cellulose, pentosans, as well as sugars.

Fermentation broth refers to a mixture of one or more of water, sugars, solids (whether dissolved or non-dissolved), microorganisms capable of producing fermentation product (e.g., product alcohol), and other constituents. In embodiments, fermentation broth refers to the material held in the fermentor and/or cycled through the fermentor in which product alcohol is being made by the reaction of sugars to alcohol, water, and carbon dioxide ($CO_2$) by the microorganisms present.

Extractant refers to a solvent used to extract, e.g., separate, fermentation product (e.g., a product alcohol such as butanol). Extractant in some implementations is an organic solvent that is generated from a renewable resource such as biomass. For example, corn oil fatty acid (COFA) can be used as an extractant for removing butanol from fermentation broth. Those of skill in the art should appreciate that COFA, like other bio derived fatty acids, may include additional components in various amounts such as unconverted corn oil, fatty acid butyl esters (FABE), and so on. In embodiments, an extractant is a water immiscible extractant.

Fatty acid refers to a carboxylic acid (e.g., aliphatic monocarboxylic acid) having C4 to C28 carbon atoms (commonly C12 to C24 carbon atoms), which is either saturated or unsaturated. Fatty acids may also be branched or unbranched. Fatty acids may be derived from, or contained in esterified form, in an animal or vegetable fat, oil, or wax. Fatty acids may occur naturally in the form of glycerides in fats and fatty oils or may be obtained by hydrolysis of fats or by synthesis. The term fatty acid may describe a single chemical species or a combination of fatty acids.

A process solvent stream refers to any stream within a fermentation system which comprises a solvent. By way of an example, a process solvent stream can be a stream comprising an extractant, e.g., COFA. By way of another example, a process solvent stream can be a stream from the fermentor, which can comprise a product alcohol, e.g., butanol. The process solvent stream can be heated due to where it is located in the fermentation and/or distillation system (e.g., a lean extractant stream returning from the bottoms of an extractant distillation column may be heated due to the distillation process).

Accordingly, techniques, processes, approaches, systems, equipment, and devices for performing one or more of clean in place (CIP) and/or sterilize in place (SIP) decontamination are now described in further detail. Although a particular technique, process, approach, system, equipment, or device is described in regard to an aspect of this disclosure, its principles can be applicable to another CIP or SIP techniques disclosed herein. For example, although heating a solution is described with regard to in situ cleaning of an ISPR system, heating a cleaning solution can be used in other CIP or SIP processes to increase solubility, increase the efficacy of a CIP or SIP technique, and so on.

Headings are provided solely for the reader's convenience and should not be considered as limiting or dividing this disclosure into parts. Decontamination methods, devices, systems, and apparatus are described in conjunction with providing an overview of fermentation and distillation equipment and procedures. Although butanol production is described, it is to be appreciated that other fermentation and distillation process and system configurations can benefit from the principles described herein. Thus, the principles of this disclosure can be implemented with other systems, e.g., other fermentation systems, distillation systems, and the like. While example systems, devices, apparatus, and equipment are described and illustrated (such as the fermentation and distillation system of FIG. 1), these are included for the purpose of example only. It will be apparent that modifications, additions, eliminations of can be made without departing from the scope of this disclosure. As will be apparent, a variety of factors can impact implementation of the principles described herein.

At times, this disclosure will refer to embodiments of fermentation and distillation systems and subsystems that may be implemented alone or in combination in a common facility. A facility may be an alcohol production facility at a dedicated site or it can share the site with another system, e.g., another fermentation/distillation process, a refinery, a fuel depot, a cooperative (e.g., a farmer's cooperative), a food production facility, and so forth. These other fermentation/distillation systems can be of the same type (e.g., another production line producing the same or similar types of fermentation products) or another production line producing different fermentation products, e.g., a facility that produces ethanol and butanol. In the preceding example, the butanol production line can be an ethanol production line that has been retrofitted by, for example, modifying a fermentation or distillation system to produce butanol.

FIG. 1 illustrates an example butanol production facility 100 configured to produce butanol by fermentation. As illustrated, the facility includes a fermentation system 102 and a distillation system 104. In embodiments, the facility 100 including the fermentation and distillation systems 102, 104 are configured to produce butanol using a butanalogen to generate butanol by converting fermentable carbon substrate to butanol.

Example butanologens include, but are not limited to, microorganisms that are genetically modified to produce butanol. Suitable microorganisms include, but are not limited to, a member of the genera *Clostridium, Zymomonas, Escherichia, Salmonella, Serratia, Envinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevibacterium, Schizosaccharomyces, Kluyveromyces, Yarrowia, Pichia, Zygosaccharomyces, Debaryomyces, Candida, Brettanomyces, Pachysolen, Hansenula, Issatchenkia, Trichosporon, Yamadazyma,* or *Saccharomyces*. In embodiments, recombinant microorganisms are selected from the group consisting of *Escherichia coli, Alcaligenes eutrophus, Bacillus lichenifonnis, Paenibacillus macerans, Rhodococcus erythropolis, Pseudomonas putida, Lactobacillus plantarum, Enterococcus faecium, Enterococcus gallinarium, Enterococcus faecalis, Bacillus subtilis, Candida sonorensis, Candida methanosorbosa, Kluyveromyces lactis, Kluyveromyces marxianus, Kluyveromyces thermotolerans, Issatchenkia orientalis, Debaryomyces hansenii,* and *Saccharomyces cerevisiae*. In embodiments, the recombinant microorganism is yeast. In embodiments, the recombinant microorganism is crabtree-positive yeast selected from *Saccharomyces, Zygosaccharomyces, Schizosaccharomyces, Dekkera, Torulopsis,* Brettanomyces, and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Saccharomyces uvarum, Saccharomyces castelli, Saccharomyces kluyveri, Zygosaccharomyces rouxii, Zygosaccharomyces bailli,* and *Candida glabrata*. Combinations of microorganisms can also be used.

Figure 2A:
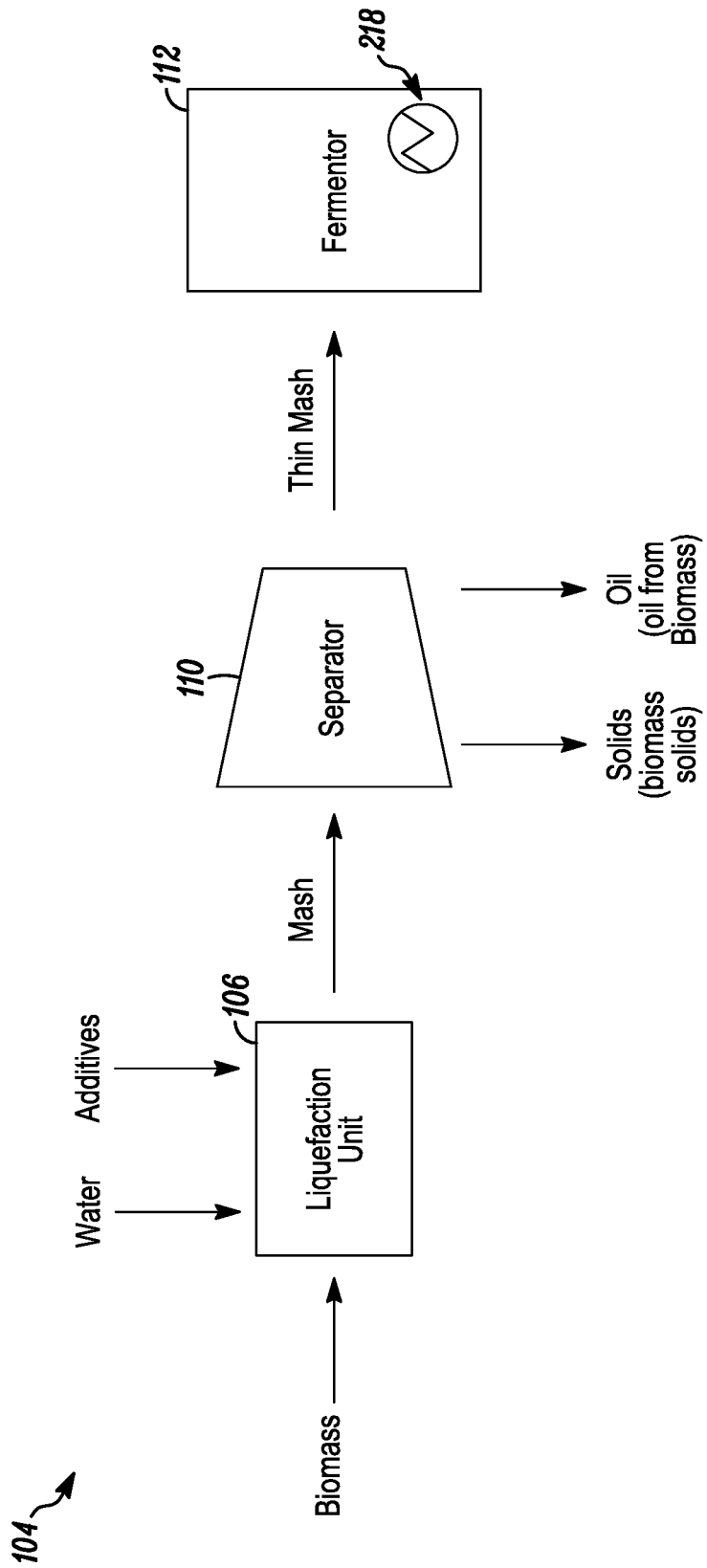
FIGS. 2A and 2B illustrate example systems for mitigating contamination in a fermentation system, such as contamination associated with thin mash production.
Figure 2B:
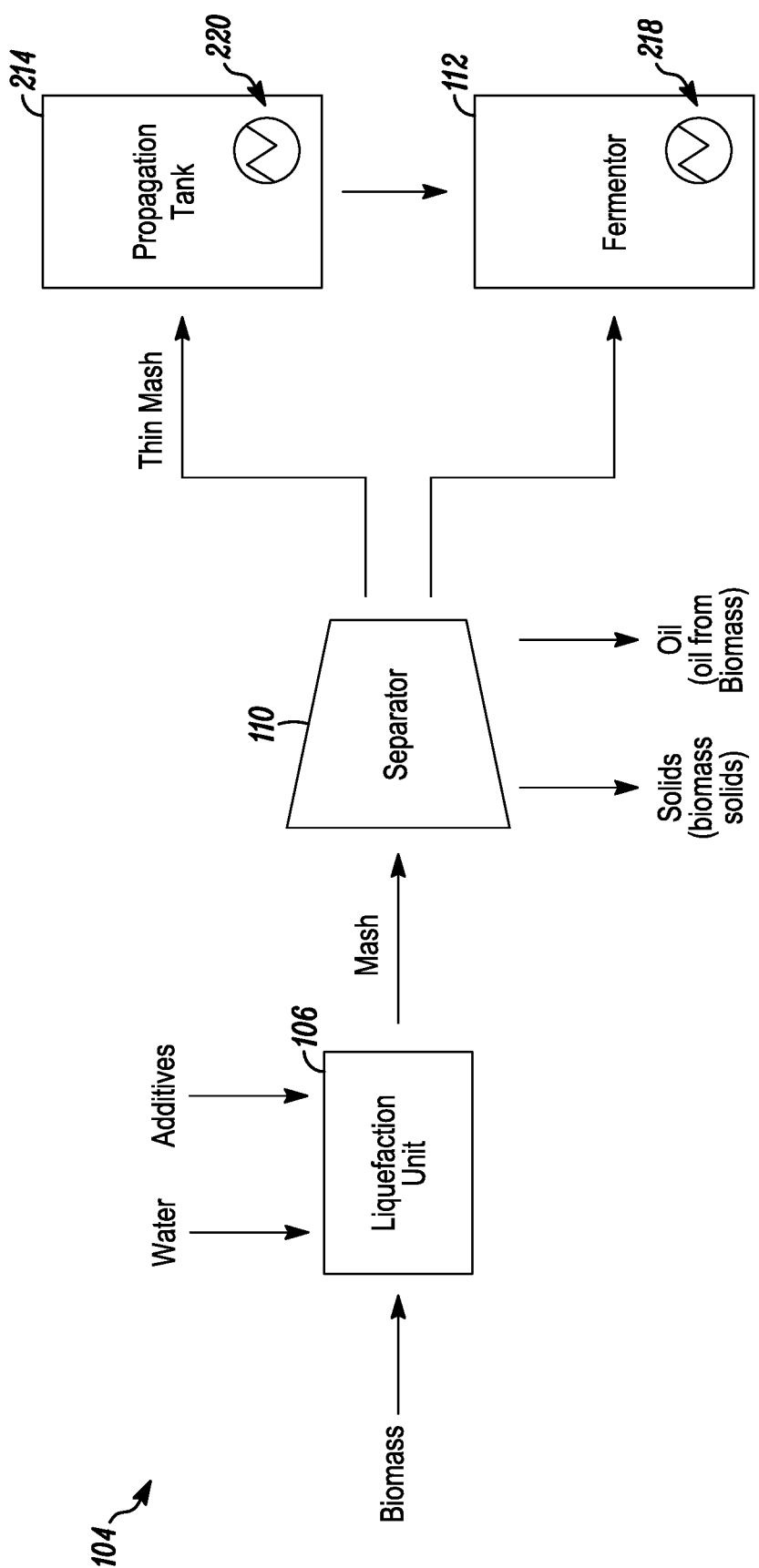

With reference to FIGS. 1, 2A, and 2B, in embodiments, production of a fermentation product starts with processing biomass to convert it to fermentable carbon substrate. The biomass may be crushed or pulverized as part of liquefaction and/or saccharification to form mash (e.g., thick mash) that is fermentable by a microorganism. A liquefaction unit 106 can create biomass slurry to which water is added or water is added as part of liquefaction. In embodiments, liquefaction includes heating the slurry or mash to approximately eighty-five to ninety-five degrees Celsius (85°-95° C.) for approximately two hours. For example, the liquefaction unit 106 or in a vessel associated with the liquefaction unit 106, e.g., a liquefaction tank includes one or more heaters 108. The heater 108 can be configured to aid in liquefaction, heat slurry to minimize or eliminate contamination and so forth. Mash can include undissolved biomass solids along with dissolved portion, e.g., sugars, starches, in an aqueous solution. Additives (e.g., enzymes, antioxidants, antimicrobial agents, antibiotics, acids/bases for adjusting pH), and so forth can be added to the crushed biomass/mash to aid in converting it to fermentable carbon substrate.

The fermentation system 102 can include appropriate equipment for incorporating enzymes, other additives, and the like. For example, the fermentation system 102 is configured to pulverizing corn into a mash with water, enzymes and heating the mash to convert biomass into various starches and/or sugars, such as in a liquefaction tank. Other liquefaction processes include, an acid process, an enzyme process (e.g., alpha-amylase), or an acid-enzyme process, and the like for treating biomass. The fermentation system 102 can include appropriate equipment for performing one or more liquefaction processes. Additional processes can be implemented to make the mash suitable for fermentation. In embodiments, a liquefaction unit is configured to subject biomass to simultaneous saccharification and fermentation (SSF).

A separator 110 can be included in the fermentation system 102 to separate portions of the mash from one another. In embodiments, a three-phase separator (e.g., a Tricanter manufactured by Flottweg SE (Vilsbiburg, Germany)), a device configured to separate two liquids having different specific gravities from solids, is configured to separate mash into an organic phase, an aqueous phase (that can include dissolved organics), and solids. The oil and solids may be separated from thin mash into different streams. In some embodiments, fermentation systems are configured to treat mash prior to separation. For example, enzymes, other additives, and so on are added to the mash, such as in a liquefaction tank, to cause a component to undergo chemical transformation prior to separation. Lipase, for example, can be added to the mash to convert corn oil to corn oil fatty acid (COFA, which can be a mix of carboxylic acids). In other embodiments, a fermentation system is configured to separate corn oil from the mash and incorporate Lipase to convert the oil to COFA.

In embodiments, a separator 110 such as a Tricanter, operates for between approximately two to three hours with heating at approximately eighty-five degrees Celsius (85° C.). In embodiments where corn is used as biomass, corn oil may also be produced during the preparation of the feedstock. Corn oil, can contain triglycerides, free fatty acids, diglycerides, monoglycerides, and phospholipids, that can be added to co-products or byproducts of the fermentation process (e.g., animal feed), used as an extractant for extracting fermentation product from broth, and create the ability to vary the amounts of these components in the resulting co-product. For example, controlling the fat content of solids co-product may yield a low fat, high protein animal feed that better suits the dietary needs of dairy cattle compared to a high fat product.

Other separation techniques include, but are not limited to, decanting, centrifuging, filtering, membrane filtering, and the like for separating components of the mash. Additional separation techniques include, but are not limited to decanter bowl centrifugation, three-phase centrifugation, disk stack centrifugation, filtering centrifugation, decanter centrifugation, filtration, vacuum filtration, belt-filter, pressure filtration, filtration using a screen, screen separation, grating, porous grating, flotation, hydrocyclone, filter press, screw-press, gravity settler, vortex separator, or combinations thereof. The solids or at least a portion of the solids may be filtered or screened out in a preceding or a subsequent step based on design preference. For example, large solids are initially screened or settled out prior to implementation of a centrifuge to increase the centrifuge's ability to separate the oil from the mash. In embodiments, a device configured to perform one or more of these separation processes, e.g., the separator 110, is included between a fermentor 112 and the liquefaction unit 106. It is to be apparent that a fermentation system can include multiple separators (e.g., arranged in parallel or series) so individual separators can be taken off-line for maintenance, decontamination, to permit separation in distinct steps, and so forth.

In embodiments, the number and/or operation of the units (e.g., separators) are configured to ensure sufficient fermentation/distillation product production while minimizing capital investment. In embodiments, one or more units in a fermentation or distillation system are configured to maintain a particular ratio of operating production in comparison to cleaning function. In embodiments, cleaning operation is maintained below seventy-five percent (75%) operation associated with cleaning.

The fermentation system 102 can include piping and equipment for transferring the solids, thin broth, and any oil from the biomass for further processing. This may be accomplished by installing valves and/or blinds in piping that enters and/or exits equipment, e.g., the separator 110. Additional valves may be included to bypass equipment, remove solids, remove oil, add/remove solution (such as cleaning solution), remove byproducts, and so on.

Thin mash can include sugars and/or starches from the biomass that are dissolved in water. Thin mash can also refer to mash from which one or more of oil from the biomass or solid have been removed. The thin mash is transferred to, for instance, the fermentor 112 (e.g., a fermentation vessel that can include an agitator, a heater, and so on) for fermentation. In embodiments, the separator 110 is sufficient to transfer the thin mash to the fermentor 112, while a pump is included in other embodiments to transfer the thin mash the fermentor.

Referring to FIG. 2B, in embodiments, a fermentation system 102 includes a propagation vessel or tank 214 (e.g., prop tank) that is used to propagate or grow microorganisms that produce fermentation product. Prop tanks and associated propagation processes can be implemented to do one or more of rehydrate microorganisms (e.g., yeast), condition the microorganism for fermentation, increase the microorganism in size and/or number, and otherwise prepare the microorganism for fermentation. In embodiments such as this, the fermentation system 102 is configured to transfer at least a portion of the thin mash to the prop tank 214 to grow the microorganism before adding the thin mash and microorganism mixture to the fermentor 112. The remaining portion of the thin mash can be transferred to the fermentor 112. In other embodiments, the thin mash or a portion of the remaining thin mash is routed through the prop tank 214, such as for rinsing microorganisms from the prop tank 214. It is to be apparent that thin mash can be transferred directly to the fermentor 112 in implementations.

The fermentation system 102 can include one or more monitoring systems for monitoring one or more step in the fermentation process to monitor overall production. For example, a monitoring device located in-line with piping configured to transfer thin mash from a three-phase separator to the fermentor 112 is used to monitor whether the thin mash includes solids. Monitoring devises may detect physical properties or chemical properties of the material being monitored. For example, a video camera is included to detect solid particles in thin mash.

In other embodiments, a monitoring device monitors for the presence of a contaminant or a material associated with the presence of a contaminant (e.g., inferred detection of a contaminant). In embodiments such as these, one or more decontamination procedures can be initiated responsive to a determination based on detection of at least one of presence of a contaminant, presence of an impurity whether or not associated with a contaminant, one or more contaminants meeting or exceeding a predetermined threshold, an impurity. One or more decontamination procedures can be performed until, for example, a determination is made that a predetermined cleanliness threshold has been achieved, such as responsive to detection that one or more contaminants is below the predetermined threshold or non-detection of a contaminate. In other embodiments, one or more decontamination procedures are performed a predetermined number of times responsive to a determination. As should be appreciated, methods and systems implemented for monitoring contamination and/or initiating decontamination can implement computer systems and/or computer implemented methods that are, in part enabled by computer executable instructions that are operable to cause a computer system to perform one or more steps. The computer executable instructions in accordance with this disclosure can be embodied in a variety of forms including but not limited to software, firmware, application specific integrated circuits (ASIC), in tangible non-transitory media, random access memory (RAM), hard drives, optical drives, magnetic media, and so forth.

Another example monitoring device includes a density meter used to measure flow. An example of the latter is an infrared monitor that looks for the existence of ethanol in a butanol fermentation system. Other example chemical detection approaches include gas chromatography, high performance liquid chromatography, mass spectrometry, and the like for monitoring system performance, product quality, impurities, and so forth. Monitoring devices can be included at various points of a system, e.g., fermentation or distillation systems 102, 104.

The solid phase removed by the separator 110 is sometimes referred to as "wet cake." Wet cake can be further processed to remove residual sugar, water, or other material. As an example, wet cake is washed with water to recover additional sugar (e.g., oligosaccharides) or oil present in the wet cake. The recovered sugar and the water used to remove it may be recycled, for example, to the liquefaction unit 102 as an additional sugar source, to generate slurry or mash, and so forth. Wet cake can be further processed into animal feed, extract oil, or other suitable byproducts. In embodiments, separation of feedstock slurry may also produce an oil stream. Examples describing wet cake processing can be found in U.S. Patent Application Publication No. 2012/0164302 and PCT International Publication No. WO 2012/173660; the contents of which are herein incorporated by reference. For simplicity, equipment suitable for processing wet cake is illustrated as solid phase processing system 116. A solid phase processing system 116 in accordance with the present disclosure can include a variety of equipment, subsystems and so on for processing the wet cake to obtain useful materials and transform the solids into useful product, e.g., an animal feed or feed supplement. As will be apparent, other portions of the fermentation and distillation systems 102, 104 can feed into the solid phase processing system 116. For example, a side stripper 142 can feed lutter water/side stripper bottoms to the processing system to facilitate wet cake processing.

Removal of solids from mash or slurry from mash can have several benefits. For example, removing solids prevents the solids from becoming contaminated with extractant, fermentation product (e.g., product alcohol) or microorganisms used in fermentation. This can simplify processing of these solids for animal feed and the like. Removing solids can have benefits for subsequent processing steps as well, e.g., fermentation/distillation. For example, removing solids may facilitate fermentation product, such as product alcohol, removal of through in situ product removal (ISPR) and may also allow for recycle of the microorganism. Having described initial processing of biomass, approaches for minimizing contamination in mash (e.g., thin mash) are now described.

Heat Treatment of Mash

As noted above, one or more of the biomass, initial processing steps, or equipment may introduce contaminants that can inhibit or compete with a microorganism that produces an intended fermentation product, e.g., butanol. For instance, biomass may come into contact with yeast capable of producing ethanol. If not accounted for, these ethanolgen can compete with butanologens for fermentable carbon substrate during butanol fermentation. Contaminants can reduce intended fermentation products (e.g., butanol) by consuming fermentable carbon substrate that otherwise would be available for producing fermentation product. For instance, permitting contamination, such as ethanologen contamination, beyond an acceptable level can yield co-product production (e.g., ethanol production) above an acceptable level, which results in more ethanol production in comparison to butanol production. Although ethanol may be an acceptable co-product in some instances, in others instances an acceptable level corresponds to a de minimis level or amount, no ethanol, or substantially no ethanol.

In some instances, a contaminant produces unintended fermentation product (e.g., acetic acid, lactic acid) that can inhibits intended fermentation product production. Inhibition can occur because a microorganism generating intended fermentation product is pH sensitive and the contaminant produces acidic material, the contaminant produces an impurity that reacts with, for example, a product alcohol to produce a by-product, or the like. This inhibition tendency can be in addition to consuming fermentable carbon substrate that would otherwise be available for fermentation of the product alcohol.

In embodiments, contaminants include material that was included for a purpose, but is no longer relevant for subsequent processing. Enzymes, for example, used to convert biomass to fermentable carbon substrate may contaminate later fermentation process whether or not the enzyme is active or has been deactivated.

As will be appreciated, once introduced, biologically active contaminants can propagate during initial processing. For example, contaminants may grow and/or increase in population in the liquefaction unit 106, the separator 110, in other machines, vessels, piping, or so on.

Instances in which the temperature of the mash (whether thin or not) is raised, but insufficiently so for reducing or eliminating contaminants, may increase contaminant concentration in the equipment or the mash itself. For example, heating slurry or mash to can create an environment that is favorable to contaminant microorganism growth in comparison to its temperature prior to heating. In the previous example, while a heater, such as a jet cooker, can heat the mash or slurry at a temperature between eighty-five degrees Celsius to or approximately to one hundred five degrees Celsius (85-105° C.) for between five to ten minutes (5-10 minutes) heating at this temperature is insufficient to minimize, eliminate, or substantially eliminate contaminants. This heating may be insufficient to appreciably minimize or eliminate the contaminant for a variety of reasons including, but not limited to, failing to raise its temperature to a temperature that is sufficient to kill off contaminants or it may fail to maintain an effective temperature for a sufficient time.

In contrast, heating the mash to a sufficient temperature for a sufficient time (e.g., 121° C. for 15 minutes) can effectively reduce the number of contaminants to an acceptable level for butanol production. For example, heating the mash including COFA, converted from corn oil, for at or approximately at 121° C. for 15 minutes can be sufficient to deactivate enzymes, such as Lipase, used to convert corn oil to COFA and/or eliminate ethanologens that may be present in the mash (whether thin or not). In addition, heating the mash at 121° C. for 15 minutes can be sufficient to reduce the number of other microorganisms that may be present to a sufficiently low level for butanol fermentation.

In contrast to ethanol fermentation, butanol fermentation implements higher hygienic standards as contamination that is not an issue in ethanol fermentation does pose issues for butanol production, e.g., ethanologens. For example, while maintaining a temperature of one hundred sixty Fahrenheit (160° F., or approximately 71.1° C.) is considered clean for ethanol production, it may not be sufficiently hygienic for butanol fermentation, e.g., mash and/or broth.

Fermentation production of butanol including mash contamination, in embodiments, is performed in the range of contamination counts on the order of $1\times10^2$ to $1\times10^4$/grams or milliliter range of biologically active contaminants. For example, thin mash has a contaminant microorganism count of $1\times10^3$ microorganisms per gram or milliliter of mash/broth (presuming broth has a density of approximately 1 gram per milliliter). In comparison, ethanol cleanliness may be on the order of a microorganism contaminate count of $1\times10^5$ per milliliter. Accordingly, butanol mash and/or fermentation broth may have ten to a thousand less microorganisms per gram than that typically acceptable for ethanol production. In embodiments, one or more of thin mash or fermentation broth (at initiation of fermentation) has 100 times less contaminant microorganism than that for ethanol production.

As should be apparent, the microorganism (e.g., butanologen) may be more sensitive to some biologically active contaminants (and their associated impurities) than others. For example, some microorganism are more sensitive to some contaminants (and their associated impurities) than other biologically active contaminants. For example, lactic acid produced by *lactobacillus* may be more toxic than other impurities/contaminants. Accordingly, hygiene levels for certain microorganism contaminants (e.g., *lactobacillus*, coliform bacteria) are higher than others (ethanologens). As a result, an acceptable level of contamination by *lactobacillus* may be lower or significantly lower than other contaminates (e.g., counts of $1\times10^3$ or $1\times10^2$ per gram), such as ethanologens (e.g., $1\times10^4$ per gram) and so on.

Butanol fermentation procedures may be more sensitive to biologically active contaminants (and accordingly have higher hygiene thresholds) because more potential contaminants (e.g., microorganism found in most environments) are ethanologens, which in ethanol production are not an issue because they tend to increase ethanol production. These same ethanologen contaminants, if included in butanol fermentation broth, tend to reduce butanol production in favor of ethanol production. In contrast, heating mash excessively, in one or more of time or temperature (e.g., greater than 121° C. for 15 minutes), may result in starch retrogradation, which reduces the overall amount of starch available for conversion to sugar because the starch has retrograded to a form that is not convertible to fermentable carbon substrate.

Example acceptable levels include, but are not limited to, above eighty percent (80%) free; at or above ninety percent (90%) free, at or above ninety-five percent (95%), free, at or above ninety-nine percent (99%) free, at or above ninety-nine point nine percent (99.9%) free, or free or substantially free of contaminant microorganisms. In embodiments, an acceptable level of contamination is selected so co-product production by fermentation meets or is less than a predetermined ratio, and/or the amount of substrate consumed by the contaminant is below a predetermined value. Additional example acceptable levels are expressed as log kill levels that respectively indicate the numbers of biologically active contaminants that are rendered y inactive due to a decontamination procedure. Acceptable log kill levels include, but are not limited to, a log kill of 4, a log kill of 5, a log kill of 6, a log kill of 7, a log kill of 8, a log kill of 9, or a log kill of 10. In embodiments, an acceptable level of contamination corresponds to a log kill of approximately 7, a log kill of 7, or a log kill of 7 or greater. A log kill in the range of approximately 7 or greater can be sufficient to reduce contamination levels while balancing other factors including, but not limited to, energy consumption, cost, process time, starch retrogradation, thermal degradation, and so forth.

In some instances, antimicrobial or antibiotics are used to minimize contamination. Although useful, antimicrobial agents and antibiotics can be costly, involve human intervention, be susceptible to adverse supply issues, be insufficient to minimize contamination to an acceptable level, and so forth. For example, the use of antimicrobials and antibiotics may be insufficient to reduce the concentration of contaminants to an acceptable level for butanol fermentation. While antimicrobial and antibiotic use alone may be insufficient or impractical for lowering contamination in butanol production, in embodiments, butanol production can implement mixed contamination mitigation approaches. For example, a fermentation system is constructed to implement antibiotics and/or antimicrobial agents at times, while implementing heat treatment decontamination at other times or in conjunction with use of antibiotics and/or antimicrobial agents. In one example, mash can be heated to one hundred twenty-one degrees Celsius (121° C.) for fifteen minutes (15 min). Antibiotics can be used in addition to the foregoing heat treatment, e.g., antibiotics are added to the mash in the fermentor 112. Example antibacterial agent includes, but is not limited to Lactrol™, an antimicrobial, from Phibro Animal Health Corporation (Teaneck, N.J.). In some examples, fuel alcohol producers prefer a lowered dose 0.5-1 ppm of Lactrol to aid hygiene. In addition, 2 ppm Penicillin G may be used.

In embodiments, the fermentation system 102 includes a heater constructed to heat the mash, e.g., thin mash, to a sufficiently high temperature for a sufficiently long residence time to minimize contamination to an acceptable level. As should be apparent, an acceptable level can be an acceptable level for a particular step or process or it can relate to an acceptable level for an overall process, e.g., fermentation or distillation. The heater can be specifically included for heating mash or serve additional purposes.

For example, the heater comprises a heater 218 for the fermentor 112 or a heater 220 included in the propagation tank 214 to propagate microorganisms for fermentation. Accordingly, heat treatment of thin mash can be performed as part of a propagation or fermentation procedure. The heater 218 can be configured to heat the thin mash in the fermentor 112 prior to addition of microorganisms for producing fermentation product, e.g., butanol. For example, the fermentation system 102 is configured to heat the thin mash in a fermentor to reduce the number of biologically active contaminants in the thin mash to an acceptable level. In embodiments, an acceptable level is a level at which all or substantially all biologically active contaminants have been sterilized or otherwise rendered biologically inactive, e.g., the sufficiently high temperature is high enough and the residence time is sufficiently long so the thin mash is sterile or effectively so. Example contaminants include, but are not limited to, wild-type yeast or bacteria. In other instances, the heater comprises a heat exchanger is included to cool other material while heating thin mash with waste heat. Other heater configurations are also possible. Multiple heaters can be included, and individual heaters can be associated with particular equipment, such as the separator, pipes, vessels, a liquefaction unit, and so on.

As will be appreciated, and is applicable throughout this disclosure, contamination can include contamination by a single type or multiple types of contaminants, e.g., different microorganisms. In embodiments, a sufficiently high temperature is a temperature that is predetermined for expected or anticipated contaminants based on a variety of factors. For example, a sufficiently high temperature may vary due to feedstock type, environmental conditions, operating parameters, and the like. In some instances, the sufficiently high temperature is determined in response to monitoring of one or more of the mash, the thin mash, fermentation broth, extractant, distillation feedstock, and so on.

As is to be appreciated, heating mash to reduce or sterilize it from contamination may be performed intermittently, such as on a set schedule and/or responsive to a determination based on one or more factors. For example, in addition to heating thin mash to reduce contamination in fermentation broth to which will be added, the heated thin mash can be used to decontaminate equipment with which the thin mash comes in contact. For example, the thin mash can be heated to a sufficiently high temperature for a sufficient period of time to raise the temperature of a surface of a pipe through which the thin mash is pumped in order to decontaminate the pipe's surface. Other equipment coming in contact with mash or the thin mash can experience similar benefits. Mash, for example, can be heated prior to separating it into thin mash, oil, and solids, not only to reduce contamination in the mash itself, but to decontaminate equipment, e.g., a centrifuge, that separates the thin mash, oil and solids. In some instances, an extent to which the mash (whether thin or not) is heated varies. For instance, a heater included in the fermentation system 102 can increase the temperature of the mash to a sufficiently high temperature (above that implemented during typical operation) to sterilize the thin mash and/or clean equipment through which the mash, e.g., thin mash, passes or is in contact.

In embodiments, determination of a sufficiently high temperature may implement an iterative process where the sufficiently high temperature is raised or lowered responsive to one or more determinations or factors. For instance, responsive to a determination that the thin mash is sterile in the fermentor 112, the sufficiently high temperature can be reduced to conserve energy while yielding thin mash that meets specification.

In embodiments, thin mash is heated to or substantially to one hundred twenty-one degrees (121° C.) Celsius for approximately fifteen minutes (15 minutes). For example, the thin mash is heated so it obtains and maintains a temperature of approximately 121° C. for fifteen minutes. In embodiments, this heating is performed in a fermentation vessel (with or without agitation) prior to incorporating microorganism capable of producing intended fermentation product, e.g., product alcohol. In additional embodiments, continuous or near continuous sterilizers run at hotter temperatures (e.g., 141° C.) with shorter exposure times (e.g., 1 minute). The mash heating process and the related equipment can be used as part of a continuous fermentation process or a batch processes. A fermentation system can be configured to implement multiple batch processes so the overall process is continuous or substantially continuous. It should be apparent that heaters or combinations of heaters can be implemented with a variety of fermentation systems and subsystems including different equipment configurations without departing from the scope of this disclosure.

Further, heat treating mash can be used to perform additional functions. For example, instead of deactivating enzymes, such as Lipase, in a separate step, a fermentation system can be configured to deactivate enzymes utilizing heat treatment of mash to deactivate the enzyme and sterilize the thin mash. As a result, deactivation of an enzyme may be performed at a significantly higher temperature (one hundred twenty-one degrees Celsius, 121° C.) than is required to deactivate the enzyme (e.g., eighty-five degrees Celsius, 85° C.). Performing decontamination and deactivation of enzymes in a single step may conserve energy, shorten overall fermentation time, reduce fermentation system, minimize capital investment, and control system complexity, and the like. Having described heat treatment of thin mash, additional decontamination techniques are described for minimizing or eliminating contamination in fermentation/distillation processes.

Minimizing Contamination in Oil to Fatty Acid Conversion and Increasing Extraction Efficiency As mentioned above, in embodiments antimicrobial agents can be used in conjunction with other approaches and techniques described herein. A fermentation system, for example, is configured to implement an antimicrobial agent to minimize contaminant growth in one or more processes, while heat treatment is implemented in others to minimize contamination.

One process that can benefit from an antimicrobial approach is the conversion of oil from biomass to fatty acids (e.g., a carbocyclic acid) that, among other uses, can be used to extract fermentation product from fermentation broth. An example of the foregoing is the use of COFA obtained from corn oil. COFA can be used to extract fermentation product, such as butanol, or other product alcohols from broth. Although this description will refer to corn oil to COFA conversion, those of skill in the art will appreciate that other oils can be converted and implemented in a similar manner.

Converting corn oil to COFA can be subject to contamination as this conversion typically occurs in the presence of fermentable carbon substrate. Corn oil to COFA conversion is also susceptible to contamination as it is performed at between approximately thirty to sixty degrees Celsius (30°-60° C.) and typically occurs at a pH of between approximately four to eight (4-8). Heat treating corn oil and/or COFA to minimize contamination during conversion can be problematic as both can be subject to thermal degradation and/or oxidation in the presence of air.

Accordingly, an antimicrobial agent can be included to minimize contamination along with the oil and an enzyme that is used to catalyze the conversion. An example enzyme for corn oil to COFA conversion is Lipase. In embodiments, an antimicrobial agent such as butylated hydroxytoluene (BHT), is added to the corn oil or mash to minimize or substantially eliminate contaminant growth during corn oil to COFA conversion. BHT exhibits antimicrobial activity to gram-positive and gram-negative bacteria (e.g., *lactobacillus*) but does not affect yeast (e.g., *Saccharomyces*) at comparable concentrations. This property of BHT makes it well-suited to minimize contamination by *lactobacillus* contaminants in instances where *Saccharomyces* is implemented to produce intended fermentation product, such as butanol. BHT also exhibits antioxidant properties to prevent oxidation during corn oil to COFA conversion. Example compounds exhibiting antimicrobial capability, include but are not limited to tocopherols, tocotrienols, amino acids with antioxidant activity, butylated hydroxyanisole (BHA), butylated hydroxytoluene (BHT), other alkylated phenols, epigallocatechin gallate (EGCG), epigallocatechin (EGC), epicatechin gallate (ECG), gallic acid, gallic esters (e.g., propyl gallate), carnosol, carnosic acid, ursolic acid, tanshen I, dihydrotanshinone, tanshinone IIA, tanshinone JIB, danshenxinkun B, peroxidase enzymes, immobilized borohydrides, Lascorbic acid 6-palmitate, anthocyanidins, anthocyanins, ethoxyquin, tertiary-butylhydroquinone (TBHQ), combinations thereof and those describe in Fung et al, *CRC Critical Reviews Microbiol.* 12(2):153-83 (1985); Sankaran, J. *Food Science Technol.* 13:203-4 (1976); and Yankah et al., *Lipids AOC Press* 33(11):1139-1145 (1998), all of which are incorporated herein by reference. Examples of compounds with antioxidant and antimicrobial activity include, but are not limited to, butylated hydroxytoluene, propyl gallate, butylated hydroxyanisole, and tertiary butylhydroquinone.

Classes of antioxidants that fit these criteria (e.g., promote extraction efficiency) would may perform well in a process where *lactobacillus* is a potential contaminant to sacchromyces producing butanol. BHT, in particular as a phenolic compound, also offers an exceptionally high degree of butanol affinity. The tertiary butyl groups present on the molecule along with aromatic hydroxyl group can aid in the favorable absorption of isobutanol from an aqueous phase. BHT can serve to selectively enhance biocompatibility and to enhance butanol extraction.

Minimizing contaminants in corn oil to COFA conversion can minimize or eliminate steps/equipment used to purify COFA. This is a consideration, as COFA can be reintroduced to fermentation broth to extract fermentation products, e.g., product alcohols. Although an extractant purification system, e.g., a system capable of purifying COFA of contaminants and impurities, can be included in a fermentation system, including a system such as this can increase the cost and complexity of the overall fermentation system. Implementing antimicrobial agent/configuring a fermentation system to introduce antimicrobial agents in a corn oil to COFA conversion can minimize COFA contamination and simplify or eliminate purification the COFA prior to use as an extractant. In some embodiments, an antimicrobial agent and/or an antioxidant may remain in the extractant. For example, BHT incorporated with corn oil prior to conversion to COFA remains in the COFA to minimize contamination and/or oxidation during use as an extractant. Use of an antioxidant and/or antimicrobial agent is described in U.S. patent application Ser. No. 14/032,328, entitled Recyclable Extractant Compositions filed on 20 Sep. 2013 which is hereby incorporated by reference in its entirety.

In an experimental example, a cell inoculum originated from a 72 hour seed flask with a 30 g/L synthetic medium. The culture was inoculated into 40 g/L glucose in synthetic medium. Crude COFA samples were incubated with BHT for 60 hours; the five percent (5%) by weight/volume (w/v) BHT sample took between 3 and 5 days to completely dissolve (no agitation) so an undissolved sample was initially added to the flask. Fifty percent (50%) volume/volume (v/v) crude COFA with or without BHT was used for each shake flask culture. The flasks were incubated in a thirty degree Celsius (30° C.), 260 revolutions per minute (rpm) shaker. One to one point five milliliter (1-1.5) mL samples were taken at points in time. The samples were centrifuged at fourteen thousand revolutions per minute (14,000 rpm) for four (4) minutes, the COFA overlay was removed, the pellet/cells were vortexed to resuspended and the appropriate amount was removed for cell count, the samples were centrifuged again, and supernatant was removed for YSI glucose measurements. No difference in glucose consumption was observed for BHT levels that range from zero percent by weight (0 wt %) (control) to five percent by weight (5 wt %).

Use of an antioxidant can reduce extractant degradation rate. In addition, some antioxidants can act as antimicrobials towards microbes other than the primary microorganism used to produce butanol. Thus, judicious use of certain classes of antioxidants can provide antioxidant and antimicrobial benefits for the production of butanol. In addition, certain classes of antioxidants can enhance the extraction efficiency for butanol and the deliberate addition of excess antioxidant to COFA can improve extraction, oxidative stability and biocompatibility simultaneously. For example, BHT is an effective scavenger of radicals that would otherwise negatively impact some components of COFA and at the same time, BHT has a very high affinity for butanol compared to other candidate extractants primarily because it is a butylated phenol compound.

The UNIFAC mixture property estimation method in conjunction with the Aspen flowsheet simulation software was used to predict the extraction of isobutanol from water by various blends of COFA and BHT as indicated below.

For example, for a process that maintains a constant 32 grams per liter (gpl) titer isobutanol in the rich COFA to be distilled, the aqueous titer can be reduced from 10 gpl to 9 gpl by adding just 5% BHT. Adding another 5% BHT for a total of 10% BHT can reduce the aqueous titer to 8 gpl without adding more energy consumption to the process. This can have the benefit of higher production due to lower product inhibition.

Fermentation and In Situ Product Removal

With reference to FIGS. 1 and 3A-3C, additional fermentation related processes are described in further detail having described: initial biomass processing, conversion of biomass to fermentable carbon substrate, separation of oil and solids from thin mash, conversion of oil to fatty acids suitable for extracting fermentation product, and heat treatment of mash (e.g., thin mash). The fermentation processes herein can be used in conjunction with one or more of the processes described above or with other fermentation and/or distillation related processes described further on in this document or are generally known.

For the purpose of example only, the following description presumes thin mash is present in the fermentor 112. The thin mash may have been treated according to one or more of the approaches described above. The following descriptions provide examples in which the thin mash or the fermentor containing the thin mash includes contamination that is in excess of an acceptable level, in these instances, the thin mash may not have been treated as described or contaminants may have been introduced from a variety of sources, such as from: a contamination fermentor or propagation tank, contaminated fermentation broth materials (e.g., contamination in water, contamination in yeast or bacteria that produces fermentation product, water contamination), and so on.

At times reference is made to approaches implementing extractant to remove fermentation product, e.g., product alcohol, during or in conjunction with fermentation. It will be appreciated that other approaches for removing fermentation products from fermentation broth are available and can be used with the fermentation processes and systems described herein. It should be understood that the underlying fermentation processes and those process, approaches, techniques, described with respect to liquid extraction techniques are not tied or restricted to the use of a liquid extractant.

The thin mash and microorganisms configured to produce intended fermentation product are added to the fermentor 108. Additional materials, such as additives, enzymes, recycled fermentation broth (e.g., recycled lean fermentation broth), additional water, extractant (whether recycled or not), and so forth may be included as well as illustrated generally in FIG. 3A.

In embodiments, thin mash is added to the fermentor 112 to a pre-determined level. For example, yeast or bacteria can be added directly to thin mash in the fermentor 112. In other embodiments, microorganisms and thin mash are added in a propagation tank, initial propagation is performed, and then the thin mash including microorganisms is transferred to the fermentor 112. In further examples, additional microorganisms can be added directly to the fermentor 112. In other words, microorganisms are added to thin mash in a propagation tank and additional microorganisms are added to the thin mash in the fermentor 112. As should be apparent, a plurality of fermentors can be operated in parallel or substantially parallel to provide substantially continuous fermentation product production, have one fermentor act as a prop tank for another fermentor, and so forth.

An agitator, included in the fermentor 112 may be activated following the addition of the microorganism. In embodiments, the agitator is activated following addition of the contents of a prop tank, e.g., thin mash to which microorganisms have been added and allowed to populate. In embodiments, one or more of thin mash, thin fermentation broth (broth being recycled), or water may be fed to the fermentor 112 until steady state fermentation is reached. For example, the fermentable carbon substrate is fermented by the microorganisms to produce butanol.

Having described fermentation processes, approaches, techniques and accompanying devices product removal and in-particular in situ product removal are now discussed in further detail. As should be apparent, the principles described in the following discussion and those in the preceding discussion regarding fermentation and fermentation product removal using extractant can be implemented in conjunction with one another and with other approaches, techniques, systems, and devices.

In Situ Product Removal

Figure 3A:
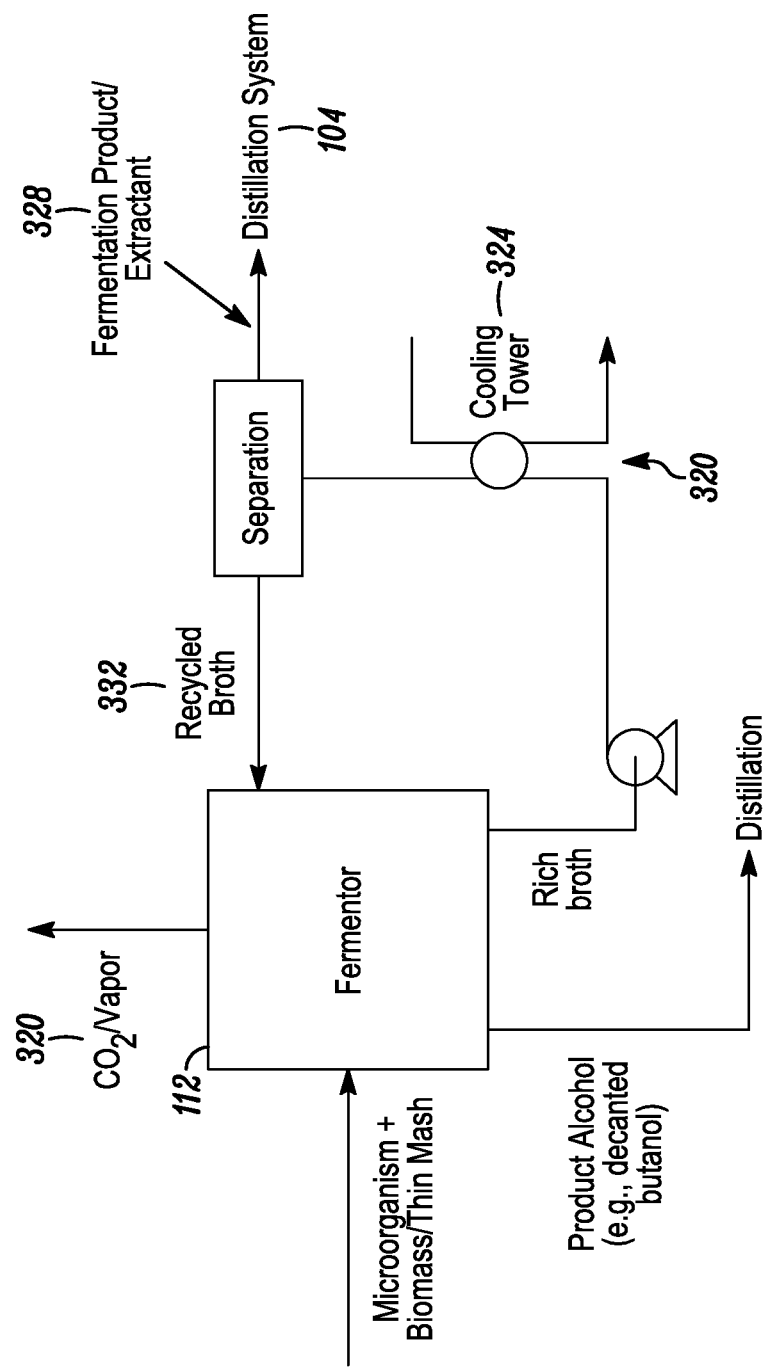
FIGS. 3A through 3C illustrate example in situ product recovery (ISPR) systems that can be included in fermentation systems.
Figure 3B:
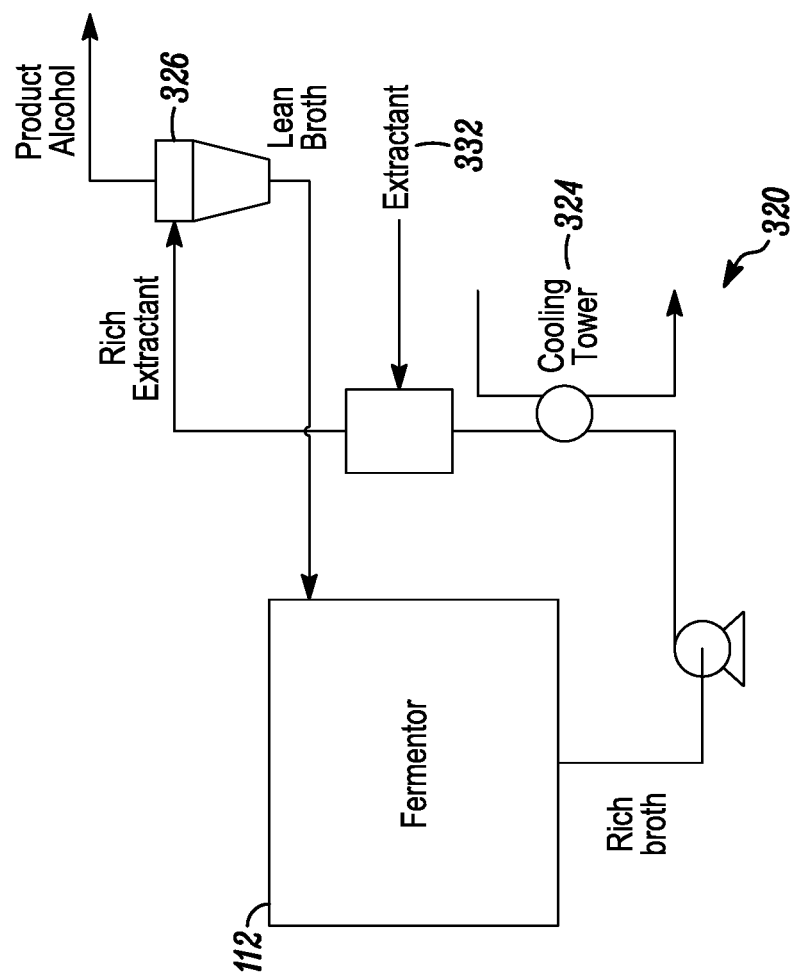
Figure 3C:
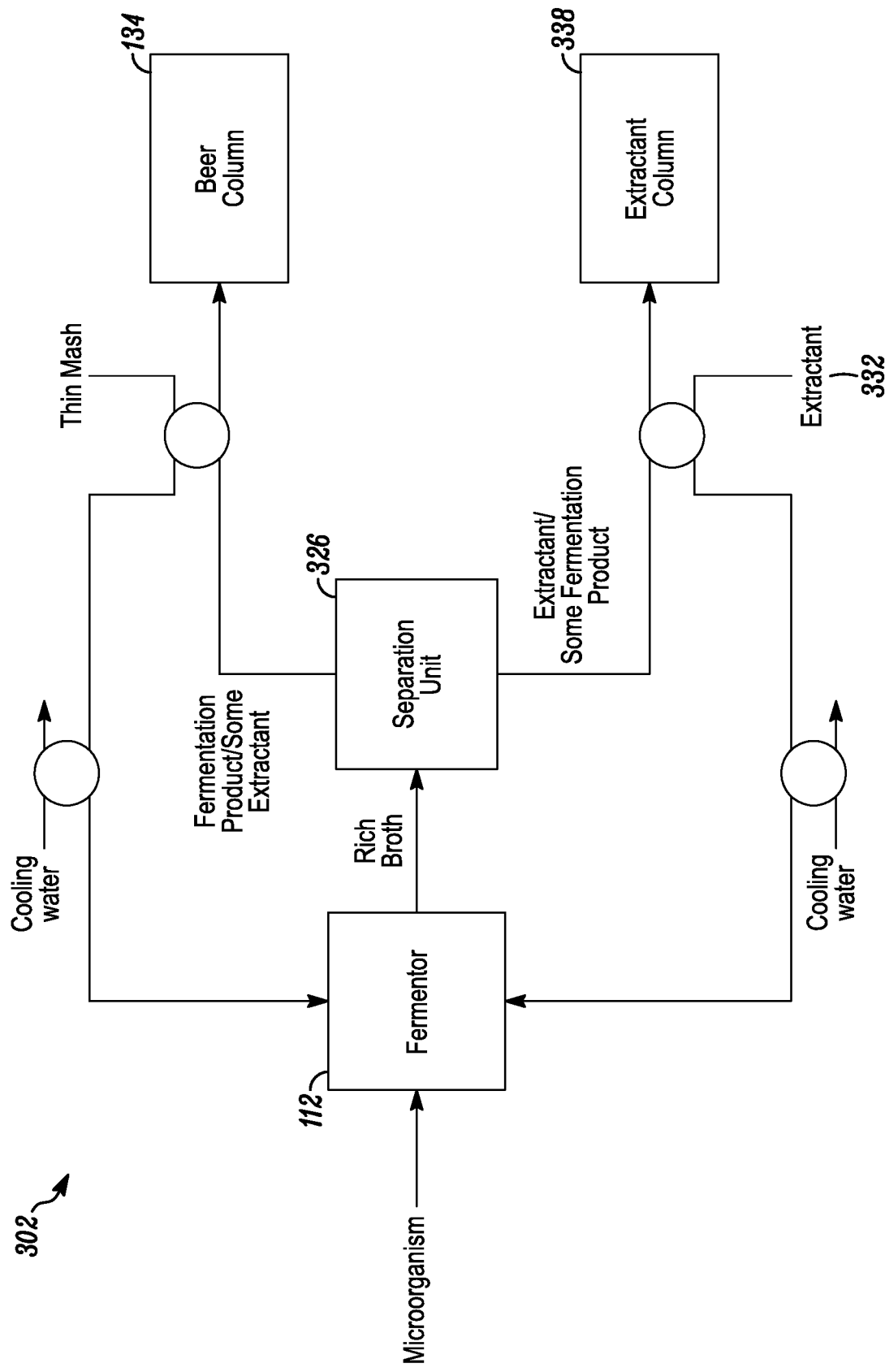

FIGS. 3A through 3C illustrate portions of fermentation systems 302 in accordance with embodiments of the present disclosure. In some embodiments, fermentation broth, generated from thin mash and the microorganism is circulated through a cooling loop 320 in order to maintain a temperature below, for example, thirty-five degrees Celsius (35° C.) or another control point. For example, a heat exchanger can be used to cool the fermentation broth/extractant in a biphasic mixture with the broth. Waste heat from this process can be used for other purposes. Gases 320 generated during the fermentation (e.g., carbon dioxide) can be vented to scrubber 122 (such as illustrated as 122 in FIG. 1) where it is placed in contact with water and a bottoms stream that can be recycled for liquefaction of biomass.

In these embodiments, extraction of a fermentation product such as butanol occurs downstream of the fermentor 112, such as in the cooling loop 320. FIG. 3A illustrates a fermentation system 302 in which butanol is extracted on a continuous or substantially continuous basis downstream from the fermentor 112. In these embodiments, fermentation broth is cooled by cycling it through an external cooling loop 320 that is in contact with a heat exchanger, such as a cooling tower 324.

The cooled broth can then be transferred to a separation unit 326 that forms a stream that is rich in fermentation product 328, e.g., a butanol rich stream, e.g., an organic phase (e.g., a butanol-containing phase) and a stream of lean broth 330, e.g., aqueous phase or a stream that is depleted of butanol in comparison to fermentation broth in the fermentor. The butanol-containing organic phase 328 may comprise butanol, water, extractant, non-condensible gases as well as byproducts of the fermentation process that have sufficient solubility to partition into the extractant. In embodiments, the organic phase 328 has a butanol concentration from about 0.1 weight percent (wt %) to about 50 wt %, about 0.5 wt % to about 40 wt %, from about 1 wt % to about 35 wt %, from about 2 wt % to about 30 wt %, from about 3 wt % to about 25 wt %, from about 5 wt % to about 20 wt % based on the weight of butanol-containing organic phase 328.

In embodiments, the separation unit 326 comprises one or more of a hydrocyclone, a centrifuge, an inline vortex separator, a decanter (e.g., extractant decanter), or a filter. For example, a series of centrifuges is used to separate the extractant from the broth. In other examples, a separation unit 326 comprises one or more inline vortex separators or may comprise a single inline vortex separator having sufficient capacity based on the size of the fermentor 112 and/or amount of fermentation broth to be used in the fermentation system 302. In embodiments, the separation unit 326 comprises one or more centrifuges arranged in parallel and/or in series.

Referring now to FIG. 3B, in embodiments a fermentation system 302 is configured for continuous extraction of fermentation product such as butanol external to the fermentor 112. In embodiments such as this, extractant, e.g., a solvent, is brought into contact with fermentation broth external to the fermentor 112 to remove fermentation product from the broth. In addition, the broth or lean broth that results from extraction of the fermentation product can be cooled to aid in maintaining the temperature of the fermentation broth in the fermentor. For example, COFA (extractant 332) can be mixed with broth in an external loop 320 to form a biphasic mix to remove product alcohol from the stream of broth and then sent to a separation unit 326 that separates the now rich extractant from the lean broth which can be recycled to the fermentor 112 or transferred to a beer column 134, such as illustrated in FIG. 1, to remove additional fermentation product from the lean broth.

Referring now to FIG. 3C, in further embodiments, extractant 332 is included in the fermentor 112. Extractant 332 can be included to remove fermentation product from the broth during fermentation. Including extractant in the fermentor 112 permits removal of butanol to minimize the toxicity effects of butanol on the butanalogen in the fermentation broth, and so forth. In embodiments, at least one flow circulation is maintained outside the fermentor 112 during fermentation to cool the fermentation broth and permit mass transfer (e.g., removal of butanol from the broth) to the extractant. Butanol may be removed from the externally circulated fermentation broth using various methods, such as low temperature flashing, liquid-liquid extraction, and gas stripping among others to remove fermentation product, such as butanol. This approach can be taken to reduce the concentration of the fermentation product (e.g., butanol) in the broth to prevent it from increasing in concentration to a level that would inhibit further production or reach a level that is toxic to the microorganism.

For instance, extractant 332 is added directly to the fermentor 112 to recover fermentation product during the fermentation process. This approach may be used to reduce the level of fermentation product in the broth, such as when a product alcohol is toxic to the microorganism at high concentrations, e.g., above a level that is tolerable to the microorganism. In this manner, fermentation product enters extractant 332 for removal. Mass transfer of the fermentation product into the extractant may be governed by the partition coefficient of the extractant given the conditions, e.g., temperature, agitation and so forth.

In examples such as this, fermentation broth is contacted with extractant by mixing to form a biphasic stream. Contacted or contacting refers to bringing the broth and extractant into physical contact such as during the fermentation. In some examples, fermentation broth is removed from fermentor 112 prior to contact with extractant. That is to say, the extraction of butanol occurs downstream of fermentor 112.

In embodiments such as these, rich extractant is transferred from the fermentor to a separation unit 326 that is generally similar to that in the embodiments illustrated in FIGS. 3A and 3B. The separation unit 326 separates the extractant including fermentation product/co-products product from the broth. For example, a stream primarily containing fermentation product 336 is transferred to a beer column 134, in contrast a stream containing primarily extractant can be sent to an extractant column 338 for further processing. In embodiments, extractant recovered by the extractant column 338 can be recycled for reuse or be separated into a product stream or be disposed of. Fermentation product recovered by the extractant column 338 can be transferred for further processing, e.g., distillation, and inclusion in distillation product. The beer column 134, included in the distillation system 104, can be used to distill the fermentation product rich stream 336 to form distillation product by the distillation system 104.

In embodiments where batch fermentation is implemented, fermentation is allowed to continue for a period of time that can be a predetermined period, based on occurrence of an event (e.g., responsive diminished carbon dioxide or fermentation product production, fermentable carbon substrate obtaining a particular concentration), and so forth. Batchwise production of butanol can be conducted with or without extractant.

Established saccharification process utilized in the industry can be implemented including, but not limited to, an acid process, an enzyme process, or an acid-enzyme process. In embodiments, an enzyme such as glucoamylase, is introduced to the fermentor 112 in order to hydrolyze sugars (e.g., oligosaccharides) present in feedstock or liquid phase to monosaccharides. Saccharification can occur in a separate saccharification unit. In embodiments, saccharification occurs prior to separation of the thin mash or after separation of the thin mash. For a description of methods and systems for processing biomass for fermentation see, for example, PCT International Publication No. WO 2011/160030; the entire contents of which are herein incorporated by reference in its entirety.

In embodiments, fermentation broth is continuously removed from fermentor 112 or it can be removed in batches. Extraction of fermentation product from the fermentation broth may be performed with or without the removal of the microorganism from the fermentation broth. For example, butanol can be extracted from the broth without removing microorganisms.

In other embodiments, the microorganism is removed from the fermentation broth using a variety of approaches including, but not limited to, filtration or centrifugation. The removed microorganisms can be reused for a subsequent fermentation. For example, extraction of butanol from the fermentation broth can be performed with or without the removal of the microorganism from the fermentation broth. The microorganism can be removed from the fermentation broth by approaches including, but not limited to, filtration or centrifugation; and the resultant microorganisms can be returned to fermentor 112 and/or prop tank 114 for reuse. Extraction of butanol can be performed with or without the removal of undissolved solids from the fermentation broth. Undissolved solids may be removed from the fermentation broth by a variety of techniques including, but not limited to, filtration or centrifugation. The solids can be recycled to the fermentor 112 or separated for use as a feed material and so forth. In embodiments, an automatic self-cleaning water filter is used to trap solids.

In embodiments, the extractant is water-immiscible and can comprise one or more organic solvents. The extractant, in embodiments, is nontoxic to the microorganism so it does not appreciably harm the microorganism should it become entrained with fermentation broth. In some embodiments, an extractant is selected due to its high partition coefficient for a fermentation product (e.g., butanol). Suitable extractants include, but are not limited to, one or more of the following: fatty alcohols, fatty acids, fatty esters, fatty aldehydes, fatty amides, triglycerides, monoalkyl phosphates, dialkyl phosphates, trialkyl phosphates or mixtures thereof. Methods for producing and recovering butanol from a fermentation broth using extractive fermentation are described in U.S. Patent Application Publication No. 2009/0305370; U.S. Patent Application Publication No. 2010/0221802; U.S. Patent Application Publication No. 2011/0097773; U.S. Patent Application Publication No. 2011/0312044; and U.S. Patent Application Publication No. 2011/0312043; the entire contents of each are herein incorporated by reference. In embodiments, the extractant is one or more ionic liquids (see, e.g., U.S. Patent Application Publication No. 2010/0143992; U.S. Patent Application Publication No. 2010/0143993; U.S. Patent Application Publication No. 2010/0143994; and U.S. Patent Application Publication No. 2010/0143995; the entire contents of each are herein incorporated by reference).

Factors impacting extractant selection include, but are not limited to one or more of (i) toxicity to the fermentation product producing microorganism (a nontoxic extractant or an extractant that is only toxic in high concentration can be preferred) (ii) be substantially immiscible with the fermentation broth, (iii) have a high partition coefficient for the extraction of intended fermentation products (e.g., product alcohols such as butanol), (iv) have a low partition coefficient for the extraction of nutrients in the broth, (v) have a low tendency to form emulsions with the fermentation medium, and (vi) be low cost and nonhazardous. Suitable organic extractants for use in the methods disclosed herein can be selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes and combination thereof. As used in this instance, the term "combinations thereof" encompasses combinations within and mixtures between these group members, for example mixtures within $C_{12}$ to $C_{22}$ fatty alcohols, and also mixtures between $C_{12}$ to $C_{22}$ fatty alcohols and $C_{12}$ to $C_{22}$ fatty acids, for example. Suitable organic extractants may be further selected from the group consisting of oleyl alcohol (CAS No. 143-28-2), behenyl alcohol (CAS No. 661-19-8), cetyl alcohol (CAS No. 36653-82-4), lauryl alcohol, also referred to as 1-dodecanol (CAS No. 112-53-8), myristyl alcohol (112-72-1), stearyl alcohol (CAS No. 112-92-5), 1-undecanol (CAS No. 112-42-5), oleic acid (CAS No. 112-80-1), lauric acid (CAS No. 143-07-7), myristic acid (CAS No. 544-63-8), stearic acid (CAS No. 57-11-4), methyl myristate CAS No. 124-10-7), methyl oleate (CAS No. 112-62-9), undecanal (CAS No. 112-44-7), lauric aldehyde (CAS No. 112-54-9), 20-methylundecanal (CAS No. 110-41-8), and mixtures thereof. These organic extractants are available commercially.

In embodiments, extractant is one or more of the following fatty acids: azaleic, capric, caprylic, castor, coconut (i.e., as a naturally-occurring combination of fatty acids, including lauric, myrisitic, palmitic, caprylic, capric, stearic, caproic, arachidic, oleic, and linoleic, for example), dimer, isostearic, lauric, linseed, myristic, oleic, olive, palm oil, palmitic, palm kernel, peanut, pelargonic, ricinoleic, sebacic, soya, stearic acid, tall oil, tallow, #12 hydroxy stearic, or any seed oil. In some embodiments, the extractant is one or more of diacids, azelaic, dimer and sebacic acid. Thus, the extractant can be a mixture of two or more different fatty acids. In embodiments, the extractant is a fatty acid derived from chemical or enzymatic hydrolysis of glycerides derived from native oil. For example, the extractant is free fatty acids obtained by enzymatic hydrolysis of native oil such as biomass lipids. In embodiments, the extractant is a fatty acid extractant selected from the group consisting of fatty acids, fatty alcohols, fatty amides, fatty acid methyl esters, lower alcohol esters of fatty acids, fatty acid glycol esters, hydroxylated triglycerides, and combinations thereof, obtained from chemical conversion of native oil such as biomass lipids as described in U.S. Patent Publication No. 2011/0312044. In these embodiments, the biomass lipids for producing extractant can be from a same or different biomass source as that of the fermentable carbon substrate. For example, lipids for producing extractant can be derived from soya, whereas the biomass is corn. Combination of different biomass sourced extractants versus biomass feedstock can be used. In embodiments, the extractant is COFA.

In embodiments, the second solvent is oleyl alcohol, 2-butyl-1-octanol, 2-hexyl-1-decanol, castor oil fatty acid methyl ester, soy oil fatty acids (SOFA), bis-(2-ethylhexyl) adipate, petroleum ether, corn oil, corn oil fatty acids (COFA), or combinations thereof.

As can be appreciated, a combination of solvents can be used to increase the partition coefficient of the product. Additionally, solvent combination can be used to adjust and optimize physical characteristics of the solvent, such as density, boiling point, and viscosity.

In embodiments illustrated in FIGS. 1-3C above, gases produced during fermentation that are non-condensible, e.g., carbon dioxide, can be vented to a scrubber for venting/recovery. Scrub stream 140 can be transferred to a side stripper column 142 to recover additional fermentation product and other volatile components into a vapor overhead stream 144 for further fermentation product/co-product recovery and to form a liquid bottoms stream 146, that at times is referred to as lutter water or side stripper bottoms. The lutter water/side stripper bottoms can be recycled for washing solids, water added to form fermentation broth or mash, and so forth.

Additional devices, equipment, and so on can be included in fermentation systems in accordance with the present disclosure. For example, a mixer is included to agitate extractant and broth (an aqueous phase) into close contact prior to separation by the separation unit 326. In the above embodiments other additional components include but are not limited to pumps, filters, membranes, separators, mixers, and so on.

Having described various techniques, approaches, devices, and equipment that are capable of producing/recovering fermentation product, e.g., product alcohol, from fermentation broth, approaches for decontaminating fermentation and distillation processes, devices, equipment and so forth are now described in additional detail. As should be apparent to those of skill in the art, the following techniques, approaches, devices, equipment, and so forth can be used in conjunction with those described above with respect to FIGS. 1-3C as well as with those described in conjunction with those described further on in this document.

Figure 4:
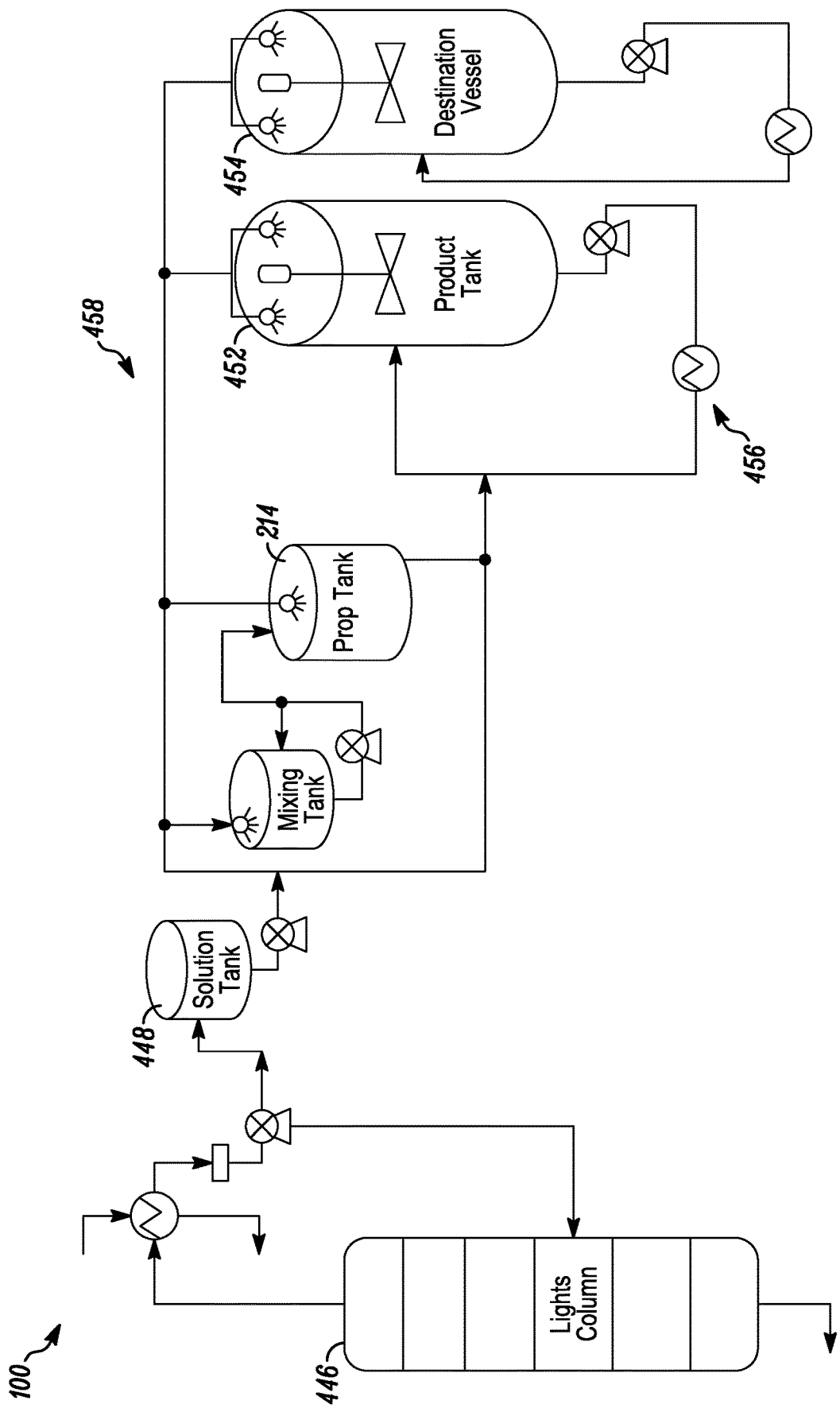
FIG. 4 illustrates an embodiment of a cleaning system that is configured to implement lights and/or off-specification (off-spec) fermentation product to decontaminate equipment included in a fermentation or distillation system.

Contamination Mitigation Using Lights/Heavies/Off-Specification Distillation Products Referring now to FIG. 4, approaches for decontaminating fermentation and distillation processes, devices, systems, and equipment using lights (e.g., light distillates, such as byproducts), heavies, off-specification (off-spec) distillation product, such as isobutanol, and combinations thereof are now described in further detail. Example lights include, but are not limited to ethanol, butanol, other low carbon containing alcohols, and combinations thereof that are produced in distillation processes, e.g., butanol production. Example heavies purge material include, but are not limited to acetic acid, isobutyric acid, isoamyl alcohol and butanediol. In some embodiments, heavies purge is used as one or more compounds in the heavies purge exhibit low volatility, high antimicrobial activity, and/or low flashpoints. The lights/off-spec material may be selected due to its ability to effective disrupting a contaminant's cell membrane. Off-spec material generally refers to a distillation product, such as product alcohol that does not meet a specification or a criterion in some respect. Example off-spec material includes, but is not limited to, butanol contaminated with impurities or butanol of lower concentration than that which meets specification. Example devices and equipment that can be subject to contamination include, but are not limited to, propagation vessels, fermentation vessels, distillation columns, beer columns, condensers, piping, fermentation/distillation machinery, and so forth.

In embodiments, a solution including lights and/or off-spec material and/or a process solvent stream is suitable for use as a terminal sterilant in a SIP process. In embodiments, a method in accordance with this disclosure is used to decontaminate only a portion of a fermentation or distillation system, e.g., this method is not implemented to clean all the equipment used to produce product alcohol from a renewable feedstock. This is to say that only a portion of a fermentation or distillation system's equipment is cleaned using lights/off-spec material. Lights may be a co-product or a by-product (e.g., a co-product that is unintended with little acceptable use given the system) generated by the fermentation. Lights may be included in a fermentation broth at a concentration that is not toxic to one or more contaminants present in the fermentation broth. In some embodiments, a fermentation process includes a decontamination procedure in which lights and/or off-spec material and/or a process solvent stream is applied as a sterilant solution is used in a SIP procedure, e.g., as a terminal sterilant, after the equipment has been cleaned using another procedure.

In embodiments, lights or off-spec materials are generated using fermentation/distillation processes. In some embodiments, lights and off-spec materials are produced from one or more of a fermentation or distillation process that are to be decontaminated. For example, the lights and/or off-spec material is included in the fermentation broth at a concentration that is insufficient to appreciably inhibit the microorganism, e.g., a butanologen, and/or a contaminant. In further embodiments, lights are an impurity or a co-product corresponding to a contaminant (e.g., microbial contaminant), that is to be minimized or eliminated. For example, ethanol produced by an ethanologen contaminant may be distilled in a lights column 446 included in a distillation system 404 to increase its concentration to a level that is toxic to ethanologens so it can be used to decontaminate equipment included in the fermentation and/or distillation system. In embodiments such as these, the lights/heavies/off-spec material can be collected in a solution tank 448 and used in a cleaning or sterilization process to decontaminate, for example a prop tank 214, a product tank 450, a distillation column, a product tank 452, a destination vessel 454, and so on including combinations of equipment.

In embodiments, a solution is implemented at a concentration that is effective to decontaminate equipment, but is at a concentration that is insufficient to inhibit or appreciably inhibit a microorganism producing fermentation product, e.g., butanol. Butanol that is a sufficient concentration to minimize contaminants, but is insufficient to inhibit or appreciable inhibit butanologens can be used to decontaminate equipment.

Off-spec alcohol can be suitable for use, although its associated fermentation or distillation process is contaminated above an acceptable threshold, because it is distilled a temperature that is effective to minimize contaminants (kill-off the contaminant) or it contains lights and/or off-spec material at a concentration that is toxic to one or more contaminants or potential contaminants present in the fermentation system. Although the lights, heavies and/or off-spec material can originate from a contaminated process or one that subsequently becomes contaminated, in additional embodiments, the lights, heavies, and/or off-spec material, e.g., off-spec butanol, originates from another production line. In another example, lights, heavies, or off-spec material may originate from another production line at the same facility or site.

As is to be appreciated, off-spec material can refer to product that is off-spec for the fermentation/distillation processes or equipment being decontaminated or it can refer to material that is off-spec for another fermentation/distillation process, e.g., a different fermentation/distillation product that does not meet specification for that other process. It will be apparent that the foregoing is applicable to lights produced from other processes.

At times one or more processes or equipment included in fermentation or distillation systems can become contaminated with a contaminant that inhibits production of fermentation product or competes with microorganisms for fermentable carbon substrate. For example, a propagation tank can become contaminated with a bacterium that generates an impurity, e.g., lactic acid. While some contamination may be tolerable, contamination can build-up to a level that impacts production. Contaminants can build up in recycled fermentation broth over multiple fermentations to a level that is not tolerable for production of the product alcohol. Impurities produced by contaminants in some embodiments are toxic to the microorganism above a particular level. Lactic acid, for instance, can be toxic to butanologens.

Buildup of contaminants can diminish production of product alcohol, increase co-product production (intended or unintended) in excess of a predetermined ratio, and so on. For example, an ethanologen in a butanol fermentation consumes fermentable carbon substrate that otherwise would be available to butanologens and generate ethanol in excess of predetermined ratio. In embodiments, cleaning or sterilization is reiterated until the equipment reaches an acceptable level of cleanliness. For example, the method can include reiterating the cleaning until the equipment reaches an acceptable level of cleanliness. In the previous embodiment, an acceptable level of contamination can correspond to a level at which a contamination by a microorganism that produces a minor co-product maintains production of that co-product at, substantially at, or below a ratio.

Lights and/or off-spec material can be toxic to a wide range of contaminants. In particular, lights and off-specification product may exhibit toxicity to contaminants because they are included at a concentration that is greater than one or more of their, respective, concentration in fermentation broth, mash, liquid-liquid extractant (e.g., COFA), or fermentation product that is a feedstock for distillation (distillation feedstock). The temperature of the lights, heavies, and/or off-spec material and/or process solvent stream can be selected to aid cleaning, increase the lights/off-spec materials and/or process solvent stream efficacy, and so forth. For example, one or more heaters (one is referenced as 456) are included to heat the lights, heavies, off-spec material and/or process solvent stream to a temperature that is operable to minimize/eliminate a contaminant. Moreover, in some instances, the lights or off-spec material's concentration is tailored so that it is non-toxic or not appreciably toxic to a microorganism, e.g., a butanologen. In other instances, the lights/off-spec material's concentration is selected so it is toxic to some contaminants but not to a microorganism that produces co-product. Thus, for example, a solution including the lights, heavies, off-spec material or combinations thereof can include lights, heavies, an/or off-spec material that is toxic to contaminants, but is substantially benign to microorganisms generating fermentation product and/or co-product, e.g., it does not appreciably reduce the population of an intended microorganism in a fermentation broth.

With continued reference to FIG. 4, in embodiments, a facility, such as facility 100 illustrated in FIG. 1 that includes the fermentation system 102 and a distillation system 104, includes a cleaning system 458 configured to provide solution for decontaminating the fermentation or distillation systems or portion thereof.

As illustrated, the cleaning system 458 includes a solution tank 448 configured to store the solution for use. In embodiments, the solution tank 448 is coupled to a lights column 446 included in a distillation system, such as system 104. In this manner, lights, heavies and/or off-spec material can be separated from a stream of distillation product, e.g., butanol that meets specification (on-spec), and transferred to the storage tank 448 configured to store the solution for subsequent use. For example, lights and off-spec are obtained from a common purge stream from the lights column 446. In embodiments, separation comprises distillation, although other separation technologies can be implemented in additional embodiments.

As illustrated in FIG. 4, the cleaning system 458 including the solution vessel is fluidly coupled to the lights column using piping, pumps and so forth for transferring the lights for storage. In embodiments, the solution tank is coupled to one or more of a propagation tank, a product tank, a fermentor, a destination vessel, another portion of a fermentation system or a distillation system (e.g., a distillation column). One or more heaters are included in the cleaning system in embodiments to increase the efficacy of the solution in a CIP or SIP applications.

The cleaning system can include a mixing tank for mixing the solution. In embodiments, the cleaning system, e.g., the mixing tank, is configured to incorporate one or more of additives, cleaning agents, defoamers, surfactants, wetting agents, antibacterial agents, antibiotics, and so on with the solution. In an example, the mixing tank is configured to dilute the lights or off-spec material prior to use. For example, the mixing vessel is configured to mix a cleaning agent with the lights, heavies, off-spec material and combinations thereof to promote decontamination.

In embodiments, the solution comprises up to fifty percent (50%) or up to approximately fifty percent (50%) butanol by weight, up to thirty percent (30%) or up to approximately thirty percent (30%) ethanol by weight. In additional embodiments, the solution comprises up to ten percent (10%) or up to approximately ten percent (10%) butanol by weight; or up to seven percent (7%) or up to approximately seven percent (7%) ethanol by weight; and combinations thereof. The solution can comprise 1%, 5%, 10%, 15%, 20%, 25%, 30%, 35%, 40%, 45%, or 50% butanol, or any number in between 1-50% butanol. The solution can comprise 1%, 5%, 10%, 15%, 20%, 25%, 30% ethanol, or any number in between 1-30% ethanol. Example solutions include but are not limited to solutions containing co-products, off-spec butanol including 1-butanol, 2-butanol, isobutanol, tert-butanol, and combinations thereof.

The cleaning system can be configured to implement the solution using a variety of approaches. Example cleaning approaches and devices include, but are not limited to, spray ball washing, impingement washing, vessel soaking, SIP, and combinations thereof. In embodiments, a clean system is configured to implement a variety of decontamination approaches. For example, a cleaning system is configured to vary decontamination procedures on a periodic basis, responsive to determination of a condition, and so on. For example, a cleaning system is configured to implement a more robust cleaning or sterilization procedure responsive to a determination that impurities have increase beyond a threshold. In an embodiment, cleaning comprises A) performing one or more of: a CIP procedure that comprises at least one of spray ball washing, impingement washing, or a vessel soak and subsequently performing a SIP procedure; B) performing a CIP procedure without performing an SIP procedure; C) performing a wash with water and subsequently performing a SIP procedure; D) performing a wash with water and immersing at least a portion of the equipment as part of a SIP procedure; or combinations thereof including repeating at least one of A, B, C, or D until the equipment reaches an acceptable level of cleanliness. In some embodiments, at least a portion of the solution remains on a decontaminated surface to minimize potential contamination that may occur from termination of the cleaning or sterilization till subsequent use for fermentation/distillation. For example, a caustic solution or acidic solution is allowed to remain on a decontaminated surface to minimize potential contamination.

In some embodiments, the cleaning system 458 is configured to recycle solution that has been used to decontaminate equipment. A cleaning system can be configured to recycle the solution a predetermined number of times or a number of times based on existence of a condition. An example of the latter situation is that the clean system is configured to recycle solution until it becomes contaminated with impurities, it efficacy drops, the concentration of lights/off-spec material in the solution drops below a threshold, and so on. For example, an infrared detector or other monitoring device is used to determine if the solution is below a threshold at which it is suitable for use.

In embodiments, used solution can be combusted to produce energy for the fermentation or distillation processes or a facility containing the system. For example, the solution may be reused until it is no longer suitable for use in decontamination at which time it is transferred for combustion. In other examples, solution is used a single time and then combusted for energy by a facility including the system.

In embodiments, used solution is recycled for distillation into distillation product, e.g., on-spec product. For example, solution used to decontaminate a distillation column, such as a lights column can be processed into on-spec product alcohol. In some embodiments, solution is incorporated with fermentation product fed to a distillation column until the distillation column achieves a steady state. Off-spec material, for example, can be mixed with fermentation product that is a feedstock for a distillation system or column until the column achieves steady state production of distillation product that meets specification. It should be apparent that recycled solution can be mixed with fermentation product to serve as a feedstock when the column is brought on line.

As mentioned generally above, the cleaning system 458 is configured to heat the lights/off-spec material and/or process solvent stream substantially to a predetermined temperature that is effective to minimize contamination in some embodiments. The predetermined temperature can be sufficiently high to clean equipment which it contacts of contaminants. For example, a cleaning system 458 includes one or more heaters 456 to raise the solution's temperature to effectively eliminate or kill-off microbial contaminants on a surface of the equipment that comes in contact with one or more of biomass, mash, fermentation broth, extractant, fermentation product, distillate, and combinations thereof. Additionally, the purge stream may include lights/off-spec material that is of sufficient concentration to minimize microbial growth. For example, the solution may contain butanol at sufficient concentration so it is effective to minimize microbial contaminants if applied at the predetermined temperature to a surface of equipment to be cleaned.

The operating parameters of the cleaning system may be selected or predetermined to ensure various surfaces included on the equipment reach the sufficiently high temperature to minimize contamination. Example factors that impact the cleaning system's ability to decontaminate the equipment's surfaces include, but are not limited to, the predetermined temperature, solution composition, amount of solution used, the equipment's surface porosity, presence of additives in the solution (e.g., detergents, wetting agents, dispersants, and so on), equipment surface area, whether agitation is to be used, application rate, spray pressure, cleaning technique (e.g., spray ball washing, immersion), combinations thereof, and so forth.

In embodiments, the procedure, approach, or technique implemented by the cleaning system 458 varies depending on a factor associated with the equipment being cleaned. For example, a high concentration of impurities (above an acceptable level) can be a factor that triggers a more intensive cleaning procedure in comparison to the presence of an impurity or co-product that is closer to the acceptable level than the high concentration. Other factors include a ratio of ethanol produced in comparison to butanol or other formation product, occurrence of a rejected batch, production of acetic acid, reduced product alcohol production, and combinations thereof. Example decontamination approaches include a variety of cleaning or sterilization techniques. For example, the cleaning system 458 can be configured to A) performing one or more of: a CIP procedure that comprises at least one of spray ball washing, impingement washing, or a vessel soak and subsequently performing a SIP procedure; B) performing a CIP procedure without performing an SIP procedure; C) performing a wash with water and subsequently performing a SIP procedure; D) performing a wash with water and immersing at least a portion of the equipment as part of a SIP procedure; or combinations thereof including repeating at least one of A, B, C, or D until the equipment reaches an acceptable level of cleanliness. Those of skill in the art will appreciate that use of a solution raised to a predetermined temperature can be used in conjunction with the other decontamination techniques, including but not limited to the contamination mitigation using lights/off-specification distillation products described above.

In embodiments, at least a portion of the solution is left as a residue on a surface of the equipment being decontaminated. For example, a spray ball can be used to spray solution on interior surfaces of a fermentor to minimize the likelihood of contamination until the fermentor is used in a subsequent process. In embodiments, caustic or acidic solution is permitted to remain on one or more surfaces to prevent or minimize potential contamination.

Having described fermentation, extraction of fermentation product and decontamination techniques implementing lights/off-spec material, separating fermentation product containing extractant (rich extractant) from the aqueous phase is examined in further detail. Example separation techniques include, but not limited to, siphoning, decantation, centrifugation, using a gravity settler, and membrane-assisted phase splitting. Recovery of fermentation product from the extractant organic phase can be done using a variety of methods including but not limited to, distillation, adsorption by resins, separation by molecular sieves, and pervaporation. Specifically, distillation can be used to recover the butanol from the butanol-containing organic phase.

ISPR System Decontamination

Figure 5A:
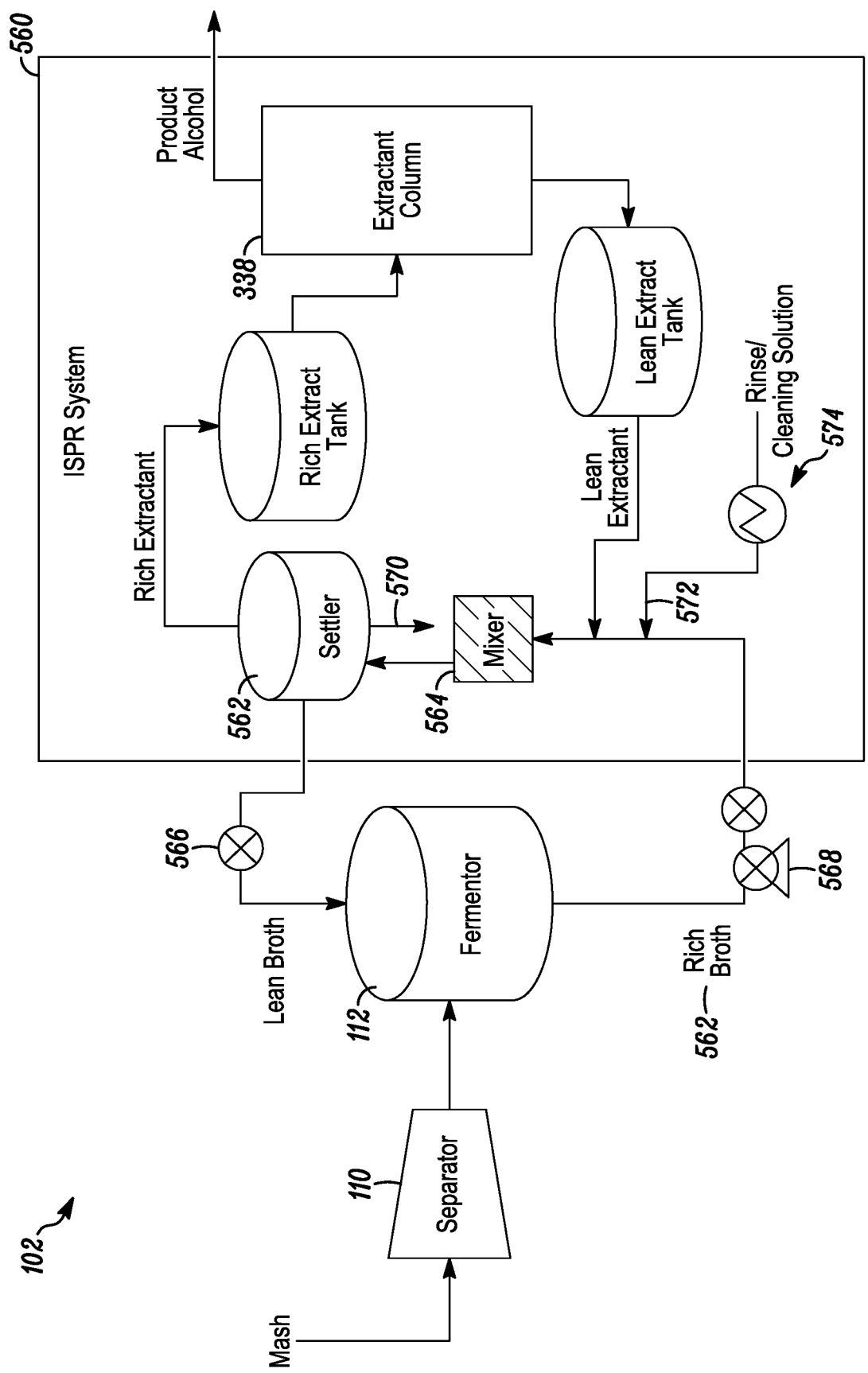
FIG. 5A illustrates a fermentation system including an ISPR system configured to implement an isolated decontamination procedure.

Referring now to FIG. 5A and is generally illustrated in FIG. 1, in embodiments a fermentation system, such as system 104, includes a ISPR system 560 that produces fermentation product by recovering it from broth through use of an extractant, such as an organic solvent as discussed above. As illustrated the ISPR system 560 is constructed to use COFA to recover isobutanol from the fermentation broth 562.

Decontaminating the ISPR system 560 can be problematic because COFA and other extractants can react with some cleaning materials. ISPR systems, in embodiments, include a variety pipes and equipment to extract fermentation product from the broth 560 and separate it from the extractant. The ISPR system 560 includes equipment with numerous surfaces that can become contaminated with, for example, fermentation solids, extractant residues, impurities, and so on. For example, a mixer 564 and a settler 566 included in the ISPR system 560 have interior surfaces that can become contaminated. COFA, an example extractant, can saponify to form crude soaps on the surface of the mixer 564 and settler 566 in the presence of caustic material. These crude soaps can be difficult to remove from interior mixers, settlers, and so forth included in the ISPR system 560. Although caustics are effective cleaning agents for other subsystems, this tendency to form crude soaps with fatty acids may preclude its use in a systems that implement a fatty acid extractants.

As noted above with respect to FIGS. 3A-C, ISPR systems can be configured in a variety of ways. In examples, extractant is added directly to the fermentor 112. In other examples, fermentation systems include an external loop (e.g., a loop that is external to the fermentor) that is configured to bring extractant into contact with broth to recover the fermentation product. In examples such as this, the extractant and broth are mixed downstream of the fermentor and the resultant rich extractant is separated from the broth so the thin broth can be recycled and the extractant processed to remove the fermentation product. While efficient for separating broth from extractant, centrifuges and other separation units can be difficult to decontaminate. Accordingly, methods, techniques, approaches, systems, and devices for decontaminating ISPR systems are now discussed in further detail.

In embodiments, decontamination of the ISPR system 560 includes isolating the ISPR system from other portions of a fermentation system 102. For example, the ISPR portion can be isolated from other portions of the fermentation system 102, e.g., the fermentor, used to generate fermentation product from feedstock material, e.g., biomass. The ISPR system 560 can be isolated from distillation equipment as well or independently isolated from the distillation system 102 while being in fluid connect with other portions of the fermentation system 104. In these embodiments, the ISPR portion is isolated from other portions of the fermentation system 104 so different decontamination procedures can be used, e.g., incompatible cleaning procedures. In embodiments, isolating the ISPR system 560 comprises closing one or more valves (one valve 566 is referenced) that block fluid from passing between the ISPR system 560 and another portion of the fermentation system, e.g., the fermentor 112. In other embodiments, the ISPR can be isolate through the use of a check valve, or for example, by ceasing operation of a device, such as a pump 568 that is operable to transfer broth from the fermentor 112 through a cooling loop and so forth. In the previous example, the non-operating pump isolates the ISPR from the fermentor 112 where the pressure in the fermentor 112 is not sufficient to pass through the pump. By isolating the ISPR system 560 from the fermentor 112 so fluid cannot pass, a caustic solution can be used to clean the fermentor 112, but it is prevented from contacting extractant in the ISPR system 560 that otherwise would saponify in the presence of the caustic solution. By isolating the ISPR system 560 from other portions of a fermentation system 102, decontamination techniques that are effective for one portion of the fermentation system can be used even though that technique is incompatible for decontaminating another portion of the fermentation system 102 or decontamination technique used to clean the other portion, i.e., the non-ISPR system portion.

In some embodiments, ISPR system 560 is constructed to rinse a portion of the ISPR system (e.g., the mixer 564, a settler 566) or the entire ISPR system with water. For example, a mixer or settler in the ISPR system 460 includes a spray ball washer to remove residues, solids, and so on that may be present on surfaces of the ISPR equipment. A spray ball washer can be used to spray interior surfaces of the settler 566 configured to coalesce rich extractant (extractant including product alcohol) that was mixed with broth. Immersion and other application techniques and combinations thereof can be used to decontaminate the ISPR system as well. It should also be apparent that agitation can be implemented to increase the rinse/cleaning solution's efficiency. For example, an agitator in a settler is used to mix the caustic solution during a decontamination cycle.

Using a water rise after isolating the ISPR system 560 may remove extractant residue on one or more surfaces of the settler, a mixer or other equipment included in the ISPR system 560. The rinse water, and any removed material can be flushed out a low point drain 570 for disposal, recycling, or purification for use in another portion of the facility. Although rinse water can be introduced in a variety of locations in the ISPR system 560, in embodiments, rinse water is introduced upstream of a point at which extractant is introduced, e.g., point 572. Introducing water and/or cleaning solutions upstream of a point at which extractant is introduced permits removal of extractant, broth, fermentation solids, and the like that can collect adjacent the introduction point to improve the effectiveness of the decontamination procedure.

The ISPR system 560 can include a heater (such as heater 574) to raise the rinse water's temperature to increase is efficacy for removing extractant and/or contaminants. In embodiments, the rinse water includes additives, such as surfactants, wetting agents, detergents, dispersants, and the like for increasing its cleaning efficiency.

In embodiments, a caustic solution is introduced to the ISPR system to decontaminate the surfaces of the ISPR system with which it comes in contact. For instance, the caustic solution is introduced subsequent to a water rinse to decontaminate the equipment, e.g., the equipment surfaces that contact extractant/broth during use. Introducing caustic solution subsequent to a rinse can minimize or eliminate saponification of extractant (COFA) that may be present. For example, the rinse may be effective to remove the extractant or substantially all extractant residue that clings to the surface of the ISPR equipment after use. The caustic solution, can be sufficiently strong to decontaminate the surface of the equipment of contaminants that otherwise would compete with microorganisms producing fermentation product for fermentable carbon substrate or otherwise inhibit the microorganisms. Decontaminating ISPR equipment is important because, in some instances, lean broth and/or lean extractant is recycled through the fermentation system and may represent a potential contamination source. In embodiments, a two percent (2%) by weight caustic solution is used to decontaminate the ISPR portion of the fermentation system. In embodiments, the caustic solution comprises a two percent (2%) by weight alkaline solution. The caustic solution comprises a two percent (2%) by weight sodium hydroxide solution or a solution that is approximately two percent (2%) by weight sodium hydroxide solution in examples in accordance with the present disclosure. The ISPR system 560 can be configured to introduce caustic solution by a variety of techniques, including but not limited to, spray ball application, immersion, and so on.

In embodiments, a method includes introducing an acidic solution to decontaminate the ISPR of contaminants and/or neutralize any caustic solution or caustic solution diluted with rinse water that may remain on the equipment's surface. In some embodiments, an acidic solution is introduced after the caustic solution. For example, sulfamic acid is used to decontaminate and/or neutralize any residue on the ISPR equipment. Other example acids suitable for use include, but are not limited to, phosphoric acid, citric acid, sulfamic, butyric acid, and the like. Sulfamic acid can be applied periodically, such as part of de-inventoring the ISPR system or a portion thereof, e.g., settlers, mixers, centrifuges, pumps, and so on. Sulfamic acid solution can be used in conjunction with a caustic cleaning solution as part of a larger decontamination process or the two can be used at different times based on various factors including, but not limited, an amount of contamination present, a type of contamination, existence of a rejected fermentation batch, decreased product alcohol production, reduced extraction efficiency, a detected criterion, and so on. As should also be apparent, an cleaning procedure can commence with an acidic wash or rinse initially to clean/remove extractant from interior surfaces of ISPR equipment prior to additional cleaning steps, e.g., rinses, detergent washes or rinses, washes, caustic washes, and so forth.

In some examples, a two percent (2%) by weight acidic solution is used. For instance, a two percent (2%) by weight sulfamic acid solution is introduced as a spray by a spray ball. In other embodiments, the acidic solution comprises approximately two percent (2%) sulfuric or approximately two percent (2%) phosphoric acid by weight. Other cleaning techniques can be used as well. In this and other embodiments, the acidic solution is introduced downstream of a point at which extractant is introduced into the ISPR system.

The ISPR system 560 can be configured to perform an acidic solution rinse after rinsing the ISPR system with water, introducing a caustic solution, rinsing the ISPR system with water and then applying the acidic acid solution. An example cleaning procedure may be to deinventory the ISPR system including any mixers/settlers. This cleaning procedure can, for example, include the following: a) water rinse the equipment, e.g., the mixer 564 so the rinse water passed through the mixer to the settler by introducing the water upstream of a lean extractant introduction point, e.g., a point at which COFA is introduced to the ISPR system; b) clean the ISPR equipment by washing it with a two percent (2%) sodium hydroxide solution by weight solution, with or without agitation. The cleaning can be performed by an immersion wash or other cleaning technique; c) water rinse the equipment: this water rinse can be used to reduce any sodium hydroxide residue, contaminants, solid particles, and so on from the equipment; d) clean the ISPR equipment by rinsing it with a two percent (2%) by weight sulfamic acid solution, with or without agitation. In embodiments, at least a portion of the sulfamic acid solution is allowed to coat the surface of the equipment while excess sulfamic acid is drained through a low point drain on the equipment, e.g., a settler. In other embodiments, such as where a sulfamic acid wash is utilized, a terminal caustic wash or rinse is used and caustic solution is permitted to remain on the surface of the equipment.

The water rinse between introduction of the caustic and acidic solutions may prevent the caustic and acidic solution from reacting, aid in contaminant removal (removal of solids loosened by the caustic solution, saponified extractant), and so on. In embodiments, the acidic solution or a portion of the solution remains on the surface as a residue to minimize contamination, e.g., contaminants growing on the surface, until the equipment is reused. For example, while acidic solution may be remove via a low point drain such as drain 570, acidic solution that clings to the surface of the equipment may be permitted to remain, e.g., the acidic solution residue is not rinsed with water, until used. In this manner, the acidic solution can function as a terminal sterilant between batches. In other embodiments, the sequence of caustic and acidic solution treatments is reversed, e.g., acidic solution is implemented prior to the caustic solution.

Configuring a fermentation and ISPR to permit solution removal via the low point drain without using a pump configured to transfer lean broth also prevents or minimize cleaning solution contaminating recycled fermentation broth. An ISPR system configured in this manner can minimize the likelihood of extractant that remains in recycle broth saponifying in the pump as it comes in contact a caustic solution, contamination of the broth with cleaning solution (acid solution), rinse water, rinse water additives, and so forth. Although the cleaning solution, rinse water and so forth is drained from ISPR system it can be purified or utilized in another process, to minimize waste water.

The decontamination procedures can be repeated based on a predetermined schedule. In other examples, one or more of the water rinses and or introduction of cleaning solutions (caustic/acidic solution) and combinations thereof can be repeated based on an occurrence of an event. For example, one or more of a water rinse, caustic solution introduction followed by a water wash, and an acidic rinse are repeated until a monitoring system determines the ISPR system 560 has achieved an acceptable level of cleanliness.

In instances, the ISPR system includes a cleaning system for preparing; storing; purifying, the various rinses, solutions (caustic and acidic); and so on. In other instances, a cleaning solution is prepared in situ. A caustic solution, for instance, is prepared in a settler or mixer to be decontaminated. Further, the cleaning solutions and rinse water can be reused for a predetermined number of times or be reused until it fails to meet a predetermined criterion (e.g., exceeds and acceptable level of solids, decreased in causticity or acidity, and so forth). For example, a caustic solution is reused to clean four settlers included in the ISPR system. At that point, the solution can be purified, rejuvenated, reused for another process, or disposed of.

Figure 5B:
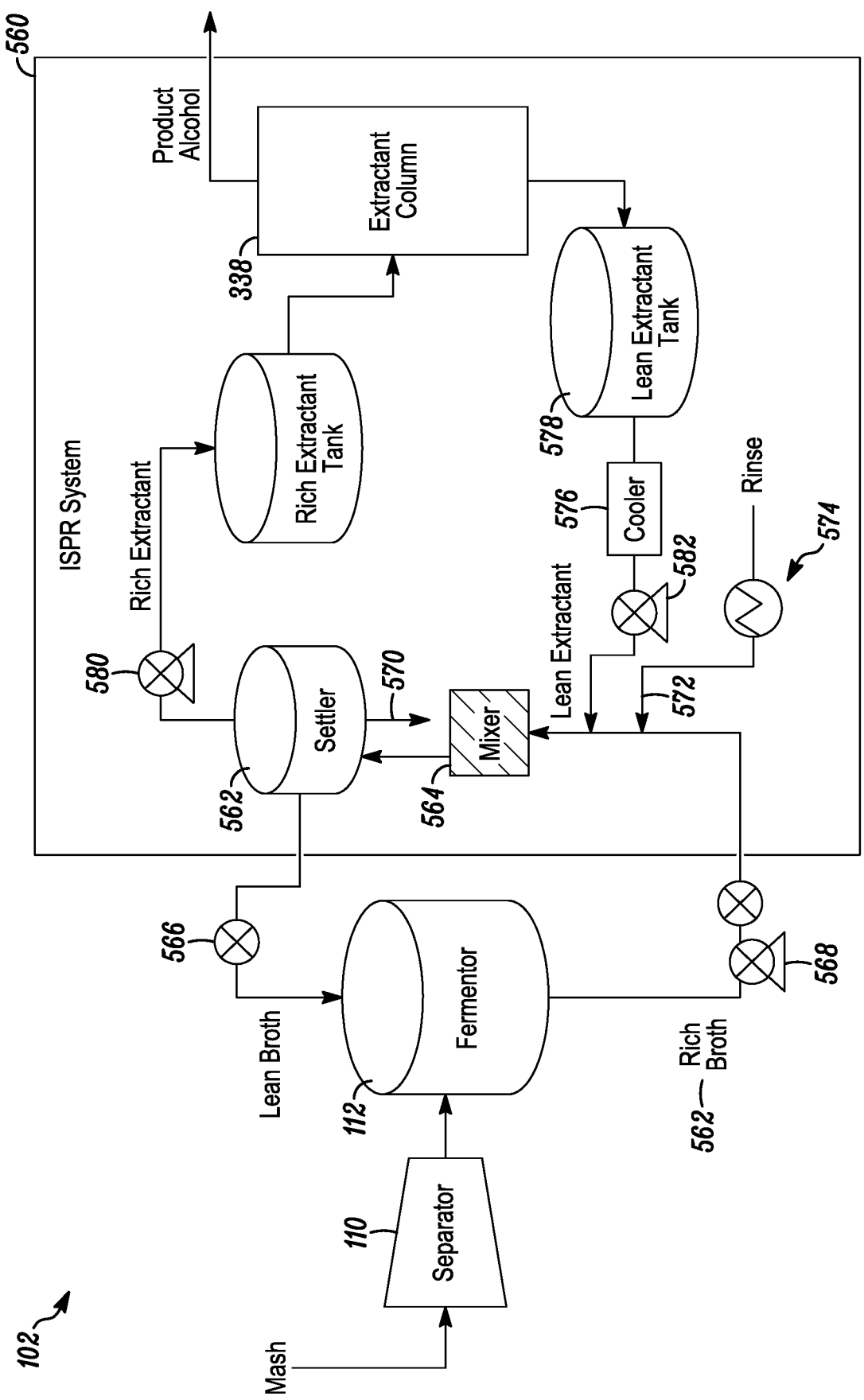
FIG. 5B illustrates a fermentation system including an ISPR system configured to implement heated extractant for decontamination.

Referring now to FIG. 5B, FIG. 5B illustrates an ISPR system 560 that is substantially similar to the ISPR system 560 of FIG. 5A. In the embodiment illustrated in FIG. 5B, the ISPR system is configured to use heated extractant as a cleaning agent. In embodiments such as these, the ISPR system 560 heats the COFA to a temperature that is sufficiently high to decontaminate at least a portion of the ISPR system, e.g., the mixer 564 and the settler 566 are heated to a temperature sufficient to kill wild-type yeast like ethanologens. While the ISPR system can implement active heating to raise the temperature of the COFA, in some embodiments, heating is achieved by passive heating, e.g., by not cooling the COFA as it passes through the system (not using cooler 576 to maintain the COFA at its typical use temperature). In this way, the COFA temperature rises above a temperature at which it is implemented to extract fermentation product (e.g., non-decontamination use of the ISPR system 560). In the previous example, the temperature of the COFA during decontamination can rise above seventy-five degrees Celsius (75° C.) to minimize or eliminate any contaminant by killing off any biologically active contaminants, e.g., lactic acid producing microorganisms. In additional examples, the temperature of the COFA in a storage vessel or tank is maintained at a temperature that is sufficient to minimize contamination, keep the extractant sterile (e.g., 80° C. for COFA), or above a temperature at which it is implemented in the ISPR system, e.g., a temperature at which the COFA is implemented in normal operation of the ISPR system 560. The sufficiently high temperature may be selected to promote decontamination while remaining below a temperature at which the extractant is subject to appreciable thermal degradation.

In additional examples, the pump rates of one or more pumps included in the ISPR system 560 are set to achieve a matched feed/removal rate. An example of the foregoing is to set a rich COFA pump 580 and a COFA feed pump 582 to operate at a rate that results in a substantially continuous flow of heated COFA through the mixer/settler to heat the surfaces of the equipment that it contacts. Configuring the pumps 580, 582 to operate in this manner may promote rapid heating, minimize the likelihood of the COFA cooling below the sufficiently high temperature, and circulate through the equipment at rate that ensures the extractant is at or above the sufficiently high temperature, and so on.

In an embodiment, the ISPR system is configured to perform a decontamination procedure that includes deinventoring the ISPR equipment, e.g., the mixer/settler system, by using the following steps: a) Shutting down a cooler (e.g., COFA cooler 576) used to reduce extractant temperature during normal operation; b) feeding the mixer and/or settler with COFA that is heated/not cooled thorough the extractant feed point; c) matching the input/output rate of the extractant to raise temperature of the equipment to a temperature that is sufficient to decontaminate the equipment, e.g., the surface of the equipment that comes into contact with the COFA. Optionally, deiventoring the equipment on completion of a decontamination through a low point drain on the equipment, e.g., a drain on a settler or the last vessel/piece of equipment to be cleaned. Optionally, rinsing the equipment with water to minimize or reduce any COFA present on the equipment's surface. For example, a water rinse is used to eliminate any residue, particles and so forth that remains on the interior surfaces of the equipment. A spray ball or other technique can be used to apply the rinse. In some examples, the rinse water can be heated to increase its solubility, etc. as described previously.

As is to be appreciated, the techniques, approaches, devices, systems, and so forth described in conjunction with FIG. 5B can be implemented with those discussed in conjunction with those referenced in FIG. 5A or in FIGS. 1-4. For example, decontamination using hot extractant (COFA) is performed on a schedule (every batch, every other batch, every forth batch an so on) while the caustic/acid wash decontamination is performed on a longer cycle (e.g., every ten batches) or in response to a predetermined criterion, e.g., the ISPR system drops below an acceptable cleanliness level.

Further, the various procedures or steps of the procedures can be repeated or reiterated multiple times based on a predetermined schedule or until the occurrence of an event, such as meeting a pre-specified criterion, e.g., achieving a particular level of cleanliness. Additional ISPR decontamination or cleaning techniques can be implemented in conjunction with those described in FIGS. 5A and 5B as will now be described below in further detail. It is to be apparent that the approaches, techniques, systems, solutions, and so forth can be implemented with those described throughout this document, including but not limited to those described in conjunction with FIGS. 5A and 5B

Product Recovery Decontamination/Extractant Recovery

Figure 6:
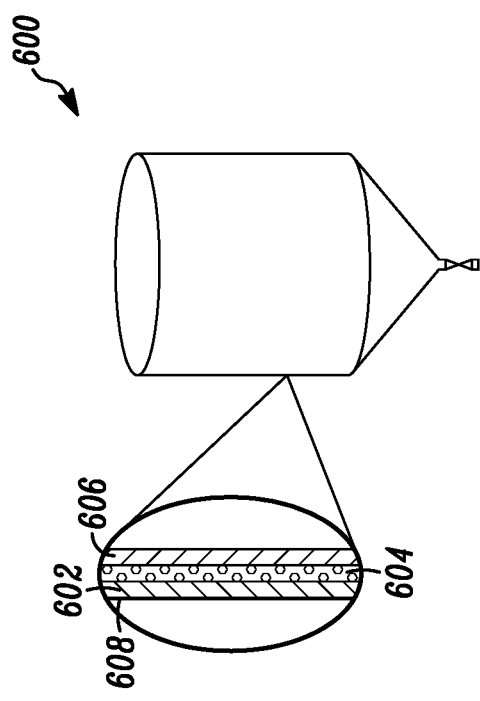
FIG. 6 illustrate an embodiment of a tank contaminated with a variety of contaminants.

Referring to FIG. 6, embodiments of fermentation systems, product recovery cleaning systems, methods, approaches, and so forth are described in additional detail. Further, approaches, techniques, methods and so forth for recovering extractant are also described. For examples, methods in accordance with this disclosure permit increased extractant recovery which reduces expense and waste disposal. Product recovery, such as in situ product recovery (ISPR) using liquid-liquid extraction technology as described in detail above, can implement extractants that pose decontamination issues. Recovery of extractant from equipment, such as a surface that comes in contact with broth and/or extractant is also discussed. Recovering extractant for reuse or inclusion in a product stream can diminish waste issues, increase co-product production, and so on.

Various extractants, such as COFA, can be used to recover isobutanol from fermentation broth. Although useful as an extractant, chemical cleaning of a COFA from equipment is difficult. COFA, and other extractants, can pose decontamination issues not only by themselves, but in combination with solid and/or microorganism contaminants because it clings to surfaces of equipment and it can form an oily or waxy-type residue or film that adheres to equipment surfaces. For example, the interfacial tension between the COFA and a water based cleaning solution may form a barrier that prevents dispersion of the COFA in the water. Additionally, extractants such as COFA do not respond well to some solutions used to clean equipment, e.g., caustic or acid cleaning solutions. Mechanical and heat cleaning procedures may be impractical due to cost, contamination complexity, downtime issues, complex interior surfaces (e.g., static mixer surfaces), expense, and so on.

In examples, extractant such as COFA adhered to interior surfaces of equipment is considered a contaminant, even though once recovered it can be processed for reuse or supplied as a co-product. In addition to being difficult to remove itself, COFA may coat other contaminants. COFA residues can prevent cleaning solutions from reaching other contaminants or the COFA may cause contaminants to cling to a surface, such as when the equipment is being drained. COFA, for example, prevents some decontamination solutions from contacting contaminant microorganism to biologically deactivate them, e.g., kill them. Disposing of COFA as waste may increase expense and waste an otherwise valuable material. Further, if an incompatible cleaning solution is used, COFA can react to form a product that is less valuable, e.g., esterified to crude soaps.

Referring now to FIG. 6, a tank 600 or vessel is illustrated as an example of various decontamination issues posed by extractants such as COFA. Although a tank is illustrated, other components, equipment, devices included in fermentation systems experience similar contamination and cleaning issues. Static mixers and settlers included in a product recovery system may become contaminated with COFA. Static mixers, for instance, are problematic to clean as they have complex internal baffles that have complex geometries.

As illustrated, contaminants (e.g., solids 602, microorganism contaminants 604, COFA 606) can cling or adhere to surfaces of the equipment that contact fermentation broth/extractant, e.g., a metal wall of the tank 608. In embodiments, the surface is a metal surface, such as a stainless steel surface, or other metal surface suitable for use in a fermentation system. Solid particulate matter, such as from biomass, fermentation solids, microorganisms (e.g., yeast) can cling to the tank's surface 608. Other contaminants can build-up on the surface of the tank 600 as well. For example, COFA can adhere to a surface of equipment when the equipment is deinventoried for cleaning or maintenance. Microorganism contaminants (e.g., environmental bacteria) can also adhere to the tank or to solids on a surface of the tank and other materials on the surface of the tank. COFA that coats these contaminants can prevent proper cleaning as some cleaning solutions are not able to contact these contaminants, due to the extractant. Although distinct solids/contaminate microorganism/COFA layers are illustrated, it is to be understood that multiple layers can be formed, layers can be formed of multiple components (e.g., solids, contaminate microorganisms, other contaminants), and so forth. For example, COFA can form an "oily" residue that is difficult to clean.

Accordingly, methods, techniques, approaches, systems, principles, and devices are described for decontaminating equipment, fermentation systems, fermentation systems that include product recovery systems, and so on. In embodiments, the techniques, approaches, methods, principles described herein can be used in conjunction with or in place of those described in relation to those referenced in FIGS. 3A-5B. For example, the solutions described herein can be generated or prepared using equipment described with reference to FIG. 4.

In an embodiment, a method for decontaminating a fermentation system includes generating a solution. A solution is generated, for example, by mixing an effective amount of an interfactant or a solubilization agent in an aqueous solution for use in decontaminating equipment. An interfactant is capable of altering the effective interfacial tension between COFA and water and due to including hydrophilic and oleophilic moieties, it can bridge between extractant and water. In embodiments, a sufficient concentration and/or an effective amount of interfactant is an amount or concentration to adjust the surface tension/interfacial tension of the solution with respect to the extractant. For example, an interfactant is selected at least in part because it exhibits a surface tension that does not cause air bubble entrainment, it is effective to form a dispersion with extractant, and so forth. In some embodiment, an interfactant is at least in part selected based on its anti-foaming property. Although interfactants are discussed herein, it is to be apparent that the considerations and properties of solubilization agents are similar to those of interfactants as understood by those of ordinary skill in the art. In an example, the interfactant is a choline salt that is included in sufficient quantity in the solution to form a dispersion, e.g., a heterogeneous dispersion, with extractant. For example, the solution forms a dispersion that includes water and interfactant from solution with extractant that is removed from a surface of a piece of equipment. The solution can be mixed in, for example, solution tank 448 or destination vessel 454.

Example choline salts include but are not limited to choline citrate, choline hydroxide, phosphatidylcholine, bitartrate, choline chloride, choline acetate, a choline fatty salt, choline oleate, choline stearate, choline sulfate, choline linoleate, choline isobutyrate, or a combination thereof. Other interfactants can be used as well, examples include, but are not limited to, urea, alkyl urea, a quaternary ammonium salt, a polyether glycol, non-ionic surfactants such as Tergitol™ (Dow Chemical Company, Midland Mich.), ethoxylate, trialkylphosphate, tetramethyl urea, tetraethyl urea, a short chain phosphate, an alkyl phosphate, isobutyrate, a bridging compound, monoalkylphosphate, dialkylphosphate, or a combination thereof. These interfactants can be combined with choline salts as well and vice versa.

The number and/or length of alkyl substituents in the interfactant can impact its hydrophilic/oleophilic properties. More or longer alkyl groups can increase the oleophilicity of phosphate esters. The solubility of tri-organo phosphates decreases with the increase of radical molecular weight. Trimethyl- and triethyl-phosphates are water miscible. The solubility of tripropyl phosphate is six-thousand four-hundred fifty milligrams per liter (6450 mg/L) at twenty-five degrees Celsius (25° C.), while tributyl phosphate's solubility is approximately one thousand milligrams per liter (1000 mg/L) at four degrees Celsius (4° C.). and decreases with temperature, achieving 2.85×10–4 mg/L at fifty degrees Celsius (50° C.).

In some embodiments, a short chain comprises a chain of two (2) carbons or less. In some embodiments, phosphate esters that are more thermophilic in comparison to other phosphate esters are more biocompatible with microorganisms, such as butanologens.

It is also to be appreciated that the solution may include additional chemicals, additives, and so forth. Example additives include dispersants, acids, bases, antimicrobial agents, antioxidants, antifungal agents, wetting agents, defoamers, dyes, surfactants (e.g., non-ionic surfacatans), surface tension modifiers, and so forth. For example, a solution may include an interfactant and a solubilization agent to recover and/or clean extractant from one or more interior surfaces on equipment that comes in contact with fermentation broth and/or extractant.

Interfactants can be selected based on a variety of factors. For example, interfactants that are hydrophilic, but include an oleophilic moiety may be selected. Interfactant selection can be tailored so the interfactant primarily remains in the aqueous phase, but is sufficiently oelophillic to remove extractant, adequately disperse the extractant, and so on. An example of the foregoing is a molecule that has one or more hydrophilic "ends" and one or more oleophilic "ends" so the interfactant can bridge between a primarily polar aqueous phase including water and extractant, such as COFA, that has non-polar/hydrocarbon properties. Those of skill will appreciate that the presence and extent of the different moieties, e.g., hydrophilic moieties, oleophilic moieties, on the interfactant can determine the effectiveness of the interfactant or a combination of interfactants to form a dispersion and exhibit properties that are beneficial for a particular configuration. An example of the foregoing is the extent to which the interfactant partitions into the organic phase, e.g., the extractant.

Solubilization agents can be selected based on similar rationales as those of interfactants with the solubilization agent being chosen to form a solution that permits extractant recovery and/or proper cleaning of equipment. Solubilization agents, similar to interfactants, can be chosen to permit effective recovery of extractant. Solubilization agents may be chosen based on the chemical structure of the extractant to be cleaned, equipment complexity, equipment operating parameters, to ensure proper cleaning, to ensure extractant is fully solvated, to permit efficient extraction/solution separation, and so forth.

Other interfactant properties of relevant include, but are not limited to, the interfactant's biocompatibility/tendency to act as a biocide, antioxidant, ability to partition into an extractant, pH, its ability to improve extractant product recovery efficiency, its ability to populate an interface between extractant and water, hydrophillicity, oleophilicity, affinity towards a fermentation product, and so on. For example, an interfactant is selected because it is effective for decontaminating equipment of one or more of extractants, contaminate microorganisms, its butanol extraction coefficient (Kd), its ability to partition between extractant and water, and the like.

In another instance, an interfactant is selected that when included in sufficient amount, e.g., at a particular concentration in a solution, the solution is capable of biologically deactivating a microorganism present on a surface to which it is applied, e.g., ability kills microorganisms when included in sufficient concentration. The interfactant can be selected because it is capable of, to some extent, partitioning into the extractant. For example, some interfactants, while being included in an aqueous phase, populate adjacent an interface between the aqueous phase and an organic phase, e.g., a phase that includes extractant. It should be apparent that an interfactant can be selected because it is sufficiently oleophilic to form a dispersion with the extractant, but not sufficiently oleophilic enough so the interfactant enters the organic phase in an appreciable amount (e.g., an amount that would cause the extractant to be bio-incompatible with a beneficial microorganism, e.g., a butanologen used in a butanol production line).

In the previous example, while interfactant is generated by mixing the selected interfactant with the water and additional additives, the interfactant can be added in an amount that allows it to populate the aqueous phase adjacent the organic or extractant phase without appreciably remaining in the water, e.g., the bulk or entirety of the water when the solution interacts with extractant residue. Put another way, the amount of interfactant can be selected so enough interfactant is present in the solution, e.g., the aqueous phase so it can migrate in the water to adjacent an interface between the water/extractant while remaining in the water. In the foregoing example, some of the interfactant can partition into the extractant, based on the extractant's properties, the properties of the interfactant (e.g., hydrophilic/oleophilic properties), the properties of any additives in the water, and so on.

In some examples, the concentration of interfactant in the solution is sufficiently high so that interfactant is not the limiting factor for dispersion formation, but its concentration is low enough to prevent interfactant from partitioning or otherwise entering the extractant in an amount that would cause the extractant (containing interfactant at another or second concentration) to become bio-incompatible with a microorganism present in fermentation broth, e.g., a genetically modified microorganism configured to generate butanol such as isobutanol.

In the previous example, some of the interfactant may enter the extractant or the organic phase. For example, as part of forming a dispersion, some interfactant that is originally included in an aqueous phase partitions or otherwise enters the extractant. In embodiments, the concentration of interfactant in the extractant is effective to cause the extractant to exhibit a variety of properties. For example, the interfactant is present in sufficient concentration or amount in the extractant to increase the capability of the extractant to extract butanol from water (e.g., fermentation broth) more efficiently. In situations such as this, the butanol partition coefficient (Kd) of the extractant/interfactant is greater or higher than the extractant without the interfactant.

In embodiments, generating the solution comprises adjusting the solution's pH. For example, a caustic can be added to raise the pH of the solution to a pH of nine (9) or greater, approximately nine (9), approximately nine (9) or greater, greater than twelve, approximately twelve (12), twelve (12). In embodiments, the solution's pH is selected to be, to approximately be, or greater than the pKa of the extractant. For example, COFA may have a pKa of approximately five (somewhat acidic). Thus, the solution may have a pH of approximately five (5), five (5), or greater than five (5).

It should be appreciated that extractants, and in particular extractants derived from biomass such as COFA, other corn derived extractants, fatty acids derived from other biomass, and so on can have different pKa values based on a variety of factors. Example factors include, but are not limited to, the chemical structure of the fatty acid, how the fatty acid was produced, other constituents present (e.g., presence of unconverted biomass oil), presence of additives in the extractant (e.g., antioxidants, antimicrobial agents) and so forth.

As will be explained in additional detail below, the pH of the solution in comparison to the pKa of the extractant can be tailored for a variety of rationale. For example, the pH of the solution when it is generated is high enough to account for some interfactant, or solubilization agent, partitioning into the extractant. This is to say that pH, as well as other factors, can be tailored to account for some interfactant partitioning into the organic phase in use. Accordingly, various properties of the solution can change when the solution is applied to a surface containing extractant, e.g., as a dispersion is formed with the extractant.

In some instances, permitting interfactant to partition into the extractant can be beneficial. For example, some interfactants exhibit antioxidant properties, serves as an antioxidant, serves as a disinfectant, serves as a sterilant, increase an extractant's affinity, and so forth. In these examples, the presence of interfactant in the extractant may prevent degradation due to oxidation or increase the affinity of the extractant to a product to be recovered. For example, some interfactants increase extractant butanol affinity (expressed as Kd, also at times referred to as the extractants butanol partition coefficient). This can be beneficial as not only does the interfactant promote efficient cleaning of surfaces fouled with extractant, but it can increase the efficiency of the extractant to recover butanol from a fermentation broth. Examples of interfactants include salicylic acid, salicylate esters, parahydroxybenzoic acid and esters.

An interfactant can be selected based on other rationales. As will be described in further detail below. In an example, an interfactant is selected because it permits efficient recovery of extractant. For example, while extractant adhering to a surface of fermentation equipment may be considered a contaminant, it is valuable for use in recovering additional fermentation product or to be sold as a co-product. In addition, recovering extractant minimizes the overall amount of waste, which typically is associated with a disposal cost.

The solution can be applied to a surface in a variety of ways. Example application procedures include, but are not limited to, immersion, spray-ball washing, rinsing, flushing, and so on fermentation and/or product recovery equipment, e.g., equipment included in an ISPR system. In embodiments, the solution is applied to a surface including extractant so the extractant is removed from the surface. The extractant in some instances comes separate from the surface due to or at least partially due to an interaction between the interfactant and the extractant. In embodiments, the interaction between the extractant and interfactant is reversible so the dispersion can be destabilized to recover the extractant, e.g., the dispersion is destabilized so the extractant and aqueous solution phase separate.

As noted above, the solution when applied can have different properties or exhibit properties to different extents in comparison to dispersions or solutions that result. For example, the concentration of interfactant in an aqueous phase in a dispersion of extractant recovered from a surface, water, and interfactant, can be different than that of the solution that was applied to remove the extractant because some of the interfactant can partition into the extractant. In some embodiments, the solution includes interfactant in sufficient concentration so the solution is effective for minimizing or eliminating microorganisms. In this example, the solution acts as a biocide that in addition to removing extractant from a surface can decrease or eliminate biologically active contaminants from the surfaces with which it contacts.

In embodiments, the dispersion is collected. For example, the dispersion containing recovered extractant, water, interfactant is drained out a low-point drain on the equipment for recovery of the solution and/or extractant. A variety of approaches, devices, and equipment can be used to collect the dispersion during a cleaning cycle. For example, the dispersion is collected in a vessel over the course of one or more cleaning cycles before it is recycled, e.g., batch recycling. In other examples, the extractant and/or solution is recycled contemporaneously with its use.

The dispersion can be destabilized so the extractant and aqueous solution phase separate. For example, the dispersion is heated so the extractant forms an organic layer and the water separates into another layer. Example destabilization techniques include at least one of heating the dispersion, adjusting the dispersion's pH, adding reagent, adding another interfactant to substantially restore the interfacial tension between the extractant and solution to at least that before the applying, mechanical destabilization, centrifugation, coalescence, de-emulsifying, cooling the dispersion, or combinations thereof. For example, another interfactant can be added to the dispersion so the extractant and water separate from one another. As should be appreciated, the first interfactant may be primarily present in the aqueous phase, while a minor portion is present in the organic/extractant phase as described previously.

In embodiments, the dispersion phase separates because one or more conditions have changed between when the dispersion was generated by applying the solution to the surface containing the extractant and when it is destabilized for extractant/solution recovery. For example, the dispersion is generated at a first condition (e.g., temperature) when the solution is applied to the extractant, while the dispersion is destabilized by changing conditions, e.g., obtaining a second condition such as heating the dispersion to a second temperature that is different than the first. The second condition may be associated with at least one of a mechanically destabilized version of the dispersion at the first condition, a coalesced version of the dispersant at the first condition, a de-emulsified version of the dispersion at the first condition, or combinations thereof.

In some embodiments, the solubility of the interfactant in water can vary with temperature. For example, the solubility of tributyl phosphate is about 1000 mg/L at 4° C. and decreases to 0.003 mg/L at fifty degrees Celsius (50° C.). Increasing temperature may also decrease the dispersability of COFA in the solution. This property can be utilized to manipulate the recovery of a COFA phase and retention of phosphate ester in the cleaning solution. For example, a solution comprising phosphate ester can be used at ambient temperature to remove COFA from fermentation equipment and disperse it in the solution. The solution may be subsequently heated to a higher temperature which would enable a separable COFA phase to form. This COFA phase can be removed and washed with water at ambient temperature to recover the interfactant, e.g., the phosphate ester.

An additional example of the foregoing, is applying the solution to a surface containing the extractant at a first temperature between thirty degrees and one hundred degrees Celsius (30-100° C.) and then heating the dispersion to a second temperature that is higher than the first temperature but is also in the range of between thirty degrees and one hundred degrees Celsius (30-100° C.). In embodiments, implementing an interfactant capable of removing extractant and phase separating in the thirty to one hundred degree Celsius range is implemented to account for water present in the solution. In some embodiments, the difference between the first and second temperatures is five degrees or approximately five degrees. A five degree separation may permit accurate phase separation while minimizing energy consumption due to heating/cooling and so on.

The separate phases can be recycled for reuse and/or for inclusion in a co-product stream. For example, the solution can be purified by removing contaminates collected during use while recovered extractant is purified to remove contaminates, etc. Example purification techniques include filtration, mechanical separation, distillation, evaporation, vacuum assisted distillation/evaporation, pH adjustment, sterilization, adding reagent, and so on. The extent and purification techniques employed can vary based on a various factors including, but not limited, to whether the extractant or solution will be reused, what type and/or amount of contaminates are present in the solution/extractant, the occurrence of chemical degradation of the extractant/solution and so forth. In some embodiments, recycling extractant/solution comprises recharging extractant and/or solution with one or more of additional additives to replace additives lost during cleaning; new extractant/solution; additional interfactant or solubilization agent; and the like. For example, additional interfactant is incorporated into the used solution so the solution includes a sufficient concentration of interfactant.

In some embodiments, methods for decontaminating a fermentation system implement a solution including a solubilization agent. Additionally, embodiments are disclosed for recovering extractant, such as extractant adhered to a surface included in a fermentation system through use of a solution including a solubilization agent. The recovered extractant can be recycled for reuse as an extractant and/or for inclusion in a co-product stream for alcohol production, e.g., fusel production. A solubilization agent may be selected over use of an interfactant because the solubilization is produced as a co-product that results from fermentation. For example, a solubilization is selected because it is relatively low cost/low demand fermentation co-product that is effective for removing extractant.

In examples, in accordance with these embodiments, a solution containing a solubilization agent is generated by mixing a sufficient amount of a solubilization agent with water, and optionally additives. Example solubilization agents include, but are not limited to, butyric acid, isobutanol, isoamyl alcohol, isobutyric acid, salicylic acid and esters, paraben acid and esters, dimethylacetamide, acetamide, formamide, dimethyl formamide, dimethyl acetamide (DMAC), and combinations thereof. The amount of solubilization agent included in the solution can be effective to ensure removal of extractant from a surface of, for example, a piece of equipment or a device included in the fermentation system. The amount of solubilization agent added to the solution can also be effective so water present in the solution and extractant removed from the surface form a homogeneous solution. This is to say, that enough solubilization agent is added to the water so the solution is effective to remove extractant that clings to the surface while forming a solution that is substantially homogenous. Other consideration can be taken into account including whether the solubilization agent partitions into the extractant, the toxicity or biocidal activity of the solubilization agent, antimicrobial activity, disinfecting capability, sterilizing ability, antioxidant ability, and the like considerations.

In some embodiments, a metabolite co-produced with butanol during fermentation is included in the solution. For example higher boiling fermentation co-products including acetic acid, isobutyric acid, isoamyl alcohol and butanediol among others can be included in a solution. Other suitable additives include salicylic acid, salicylate esters, parahydroxybenzoic acid, parahydroxybenzoate esters, and combination thereof. The foregoing compounds can be used in combination with other additives, interfactants, solubilization agents, and so on. These compounds in sufficient concentration in an aqueous cleaning solution can solubilize COFA while they may disperse COFA when included in lower concentration in the aqueous phase in some instances.

A cleaning solution containing a solubilization agent may be used to ensure that the extractant is removed from a surface. A solubilization solution is used if distillation, evaporation separation of extractant/solution is to be performed. A variety of other considerations can be implemented when selecting a solubilization agent and/or how much solubilization agent to include in solution. Solubilization agent selection, similar to interfactant selection can implement other considerations. Example factors that can be consider include, surface tension, extractant to be removed, the butanol affinity of the solubilization agent, solubilization agent toxicity to microorganism, solubilization agent ability to partition into the extraction (e.g., the solubilization agent's hydrophilic/oleophilic properties), and so forth. Other factors that can be considered include equipment fill/drain rates, application technique (e.g., wash, spray ball wash, rinse, immersion wash), composition of surface (e.g., metal type, smoothness, existence of scaling), other cleaning techniques to be implemented, and the like.

In some instances, log P of these solubilization agents increase with increases in temperature. Thus, heating/cooling can be used to determine whether the extractant is soluble in the solution or whether it comes out of solution. Log P is a partition coefficient of a compound in a mix with octanol and water.

The solution containing the solubilization agent can be applied using a variety of techniques. Example techniques include, but are not limited to, washes, rinses, spray ball washing, spray application, reverse flow washes, and combinations thereof. The application technique implemented can depend on the system, equipment, or device to be cleaned. For example, a reverse flow wash is used to clean a static mixer or a settler while a spray ball wash is used to decontaminate a vessel of extractant and other contaminants, such as solids, microorganism contaminants, and so on.

The solution, that now contains extractant removed from a surface, can be collected for separation and recycling of the extractant and/or the solution. Although various separation techniques can be used, example techniques include distillation, evaporation, vacuum assisted separation, and combinations thereof. Accordingly, the separated solution and extractant can be recycled for reuse and/or included in a co-product stream such as in the case of the extractant. For example, once purified, recovered extractant can be used as an additive for animal feed.

In embodiments, recycling comprises incorporating additional solubilization agent and/or additives in the solution so the used solution is similar to solution at generation or prior to application. For example, additional solubilization agent is added so it is included in solution in a sufficient concentration to promote efficient extractant removal, form a homogeneous solution, and so on.

Other example extractants that may be removed using the described solutions include, but are not limited to one or more of the following fatty acids: azaleic, capric, caprylic, castor, coconut (i.e., as a naturally-occurring combination of fatty acids, including lauric, myrisitic, palmitic, caprylic, capric, stearic, caproic, arachidic, oleic, and linoleic, for example), dimer, isostearic, lauric, linseed, myristic, oleic, olive, palm oil, palmitic, palm kernel, peanut, pelargonic, ricinoleic, sebacic, soya, stearic acid, tall oil, tallow, #12 hydroxy stearic, or any seed oil. In some embodiments, the extractant is one or more of diacids, azaleic, dimer and sebacic acid. Thus, the extractant can be a mixture of two or more different fatty acids. In embodiments, the extractant is a fatty acid derived from chemical or enzymatic hydrolysis of glycerides derived from native oil. For example, the extractant is free fatty acids obtained by enzymatic hydrolysis of native oil such as biomass lipids. In embodiments, the extractant is a fatty acid extractant selected from the group consisting of fatty acids, fatty alcohols, fatty amides, fatty acid methyl esters, lower alcohol esters of fatty acids, fatty acid glycol esters, hydroxylated triglycerides, and combinations thereof, obtained from chemical conversion of native oil such as biomass lipids as described in U.S. Patent Publication No. 2011/0312044.

In some embodiments, the cleaning and/or extractant recovery procedures described herein can be used in conjunction with additional decontamination procedures. For example, the procedures described above can be used in conjunction with one or more of an acid wash, an acid rinse, a water rinse, a caustic wash, a caustic rinse, a steam treatment, a detergent wash, and the like for cleaning or sterilizing equipment included in a fermentation system and/or a distillation system.

Static Mixer Use and Decontamination

Figure 7:
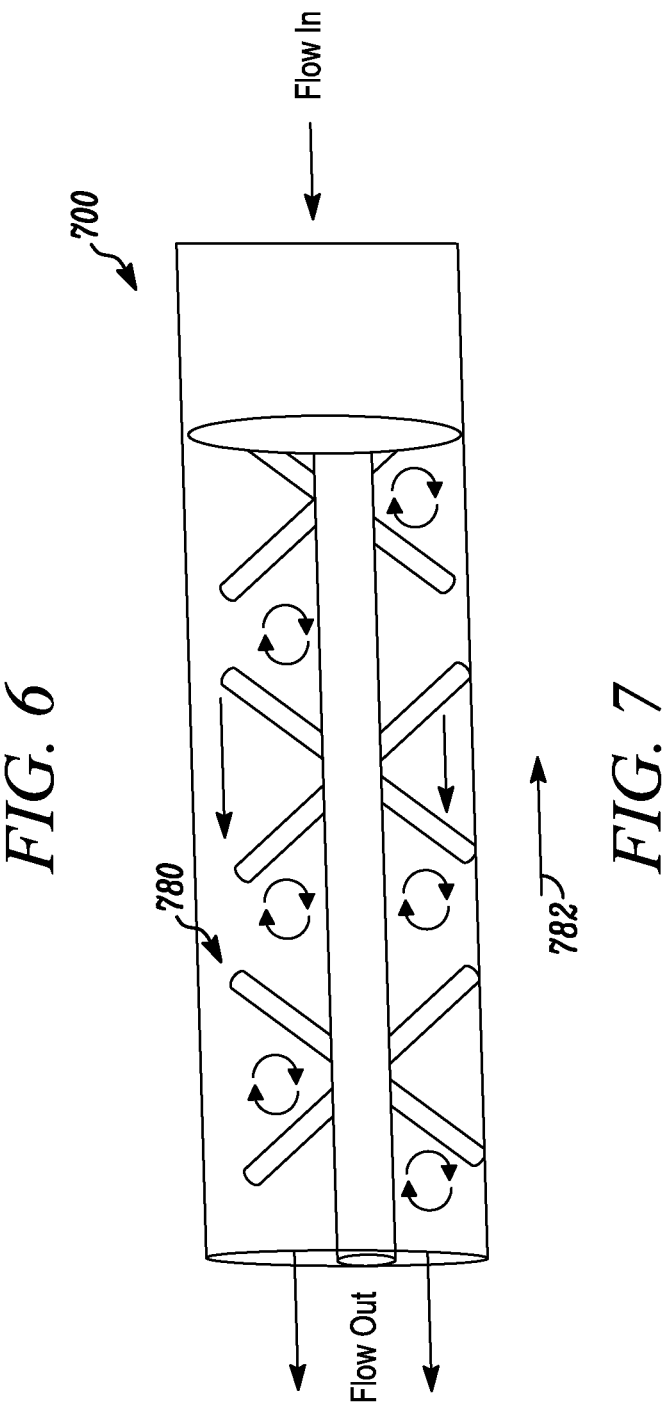
FIG. 7 illustrates a static mixer that is configured to implement frozen extractant decontamination.

Referring now to FIG. 7, in embodiments, a fermentation system 102 includes one or more static mixers (one mixer 700 is illustrated). Static mixers are constructed to mix fluids flowing through it. The mixer 564 illustrated in FIGS. 5A and 5B can be a static mixer that is configured to mix as fermentation broth and extractant. Additionally, a static mixer can mix solids or particles such as fermentation solids included the broth as well.

As illustrated in FIG. 7, the static mixer 700 includes one or more baffles 680 (one is referenced) that are shaped to cause turbulence in the liquid in order to mix it. Baffles can have a variety of shapes and configurations based on the liquid to be mixed. As a result, a variety of factors can impact the mixer 700 performance. Example factors include, but not limited to, flow rate, droplet size, immiscibility (in mixtures of liquids), presence/absence of solids, specific gravity of one or more liquids, and so on. In the current embodiment, the static mixer 700 is configured to mix extractant and fermentation broth flowing through the mixer 600 to promote butanol extraction, from the broth. The mixer 700 can be designed and operated to ensure proper mixing, e.g., form extractant or broth droplets of a particular size, distribute droplets in the broth, etc. to promote efficient mass transfer. The static mixer's efficiency can be influenced by a variety of factors including flow rate, pressure drop, the fluids' specific gravity values, the existence or absence of particles, etc. through the mixer 700.

In embodiments, the mixer 700 is selected/designed to mix a fatty acid extractant, e.g., COFA, with water or fermentation broth. Extractants may be immiscible, substantially immiscible, or partially immiscible in water. COFA for example is generally immiscible with an aqueous liquid. In the previous example, the mixer 700 can blend COFA and fermentation broth (rich broth containing fermentation product) to form a biphasic mixture of immiscible COFA droplets, of a tailored size, mixed with the fermentation broth. Mixing COFA and broth to form droplets can promote efficient mass transfer of, for example, isobutanol or other products as droplets offer a large surface area for mass transfer of butanol to the extractant.

Although efficient for mixing liquids, static mixer can be subject to contamination that is difficult to clean due to the shape and complexity of its interior surfaces. For example, some static mixers include constricted geometries that increase the likelihood of contamination in comparison to wider or less constricted geometries. Fermentation solids and other contaminants can lodge on a surface of the baffle or other portions of the static mixer. In other examples, crude soaps can form on the baffle's surface if fatty acid extractant happens to come in contact with caustic cleaning solution. As a result, decontaminating a static mixer can be difficult as some mixers include dead zones that trap material, have complex surfaces that are not amenable to mechanical cleaning, or include surfaces that are impractical to clean with solutions such as the caustic/acidic solutions or water rinses as described above.

Accordingly, techniques for decontaminating static mixers are now described in greater detail. These techniques, devices, approaches, and systems described below can be implemented with a variety of static mixers including mixer 700 that is reference at various times in the following discussion.

In embodiments, frozen extractant can be introduced to the mixer 700 to remove contaminants from one or more interior surfaces. For example, a slush of frozen COFA is fed through the mixer to remove contaminants, contaminants that coat or are trapped on the surface of the baffles or other interior surfaces of the mixer. In additional embodiments, the slush comprises a slush of COFA and water, e.g., ice.

The mechanical interaction of the frozen COFA on the interior surfaces of the mixer can be sufficient to remove contaminants. For example, the friction generated by the frozen COFA rubbing against the interior surfaces of the mixer is sufficient to remove contaminants that are not readily removed by liquid CIP procedures. Contaminants that are not readily removed include particulate matter, crude soaps, contaminants trapped in dead zones, and so on.

In embodiments, the COFA slush is introduced as a plug or bolus of slush or frozen COFA that is forced through the mixer 700 at high pressure in comparison to the mixer's normal operating pressure/range of pressures. In other embodiments, the flow of the slush can be reversed through the static mixer, e.g., a reverse flow is used. For example, the system including the static mixer is configured to flow the slush though the mixer before the flow is reversed and the slush is transferred back through the mixer in the reverse direction. In other examples, a decontamination procedure includes flowing slush through the mixer in a direction opposite fluid flows through the mixer in typical operation, e.g., a counter flow. A counter flow direction is generally illustrated by arrow 782.

Employing frozen COFA or a COFA slush can improve cleanliness as the slush/frozen COFA can reach dead zones that are difficult to manually clean (mechanically clean). It is to be appreciated that a frozen or slush cleaning approach can be used in conjunction with the CIP techniques described in conjunction with FIGS. 5A and 5B. Frozen or slush COFA cleanings can be repeated a predetermined number of time or repeated until a predetermined condition is met. For instance, a fermentation system is configured to repeat slush cleanings until the mixer achieves a predetermined cleanliness threshold. Although in-line chillers/coolers can be used to freeze/chill the COFA to a point where it solidifies, in embodiments, frozen COFA and/or COFA slush can be generated external to the system, e.g. the fermentation system, and manually introduced to the mixer 700. Frozen COFA or COFA slush that is used, can be shunted from the system or permitted to melt and removed via a water rinse or other liquid based cleaning technique. Additionally, additives for frozen/slush COFA include cleaning agents, solid materials (e.g., corn mash), dispersants, wetting agents, antimicrobial agents, detergents, and the like.

Further modifications and alternative embodiments of this disclosure will be apparent to those skilled in the art in view of this description. It will be recognized, therefore, that the present invention is not limited by these example arrangements. Accordingly, this description is to be construed as illustrative only and is for the purpose of teaching those skilled in the art the manner of carrying out the methods, approaches, devices, equipment, systems, and so forth. It is to be understood that the forms of the invention herein shown and described are to be taken as the presently preferred embodiments. Various changes may be made in the shape, size and arrangement of parts. For example, equivalent elements may be substituted for those illustrated and described herein and certain features of the invention may be utilized independently of the use of other features, all as would be apparent to one skilled in the art after having the benefit of this description.

What is claimed is:

1. A method for decontaminating an in situ product removal (ISPR) system included in a fermentation system that is configured to produce fermentation product, comprising:
   introducing an extractant to the ISPR system as part of a decontamination procedure;
   maintaining the extractant in at least a portion of the ISPR system at a sufficiently high temperature wherein said sufficiently high temperature is higher than a temperature at which the extractant is implemented to remove fermentation product from a fermentation broth; and
   sterilizing equipment included in the ISPR system, wherein the surfaces of the equipment that contact the fermentation broth are substantially free of microorganisms that compete with or inhibit a microorganism that produces the fermentation product.

2. The method of claim 1, further comprising bypassing or ceasing operation of a cooler included in the ISPR system.

3. The method of claim 1, wherein the step of introducing the extractant comprises pumping the extractant at a rate to maintain the surfaces of the equipment at the sufficiently high temperature.

4. The method of claim 1, wherein the sufficiently high temperature is equal to or greater than seventy-five degree Celsius (75° C.).

5. The method of claim 4, wherein the sufficiently high temperature is insufficient to cause appreciable thermal degradation of the extractant.

6. The method of claim 1, wherein the extractant comprises corn oil fatty acid (COFA).

7. The method of claim 1, further comprising deinventoring the equipment by draining the equipment of any fermentation broth and/or extractant using a port that is not used to return lean fermentation broth to a vessel included in the fermentation system.

8. The method of claim 1, wherein the equipment comprises a settler or mixer.

9. The method of claim 1, wherein the microorganisms that compete with or inhibit a microorganism that produces the fermentation product comprise bacteria or wild-type yeast.

10. The method of claim 1, further comprising a step of monitoring the ISPR system for presence of a contaminant.

11. The method of claim 1, wherein the extractant comprises fatty alcohols, fatty acids, fatty esters, fatty aldehydes, fatty amides, triglycerides, monoalkyl phosphates, dialkyl phosphates, trialkyl phosphates, or mixtures thereof.

12. The method of claim 1, wherein the fermentation system comprises propagation vessels, fermentation vessels, distillation columns, beer columns, condensers, and piping.

13. The method of claim 1, further comprising a step of recovering the extractant from the equipment.

14. The method of claim 13, wherein the extractant is recovered by application of a solution comprising an interfactant to the surfaces of the equipment.

15. The method of claim 14, wherein the interfactant comprises urea, alkyl urea, a quaternary ammonium salt, a choline salt, a polyether glycol, ethoxylate, triethyl phosphate, tetramethyl urea, tetraethyl urea, short chain phosphate, an alkyl phosphate, a bridging compound, or combinations thereof.

* * * * *